(12) United States Patent
Ohno et al.

(10) Patent No.: US 7,651,837 B2
(45) Date of Patent: Jan. 26, 2010

(54) METHOD FOR DETECTING AND IDENTIFYING MICROORGANISM CAUSATIVE OF INFECTION

(75) Inventors: Tsuneya Ohno, 5-15, Fukazawa 2-chome, Setagaya-ku, Tokyo 158-0081 (JP); Akio Matsuhisa, Osaka (JP)

(73) Assignees: Fuso Pharmaceutical Industries, Ltd., Osaka (JP); Tsuneya Ohno, Tokyo (JP)

( * ) Notice: Subject to any disclaimer, the term of this patent is extended or adjusted under 35 U.S.C. 154(b) by 382 days.

(21) Appl. No.: 10/479,185

(22) PCT Filed: May 27, 2002

(86) PCT No.: PCT/JP02/05107

§ 371 (c)(1),
(2), (4) Date: Jun. 21, 2004

(87) PCT Pub. No.: WO02/099133

PCT Pub. Date: Dec. 12, 2002

(65) Prior Publication Data

US 2006/0234219 A1     Oct. 19, 2006

(30) Foreign Application Priority Data

May 31, 2001   (JP)   ............... 2001-165929

(51) Int. Cl.
*C12Q 1/68*      (2006.01)
*C12Q 1/37*      (2006.01)
*G01N 1/30*      (2006.01)

(52) U.S. Cl. ............... 435/6; 435/23; 435/24; 435/40.51

(58) Field of Classification Search ............. None
See application file for complete search history.

(56) References Cited

U.S. PATENT DOCUMENTS

| 4,737,455 A | 4/1988 | De Baetselier |
| 5,358,846 A | 10/1994 | Ohno et al. |
| 5,364,790 A * | 11/1994 | Atwood et al. ........... 435/287.2 |

(Continued)

FOREIGN PATENT DOCUMENTS

EP   159653   10/1985

(Continued)

OTHER PUBLICATIONS

Matsuhisa, A. et al. Detection of *Staphylococci* in mouse phagocytic cells by in situ hybridization using biotinylated DNA probes. Biotechnic & Histochemistry 69(1):31-37 (1994).*

(Continued)

*Primary Examiner*—Diana B Johannsen
(74) *Attorney, Agent, or Firm*—Marshall, Gerstein & Borun LLP

(57) ABSTRACT

Causative microorganisms of infectious diseases are detected and/or identified rapidly and with high sensitivity by taking phagocytes from clinical specimens containing active phagocytes, immobilizing the phagocytes so taken, treating the phagocytes to improve cell membrane permeabilities thereof, further treating the phagocytes to bare DNA in the causative microorganisms which might exist in the phagocytes, and detecting the causative microorganisms with DNA probes which can hybridize with such DNA under stringent conditions.

17 Claims, 11 Drawing Sheets

(d) PMSF 0.1mmol/mL

U.S. PATENT DOCUMENTS

| | | | |
|---|---|---|---|
| 5,582,985 | A | 12/1996 | Thompson |
| 5,708,159 | A | 1/1998 | Ohno et al. |
| 5,807,673 | A | 9/1998 | Ohno et al. |
| 5,869,064 | A * | 2/1999 | Lindahl et al. ............ 424/244.1 |
| 6,235,890 | B1 * | 5/2001 | Morrison et al. .......... 536/24.33 |
| 6,268,123 | B1 | 7/2001 | Faff |
| 2007/0059687 | A1 * | 3/2007 | Ohno et al. .................... 435/6 |

FOREIGN PATENT DOCUMENTS

| | | |
|---|---|---|
| GB | 2 021 594 | 12/1979 |
| JP | 1-117800 | 5/1989 |
| JP | 08-205893 | 8/1996 |
| WO | WO 89/10411 | 11/1989 |
| WO | WO 94/01583 | 1/1994 |
| WO | WO 94/10341 | 5/1994 |
| WO | WO 94/28115 | 12/1994 |
| WO | WO 96/31522 | 10/1996 |
| WO | WO 99/54502 | 10/1999 |

OTHER PUBLICATIONS

Rasmussen, H.N. et al. Specific detection of pathogenic *Yersinia enterocolitica* by two-step PCR using hot-start and DMSO. Molecular and cellular probes 8(2):99-108 (Apr. 1994).*

International Search Report Application No. EPO 02 72 6495, Nov. 18, 2004.

Jansen, G. et al., "*Rapid Identification of Bacteria in Blood Cultures by Using Fluorescently Labeled Oligonucleotide Probes,*" Journal of Clinical Microbiology, Feb. 2000, p. 814-817.

Matsuhisa, et al., "*Detection of Bacteria in Phagocyte-Smears from Septicemia-Suspected Blood In Situ Hybridization Using Biotinylated Probes,*" Microbiol. Immunol., 38(7), 1994, pp. 511-517.

Arnold et al., Species-specific assessment of *Mycobacterium leprae* in skin biopsies by in situ hybridization and polymerase chain reaction, Lab. Invest., 66:618-623, 1992.

Chen et al., Electron microscope studies of the in vitro phagocytosis of *Mycobacterium* spp. By rainbow trout *Oncorhynchus mykiss* head kidney macrophages, Dis. Aquatic Organisms, 32:99-110, 1998.

Kedzierska et al., Granulocyte-macrophage colony-stimulating factor augments phagocytosis of *Mycobacterium avium* complex by human immunodeficiency virsu type 1-infected monocytes/macrophages in vitro and in vivo, J. Infect. Dis., 181:390-394, 2000.

Kolb-Maurer et al., Listeria monocytogenes-infected human dendritic cells: uptake and host cell response, Infection and Immunity, 68:3680-3688, 2000.

Matsuhisa et al., Clinical utility of in situ hybridization method for the diagnosis of sepsis, Bio Clinica, 14:97-101, 1999.

Heine et al., Anaesthesia with propofol decreased FMLP-induced neutrophil respiratory burst but not phagocytosis compared with isoflurane, Br. J. Anasth., 85:424-430, 2000.

International Search Report, PCT/JP2002/05106, Japanese Patent Office, published Sep. 3, 2002.

Supplemental Partial European Search Report, EP 02778910, published Nov. 18, 2004.

* cited by examiner (a) $1 \times 10^8$ Cells/mL (b) $5 \times 10^7$ Cells/mL (c) $1 \times 10^7$ Cells/mL (d) $5 \times 10^6$ Cells/mL (e) $1 \times 10^6$ Cells/mL (f) $5 \times 10^5$ Cells/mL (a)

(b) PMSF 1 μmol/mL (c) PMSF 10 μmol/mL (d) PMSF 0.1mmol/mL (e) PMSF 1mmol/mL (a) SA Digested Sample (b) SE Digested Sample (c) PA Digested Sample (d) EF Digested Sample (e) EK Digested Sample Arrow in the Photographs indicated the digested Bacteria.

(a) Non-Digested SA (b) Non-Digested EF (c) Digested SA (d) Digested EF

SA : SA Digested Sample
SE : SE Digested Sample
PA : PA Digested Sample
EF : EF Digested Sample
EK : EK Digested Sample (a) EC-24

(b) EC-34

(c) EC-39

(d) MIX

METHOD FOR DETECTING AND IDENTIFYING MICROORGANISM CAUSATIVE OF INFECTION

TECHNICAL FIELD

The present invention relates to an improved method for detecting and identifying causative microorganisms of infectious diseases. The present invention also relates to a kit for detecting and/or identifying causative microorganisms of infectious diseases, a method for monitoring genes from exogenous microorganisms in clinical specimens, and a method for determining causative microorganisms of sepsis and those of bacteriemia.

BACKGROUND ARTS

Although the hemoculture methodologies have popularly been used conventionally as a mean to verify bacteria in the blood, since this methodology needs about from 3 to 14 days to culture and isolate the subjected bacteria and detection rates thereby are as low as about 10%, it was not well contributed in the diagnosis for treating serious diseases like sepsis.

The present inventors had invented, to solve such problems, a method for detecting and identifying exogenous-microorganisms digested with phagocytes comprising a step of detecting genes from such exogenous-microorganisms in the phagocytes by in situ hybridization employing a probe which can specifically hybridize with the genes (Japanese Patent Publication No. 7-40).

The method of Japanese Patent Publication No. 7-40 have been in the limelight in the field of infectious deseases because, in comparison with the conventional hemoculture methodology, the method allowed about four times rapidly detection of the subjected bacteria in bloods from patients who are under the suspicion about sepsis, and detection results were appeared within 24 hours.

Objects of the present inventions is an improvement of detection effects and of detection sensitivity to be offered by the method according to Japanese Patent Publication No. 7-40 for detecting and/or identifying causative microorganisms of infectious diseases by taking phagocytes from the clinical specimens containing active phagocytes, immobilizing the phagocytes so taken, treating the phagocytes to improve cell membrane permeabilities thereof, further treating the phagocytes to bare DNA in the causative microorganisms which might be existed in the phagocytes, in situ hybridizing DNA so bared with detective DNA probe(s) which can hybridize with such bared DNA under stringent conditions, and detecting and/or identifying the causative microorganisms based on signals so detected.

DISCLOSURE OF INVENTION

The present invention has been completed in view of the problems aforenoted and the merits thereof are as follows.

A method for detecting and/or identifying causative microorganisms of infectious diseases by taking phagocytes from the clinical specimens containing active phagocytes, immobilizing the phagocytes so taken, treating the phagocytes to improve cell membrane permeabilities thereof, further treating the phagocytes to bare DNA in the causative microorganisms which might be existed in the phagocytes, in situ hybridizing DNA so bared with detective DNA probe(s) which can hybridize with such bared DNA under stringent conditions, and detecting and/or identifying the causative microorganisms based on signals so detected, the method comprises at least one condition(s) to be selected from the following conditions (1)-(8) of;

(1) Cell density (X cells/ml) of the phagocytes to be immobilized is $5 \times 10^6$ cells/ml$<$X cells/ml$<1 \times 10^8$ cells/ml, (2) Lysostaphin is applied into the step to bare DNA in the titer of from 1 Unit/ml to 1,000 Units/ml, (3) Lysozyme is applied into the step to bare DNA in the titer of from 1,000 Units/ml to 1,000,000 Units/ml, (4) N-acetylmuramidase is applied into the step to bare DNA in the titer of from 10 Units/ml to 10,000 Units/ml, (5) Zymolyase is applied into the step to bare DNA in the titer of from 50 Units/ml to 500 Units/ml, (6) Surfactant is applied into the step of in situ hybridization, (7) Such DNA probe(s) is/are one or more DNA probe(s) to be determined with their chain length of from 350 bases to 600 bases, and (8) Concentration of such DNA probe(s) is from 0.1 ng/µl to 2.2 ng/µl.

The step to bare DNA employs preferably one or more enzyme(s) selected from Lysostaphin in the titer of from about 10 to about 100 Units/ml, Lysozyme in the titer of from about 10,000 to about 100,000 Units/ml, N-acetylmuramidase in the titer of from about 100 to about 1,000 Units/ml and Zymolyase in the titer of from about 100 to about 500 Units/ml.

The step to bare DNA preferably employs enzyme(s), and the enzyme(s) is/are subjected to a reaction to be performed under the temperature of from about 26° C. to about 59° C. for from about 15 to about 120 minutes.

The step to bare DNA further employs preferably substance(s), in particular, phenylmethylsulfonyl fluoride to keep a form of the phagocytes under the concentration of preferably from about 10 µmol/l to about 10 mmol/l.

As the substance to keep a form of the phagocytes, substance dissolved into dimethylsulfoxide is preferable. The substance dissolved in dimethylsulfoxide is employed as that to keep a form of the phagocytes, then, concentration of the dimethylsulfoxide in a solution to be used in the step to bare DNA is adjusted to less than 5%.

The in situ hybridization step is performed by hybridizing DNA with DNA probe(s) under the presence of surfactant(s), in particular, the anionic surfactant, preferably, sodium dodecyl sulfate (SDS).

Hybridization reaction in the in situ hybridization step is performed under the temperature of from about 20° C. to about 50° C. and time of from about 30 to about 900 minutes.

The method further comprises, prior to the immobilization step, a step to mount the phagocytes so taken onto the solid support and a slide coated with 3-aminopropyl triethoxysilane is employed as such solid support.

Pigment(s) is/are also employed at the signal detection to distinguish contrast between signals and cells. Preferably, blood is employed as the clinical specimen.

The present invention further provides a kit for detecting and/or identifying causative microorganisms of infectious diseases by taking phagocytes from the clinical specimens containing active phagocytes, immobilizing the phagocytes so taken, treating the phagocytes to improve cell membrane permeabilities thereof, further treating the phagocytes to bare DNA in the causative microorganisms which might be existed in the phagocytes, in situ hybridizing DNA so bared with detective DNA probe(s) which can hybridize with such bared DNA under stringent conditions, and detecting and/or identifying the causative microorganisms based on signals so detected, the kit comprises the following elements (1)-(2) of;

(1) at least one enzyme(s) to be employed in the step to bare DNA which is/are selected from Lysostaphin, Lysozyme, N-acetylmuramidase and Zymolyase; and (2) at least one detective DNA probe(s).

Then, the present invention further provides a method for monitoring a gene of exogenous microorganisms digested with the phagocytes in the clinical specimens containing active phagocytes comprising the step of detecting the gene with in situ hybridization method employed in the foregoing method, wherein the gene of exogenous microorganisms in the clinical specimens is monitored.

The present invention further provides a method for diagnosing sepsis or bacteriemia comprising the step of identifying a gene of candidate causative microorganisms with in situ hybridization method employed in the foregoing method, wherein the causative microorganisms for sepsis or bacteriemia are determined based on the identification results.

BEST MODE FOR CARRYING OUT THE INVENTION

Figure 1:
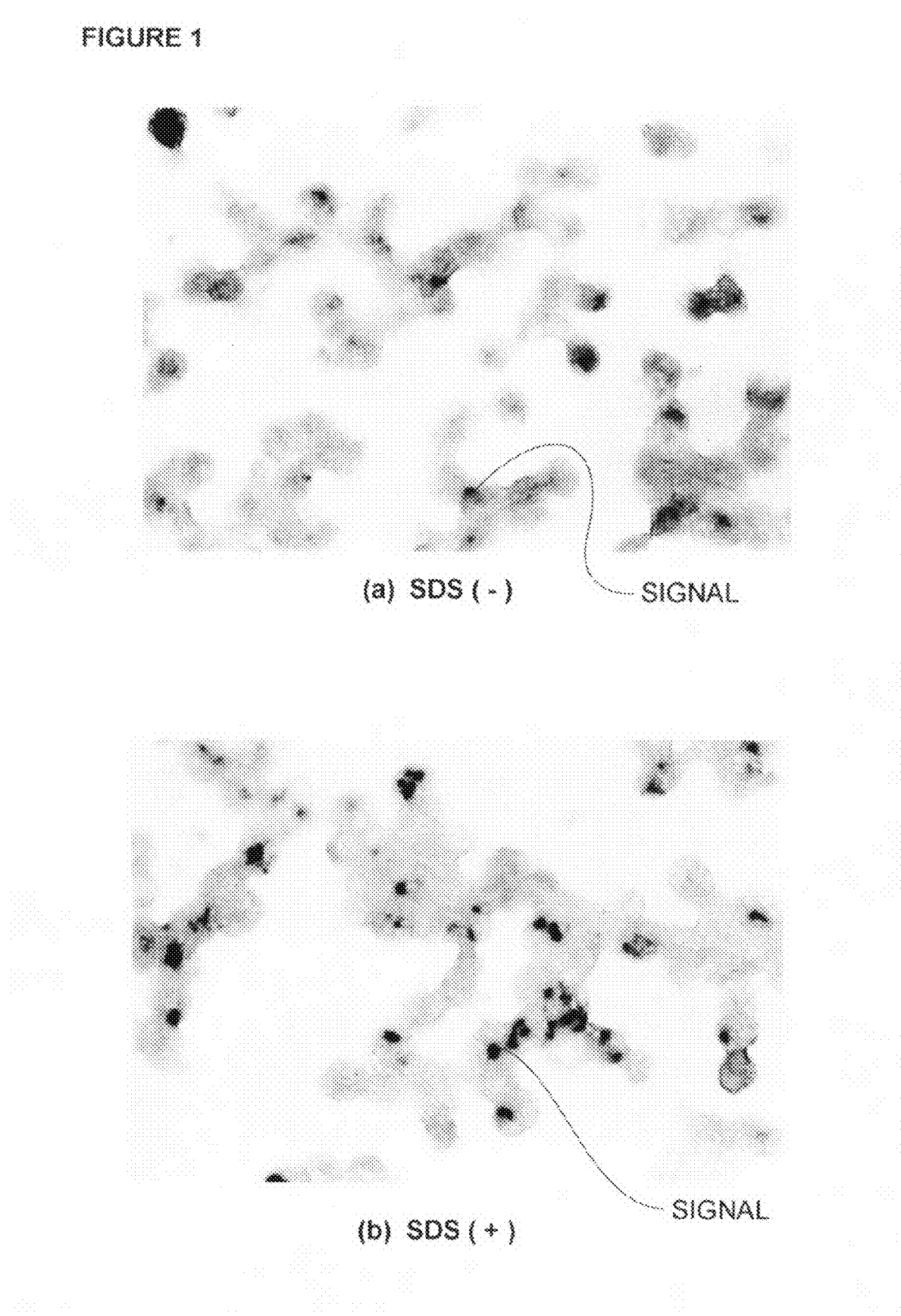
FIG. 1 is a view of illustrating results of in situ hybridization performed under (a) the absence of surfactant (SDS) and (b) the presence of surfactant (SDS).

Any clinical specimen containing active phagocytes is applicable as a specimen to be employed in the present embodiment and may includes fluidus like blood, histofluid, lymph, neurolymph, pus, pituita, nasal mucus or sputum. Then, active phagocytes are contained in urea, ascites or dialysate in the disorder like diabetes, nephropathia or hepatopathy and are also remained in the lotion used to wash rhinonem, bronchus, skin, various organs or bones, they can therefore also be employed as specimen of the present invention.

In addition thereto, tissues taken from skin, lung, kidney, mucosa or the like are also employed as the clinical specimen in the present invention. This is because that macrophage, which is one of phagocytes, has various forms including monocytes, alveolar macrophage, celiac macrophage, fixed macrophage, free macrophage, Hansemann's macrophage, inflammatory macrophage, liver Kupffer cells and brain microglia cells, tissues containing those can therefore also be employed, besides blood, as the clinical specimen of the present invention. For example, causative microorganisms of nephritis can be detected and identified by collecting kidney tissues through biopsy from patients who are under the suspicion about nephritis, taking phagocytes in the tissues through digestion thereof with enzymes like trypsin to exfoliate cells, and utilizing the phagocytes so taken.

The term 'phagocytes' used herein is directed to any cell which can incorporate into itself foreign objects like exogenous microorganisms and may includes, for example, macrophage, monocytes, neutrophil and eosinophil. Phagocytes line like U937 Cell, HL60 Cell or the like is also available. Exogenous microorganisms which may cause infectious diseases are microorganisms to be digested with phagocytes and may includes, for example, bacteria, mycete, virus, protozoon, parasite or the like. Bacteria may include, for example, *Staphylococcus, Pseudomonas, Enterococcus, Colibacillus, Streptococcus, Pneumococcus, Tubercle bacillus, Helicobacter pylori, Listeria, Yersinia, Brucellar* or the like. Mycete may include, for example, *Candida, Aspergillus, Actinomyces, Coccidioides, Blastomyces* or the like. Virus may include Influenza virus, Poliovirus, Herpes virus, Hepatitis virus and AIDS virus. Protozoon may include, for example, *Karyamoebina falcata, Trichomonas vaginalis*, Malaria, *Toxoplasma* or the like. Parasite may include, for example, *Trypanosoma* or the like. In particular, the causative microorganisms of sepsis or bacteriemia may include, for example, Gram-Positive Bacteria of *Staphylococcus* genus (*Staphylococcus aureus, Staphylococcus epidermidis*) and *Enterococcus* genus (*Enterococcus faecalis, Enterococcus faecium, Streptococcus pneumoniae, Streptococcus pyogenes, Streptococcus agalactiae*), Gram-Negative Bacteria like *Colibacillus*-related Enterobacteriaceae Family of *Escherichia coli, Enterobacter cloacae, Klebsiella pneumoniae* (*Klebsiella oxytoca, Serratia marcesens, Proteus vulgaris, Citrobacter freundii*), aerophilic rod of *Pseudomonas* genus (*Pseudomonas aeruginosa*), anaerobe of *Clostridium* genus (*Clostridium perfringens*), *Bacteroides* genus (*Bacteroides fragilis*) or the like. Also, *Acinetobacter calcoaceticus, Aeromonas hydrophilia, Flavobacterium meningosepticum, Bacillus cereus* can rarely be fallen within the causative microorganisms.

Phagocytes (Leukocytes) fractions can be taken from the clinical specimen according to the conventional method. For example, about 5 ml (or 10 ml with a few leukocyte) of heparinized venous bloods were obtained and the bloods were mixed with the blood components separative reagent (adjusted with sterilized-purified water to be 25 ml as their final volume containing 225 mg of Sodium Chloride and 1.5 g of Dextran (Molecular Weight: 200,000-300,000)) in the ratio of 4:1. Leukocyte fractions (the upper layer) were then obtained by leaving them at from about 10 to about 40° C. for from about 15 minutes to about 120 minutes, preferably, about 37° C. for about 30 minutes. Leukocytes were appeared by centrifuging the leukocyte fractions so taken in from about 100×g to about 500×g, at from 0° C. to about 20° C. for about from 3 minutes to about 60 minutes, preferably, in from about 140×g to about 180×g, at about 4° C. for about 10 minutes. Hemolysis is preferable if erythroblasts are entered at this step. Pelletized leukocytes so obtained were, for example, suspended with 1 ml of sterilized-purified water and the suspension were immediately put into an isotonic state by adding thereto excessive amounts of PBS (prepared by diluting twenty-fold with sterilized-purified water the raw solution (PBS Raw Solution; hereinafter simply referred to as 'PBS Raw Solution') which have been adjusted with sterilized-purified water to be 120 ml as their final volume containing 18.24 g of Sodium Chloride, 6.012 g of Sodium Monohydrogen Phosphate Didecahydrate and 1.123 g of Sodium Dihydrogen Phosphate Dihydrate), and such suspension were re-centrifuged in from about 140×g to about 180×g, at 4° C. and for about 10 minutes. Otherwise, such digested phagocytes can be adhered to the slides to be noted later through their native adhesionability without any centrifugation aforenoted.

Methodology to fix the leukocytes may include, for example, Carnoy s fixation. In particular, leukocytes are mounted onto a support (a supportive medium) which can hold the leukocytes and are immersed in Carnoy s fixative solution (prepared by mixing Ethanol, Chloroform and Acetic Acid in the volume ratio of 6:3:1) for 20 minutes and were immersed in from about 50% to about 90%, preferably, about 75% Ethanol solution for five minutes. Finally, they were completely air-dried.

Insoluble materials are preferable for the support and may include, for example, glass, metal, synthesized resin (e.g., polystyrene, polyethylene, polypropylene, polyvinyl chloride, polyester, polyacrylic ester, nylon, polyacetal and fluoric resin) and polysaccharide (e.g., cellulose and agarose).

A form of the insoluble support can be changed optionally and may include, for example, that of plate, tray, ball, fiber, rod, disk, container, cell or tube.

Particularly preferred support in the present embodiment is to emply slides. Such slide may include, for example, the slide (PRODUCTS ID. S311BL) of JAPAN AR BROWN CO., LTD. This slide (PRODUCTS ID. S311BL) has 14 circular wells of 5 mm diameter. In order to improve an adhesionability of the subjected cells at the actual use, APS coated slides to be made by coating 3-aminopropyltriethoxysilane (APS, SIGMA) onto the slides are recommended. The other slides to be made by coating poly-L-lysine or gelatin are also available.

APS coated slides are prepared by putting the slides (PRODUCTS ID. S311BL) onto a holder, immersing them into the diluted neutral detergent for 30 minutes or more, removing well the detergent with tap water, then washing the slides with purified water, and drying well the same under the higher temperature (100° C. or more) followed by leaving it under the room temperature. Thereafter, these slides are immersed into acetone containing 2% APS for one minute and are immediately rinsed gently with acetone then with sterilized-purified water. These slides were then air-dried. These slides are re-immersed into acetone containing from about 1° C. to about 10% APS for one minute, are immediately rinsed gently with acetone then sterilized-purified water, and are air-dried. Finally, these slides are dried under the temperature of from about 20° C. to about 60° C., preferably of 42° C. to realize the APS coated slides.

Leukocytes are mounted onto the APS coated slides preferably by smearing the leukocytes to realize the extended mono-layer thereof and drying the same. Cell population (X cells/ml) of the immobilized phagocytes should be adjusted to that of about $5 \times 10^6$ cells/ml<X cells/ml<about $1 \times 10^8$ cells/ml, preferably, about $1 \times 10^7$ cells/ml$\leq$X cells/ml$\leq$about $5 \times 10^7$ cells/ml.

Then, according to change on the phagocytes population per 1 ml, leukocyte population to be immobilized in the single well of the APS coated slide (y cells/well (diameter: 5 mm)) are adjusted that of about $2.5 \times 10^4$ cells/well<y cells/well<about $5 \times 10^5$ cells/well, preferably, about $5 \times 10^4$ cells/well$\leq$y cells/well$\leq$about $2.5 \times 10^5$ cells/well. In particular, pelletized leukocytes are prepared by centrifuging leukocyte fractions in from about 140×g to about 180×g, at 4° C. and for 10 minutes, adding small amount of PBS to the pelletized leukocytes, suspending the same, and counting the population with a hemacytometer. Leukocytes were duly mounted on the APS coated slides by smearing 5 μl of the leukocyte suspension into each well of the slides adjusted with PBS to be cell population of from about $5 \times 10^4$ cells/well to about $2.5 \times 10^5$ cells/well, then extending mono-layer of the leukocytes, and completely air-drying the same.

In order to accelerate permeability of the phagocyte membrane, they were immersed in PBS for from about 3 minutes to about 30 minutes, then in the solution prepared by diluting from about 2-fold to about 50-fold a pretreatment reagent (prepared by mixing 1.25 g of Saponin, 1.25 ml t-octylphenoxy-polyethoxyethanol (specific gravity of 1.068-1.075 (20/4° C.), pH (5 w/v %) 5.5-7.5) and 25 ml PBS Raw Solution, and adjusting with sterilized-purified water to be 50 ml as their final volume), and were applied to a centrifuge for from about 3 minutes to about 30 minutes.

In order to bare DNA in the causative microorganisms, an enzyme solution was prepared by adding, per single slide, 1 ml of a reagent solvent (prepared by diluting about 100-fold, with PBS, Dimethyl Sulfoxide (DMSO) containing 0.1 mol/l Phenylmethyl Sulfonylfluoride (PMSF)) to an enzyme reagent (N-acetylmuramidase, Lysozyme and/or Lysostaphin), then 1 ml of which were dropped under the temperature of from about 20° C. to about 60° C., preferably, from about 37° C. to about 42° C. in the wet chamber onto the area where the leukocytes were smeared and were left for from about 10 minutes to about 60 minutes. Then, they were immersed in PBS containing 0.2 mol/l Hydrochloric Acid (prepared by adding hydrochloric acid to PBS Raw Solution, diluting 20-fold the same with sterilized-purified water and adjusting final concentration of Hydrochloric Acid to 0.2 mol/l), and were applied to a centrifuge for 3-30 minutes to accelerate their permeability. 5% or more of DMSO concentration may lower activities of Lysozyme and Lysostaphin, DMSO concentration of less than 5% is therefore preferable. Besides PMSF, the known protease inhibitors like tosyllysinechlromethylketone (TLCK) and a combination thereof are also applicable to keep the form of phagocytes. Solvents like DMSO can be changed optionally to employ such known protease inhibitors.

With regard to the preferable titer range on each enzyme employed in the enzyme reagent, although Lysostaphin offer the substantial effect at the titer of 1 Unit/ml in the lysis of *Staphylococcus aureus*, that of 10 Units/ml or more was necessary in the lysis of *Staphylococcus epidermidis*. Optimum titer on Lysostaphin should therefore be adjusted to from about 1 Unit/ml to about 1,000 Units/ml, preferably, from about 10 Units/ml to about 100 Units/ml. When the titer of Lysozyme was about 10,000 Units/ml, there was no lysis on *Enterococcus faecalis* with N-acetylmuramidase of about 10 Units/ml or less titer. Also, when the titer of N-acetylmuramidase was about 100 Units/ml, there was no lysis with Lysozyme of about 1,000 Units/ml or less titer. Accordingly, optimum titer on N-acetylmuramidase should be adjusted to from about 10 Units/ml to about 10,000 Units/ml, preferably, from about 100 Units/ml to about 1,000 Units/ml, while that on Lysozyme acetylmuramidase should be adjusted to from about 1,000 Units/ml to about 1,000,000 Units/ml, preferably, from about 10,000 Units/ml to about 100,000 Units/ml. When the causative microorganisms are mycete like *Candida albicans*, titer on Zymolase should be adjusted to from about 50 Units/ml to about 500 Units/ml, preferably, from about 100 Units/ml to about 500 Units/ml. In particular, PMSF or the known protease inhibitors are useful in combination with Zymolase.

Enzyme(s) could be selected based on the components difference between Gram-Positive Bacteria and Gram-Negative Bacteria, namely, the difference of peptideglycan or of lipopolysaccharides. Two kinds or more of enzymes are particularly preferable to effectively lyse both Gram-Positive Bacteria and Gram-Negative Bacteria. It was demonstrated in the present invention that the lysis activities offered by the mixed enzymes of Lysozyme, Lysostaphin and N-acetylmuramidase were enhanced in comparison with those by the single enzyme.

Treatment temperature with enzymes on *Staphylococcus aureus* should preferably be adjusted to from about 4° C. to about 60° C., then that on *Staphylococcus epidermidis* should be adjusted to about 25° C. or more, preferably, to about 37° C. or more, and that on *Enterococcus faecalis* should be adjusted to from about 25° C. to less than about 60° C., preferably, from about 37° C. to about 42° C. Accordingly, it is most preferable to designate the temperature range of from about 37° C. to about 42° C. as the optimum treatment temperature. Further, the critical temperature range to be shared with the three bacterial species is expected to the range of from about 26° C. to about 59° C.

Then, treatment time with enzymes on any digested sample from *Staphylococcus aureus, Staphylococcus epidermidis, Enterococcus faecalis* is 20 minutes or more (both at zero minute and 10 minutes were not appropriate), then, since there was no leukocyte in the bacteria, the treatment time should be adjusted to at least about 15 minutes or more, preferably, to about 20 minutes or more, and be designated the time range of from about 30 minutes to about 60 minutes as the optimum treatment time. Treatment time of from about 15 minutes to about 120 minutes may also be applicable.

Then, N-acetylmuramidase is an enzyme which lower an absorbance at 600 nm under the reaction at 37° C. for 5 minutes of N-acetylmuramidase with heat-treated dry-powder of *Enterococcus faecalis* in 5 mmol/l Tris-HCl Buffer Solution (pH 6.0) containing 2 mmol/l magnesium chloride. Then, when 1 Unit of enzyme activity is defined as an activity to lyse one ug of heat-treated dry-powder of *Streptococcus salivarius* (IFO 3350) in one minute which was determined thereon at 37° C. and pH 7.0, the enzyme of 2,000 Units/mg or more is preferable.

Lysozyme is an enzyme which lower an absorbance at 600 nm under the reaction of *Micrococcus luteus* with Lysozyme in PBS at 37° C. for 5 minutes. Then, when 1 Unit of enzyme activity is defined as an activity to lower 0.001 of an absorbance at 540 nm in one minute which was determined on *Micrococcus luteus* at 35° C. and pH 6.2, an enzyme of 50,000 Units/mg or more is preferable.

Lysostaphin is an enzyme which lower an absorbance at 600 nm under the reaction of *Staphylococcus epidermidis* with Lysostaphin in PBS at 37° C. for 5 minutes. When 1 Unit of enzyme activity is defined as an activity to lower an absorbance at 620 nm of 0.240 to 0.125 in 10 minutes which was determined on *Staphylococcus aureus* at 37° C. and pH 7.5, an enzyme of 500 Units/mg or more is preferable.

Zymolase (Products Name: Zymolyase (SEIKAGAKU CORPORATION)) is an enzyme taken from the liquid culture medium of *Arthrobacter lutesul* and have strong degradation activities on cell walls of the active yeast cells. Essential enzymes contained in Zymolase and involved with cell wall degradation is β-1,3-glucan lanimaripentaohydrolase which acts on glucose polymer with β-1,3-bonds and produces laminaripentaose as a main product. Zymolyase-100T is purified in ammonium sulfate fractionation, then in affinity chromatography (Kitamura, K. et al., *J. Ferment. Technol.,* 60, 257, 1982) and have activity of 100,000 Units/g. However, it is well known that activities of the subjected enzyme are changed according to the kinds of yeast to be substrates, culture condition and growth phase thereof (Kitamura, K. et al., *J. Gen. Appl. Microbiol.,* 20, 323, 1974; Kitamura, K. et al., *Agric. Biol. Chem.,* 45, 1761, 1981; Kitamura, K. et al., *Agric. Biol. Chem.,* 46, 553, 1982). Zymolyase-100T contains about $1.0 \times 10^7$ Units/g of β-1,3-glucanase, about $1.7 \times 10^4$ Units/g of protease and about $6.0 \times 10^4$ Units/g of mannase, but does not contain any DNAse and RNAse (Kitamura, K. et al.; *J. Gen. Appl. Micro-biol.,* 18, 57, 1972). Then, the optimum pH of Zymolyase is from about 5.5 to about 8.5, preferably, from about 6.5 to about 7.5, while the optimum temperature thereof is from about 25° C. to about 55° C., preferably, from about 35° C. to about 45%. Further, lytic spectrum (genus) to yeast (cells in logarithmic growth phase) may includes *Ashbya, Candida, Debaryomyces, Eremothecium, Endomyces, Hansenula, Hanseniaspora, Kloekera, Kluyveromyces, Lipomyces, Helschkowia, Pichia, Pullularia, Torulopsis, Saccharomyces, Saccharomycopsis, Saccharomycodes, Schwanniomyces* or the like.

In particular, *Candida* genus may include *Candida albicans, Candida tropicalis, Candida parasilosis, Candida galacta, Candida guilliermondii, Candida krusei, Cryptococcus neoformans*. SH compounds, for example, cysteine, 2-mercapto-ethanol, dithiothreitol can be employed as an activator of these enzymes.

Bacteria belonged to these genus may also be employed in the present invention. 1 Unit of the enzyme activity is defined as an activity to lower about 30% an absorbance at 800 nm of the reaction solution (prepared by adjusting with 1 ml of sterilized-purified water to be 10 ml as their final volume containing 1 ml enzyme solution of 0.05~0.1 mg/ml, 3 ml of Brewer's Yeast Suspension (2 mg dry-weight/ml) as a substrate, and 5 ml of M/15 Phosphoric Acid Buffer Solution (pH 7.5)) in two hours which was determined on Brewer's Yeast Suspension as a substrate at about 25° C. Zymolyase-100T has an activity of 100,000 Units/g.

With regard to the concentration of PMSF (to be added to keep a form of the leukocytes by protecting them from protease) to be used as a reagent solvent, since 10 μmol/l or more of PMSF concentration was effective and a form of the leukocyte was completely kept at the PMSF concentration of 0.1 mmol/l or more, PMSF concentration should be adjusted to the range of from about 10 μmol/l to about 10 mmol/l, preferably that of from about 0.1 mmol/l to about 1 mmol/l. Similarly, DMSO concentration should also be adjusted to less than 5%, preferably 2% or less, and more preferably about 1%. Accordingly, the reagent solvent should preferably be prepared by dulting 100 to 1,000-fold, with PBS, Dimethyl Sulfoxide (DMSO) containing 0.1 mol/l Phenylmethyl Sulfonylfluoride (PMSF).

Acetylation of cell membrane proteins may further be performed after the step to bare DNA in the causative microorganisms. In particular, slides are immersed in the acetylation reagent prepared by adding Acetic Anhydrate to the acetylation raw reagent (adjusted with quantum sufficient of sterilized-purified water to be 50 ml as their total volume containing 7.46 g of Triethanolamine and quantum sufficient of Hydrochloric Acid), diluting from about two-fold to about 50-fold, preferably about 10-fold with sterilized-purified water, and adjusting final concentration of Acetic Anhydride to from 0.1% to 3.0%, preferably 0.8%, and are applied to a centrifuge for from 5 to 30 minutes. After then, they are completely air-dried by immersing them successively into 75%, 85% and 98% Ethanol for from two to five minutes respectively.

Alkalization of DNA in the causative microorganisms may further be performed to reshape it into the single strand DNA after the step to acetylate the cell membrane proteins. In particular, slides are immersed for from about two minutes to about five minutes in PBS containing from about 10 mmol/l to about 300 mmol/l Sodium Hydroxide, preferably, about 70 mmol/l Sodium Hydroxide (prepared by adding Sodium Hydroxide to PBS Raw Solution, diluting 20-fold with sterilized-purified water, and adjusting final concentration of Sodium Hydroxide to 70 mmol/l). After then, they were completely air-dried by immersing them successively into 75%, 85% and 98% Ethanol for from two to five minutes respectively.

In order to perform in situ hybridization with detective DNA probe which can hybridize under the stringent condition to the naked DNA from the causative microorganisms, probe solution (solution containing the detective DNA probe prepared with probe dilution) is applied to the area to be smeared, and is left for from about one hour to about three hours, preferably, for about two hours in the wet chamber of from about 25° C. to about 50%, preferably, from about 37° C. to about 42%.

Then, three stained bottles containing the hybridization detergent (prepared by mixing Hybridization Raw Solution (prepared with sterilized-purified water to be 75 ml as their total volume containing 13.15 g of Sodium Chloride, 6.615 g of Trisodium Citrate Dihydrate) in the ratio of Hybridization Raw Solution:sterilized-purified water:Formamide=5:45:50) are provided and they are successively immersed therein at from about 35 to about 45%, preferably, at about 42° C. for 10 minutes respectively. They are then immersed in PBS and are applied successively to centrifugation on a centrifuge for from about five to about 30 minutes. In particular, the diluted probe solution contains 600 µl of Salmon Sperm DNA, 50 µl of 100×Denhurt's Solution, 500 µl of Hybridization Raw Solution, 2250 µl of Formamide and 1000 µl of 50% Dextran Sulfate. Probe solution contains preferably 15 ng of each detective DNA probes and may be adjusted with the probe dilution to be 50 µl as their total volume.

Probe concentration of SA, SE, PA, EF, EK is adjusted to from about 0.6 ng/µl to about 1.8 ng/µl, preferably to from about 0.6 ng/µl to about 1.2 ng/µl. Since result at 0.06 ng/µl was not acceptable while result at 0.6 ng/µl was acceptable, it is preferably to adjust the concentration to at least 0.1 ng/µl or more. Then, since result at 2.4 ng/µl was not acceptable while result at 1.8 ng/µl was acceptable, it is preferably to adjust the concentration to 2.2 ng/µl or less. Further, the optimum concentration of the positive control and the negative control are adjusted to concentration of from 0.4 ng/µl to 2.0 ng/µl and from 0.6 ng/µl to 2.0 ng/µl respectively, preferably, that of from 0.6 ng/µl to 1.0 ng/µl for the both control.

Time to perform hybridization is at least 30 minutes or more, preferably 60 minutes or more, and more preferably 90 minutes or more. Time of from about 120 minutes to about 900 minutes may be designated as optimum hybridization time.

It is preferably to use surfactants like sodium dodecyl sulfate (SDS) in the step of in situ hybridization because it may allow enhancement of the detection sensitivity. SDS concentration is preferably 1% or less, more preferably from about 0.1% to about 0.5%, more further preferably about 0.25%. SDS is added to the solution to be employed at the hybridization, otherwise, it may be added in advance to the probe diluent or the probe solution.

It is recommended to employ, as the detective DNA probes, one or more kind(s) of DNA probe(s) having from about 350 to about 600 base length, preferably from about 350 to about 550 base length, because the probes are thereby smoothly incorporated into the phagocytes and they may easily and exactly be contacted with genes of the exogenous microorganisms wherein such probes are incorporated. It is not necessary to fall base length (number of bases) of the subjected within the base length range aforenoted, but is simply recommended to employ probes having base length distribution to be at least partially overlapped with the base length range aforenoted. These probes are made of single or several (one or more) kind(s) of probes. One or more probe(s) may be plural kinds of probes to be hybridized to the single bacterial species or may be plural kinds of probes to be hybridized to the plural bacterial species one to one, but any restriction would not be imposed as far as one or more kind(s) of probes is/are used.

These probes have preferably DNA fragments containing a sequence not to be hybridized anyway to phagocytes themselves and would not cross-hybridize at all to any gene from the unrelevant bacteria species. Specific probes would be prepared in a short time, for example, with a subtraction method. These probes may be prepared and labelled through the conventional nick translation methodology using non-radioisotopic labelling substances like fluorescein isothiocyanate (FITC), biotin, digoxigenin (digoxigenin(DIG)-11-dUTP) or the like. Strand length of the probes can be adjusted most effectively by changing the amount ratio of DNAseI and DNA polymerase I respectively to be added at the nick translation reaction. For example, in order to effectively label 2 µg of DNA probe (SA-24) and adjust strand length thereof (into base length of from about 350 to about 600) which allow the probes to be effectively in situ hybridized to the exogenous microorganisms DNA, in the reactionary solution of 100 µl total volume, with regard to 2 µl of 10 U/µl DNA polymerase I, 6 µl of DNAseI is presented in the 100 µl total volume as an activity of from about 10 mU to about 350 mU, preferably from about 25 mU to about 200 mU, and more preferably from about 50 mU to about 150 mU. As far as volume ratio in the essential optimum reaction conditions aforenoted is kept at the certain level, volume of each enzyme and total volume of the reactionary solution can be changed optionally. In the other words, volume of DNAseI may be adjusted, with regard to 20 U of DNA polymerase I in the total volume of 100 µl, to from about 10 mU to about 350 mU, preferably from about 25 mU to about 200 mU, and more preferably from about 50 mU to about 150 mU. Turning to the other aspect, it is recommended to perform nick translation reaction by adjusting volume of DNAseI, with regard to 1 Unit of DNA polymerase I, to from about 0.5/1,000 U to about 17.5/1,000 U, preferably from about 1.25/1,000 U to about 10/1,000 U, and more preferably from about 2.5/1,000 U to about 7.5/1,000 U. Then, with regard to 1 µg of DNA, volume of DNA polymerase I is adjusted to about 10 U, while that of DNAseI is adjusted to from about 5 mU to about 175 mU, preferably from about 12.5 mU to about 100 mU, and more preferably from about 25 mU to about 75 mU. With regard to the other probes, an amount of DNA as well as optimum reaction conditions on DNA polymerase and DNAse I are determined by referring to the optimum reaction conditions aforenoted, then the probe length (the length of from about 350 bases to about 600 bases) is also determined in which the length may allow the probes to be effectively labelled and may allow the probes to be effectively in situ hybridized to the exogenous microorganisms DNA.

Stringent condition to be employed at the in situ hybridization is a condition, for example, to incubate under the presence of formamide of from about 30% to about 60%, preferably at about 50%, at from about 30° C. to about 50° C., preferably from about 38° C. to about 42° C., and rinse successively.

After in situ hybridization, blocking operation may also be performed. In particular, 1 ml of Blocking reagent (prepared with sterilized-purified water to be 10 ml as their total volume containing 2 ml of Rabbit Normal Serum and 0.5 ml of PBS Raw Solution) per single slide is dropped onto the smeared area thereof and the slides were left for from 15 to 60 minutes. Then, Blocking reagent is removed.

In order to detect the signals resulted from hybridization with the bacterial gene (genome DNA or RNA), any coloration reaction utilizing the conventional antigen-antibody reaction or the like may be employed. Namely, the samples so hybridized are fully washed, then are subjected to Blocking, and are treated with complexes like anti-FITC antibody, anti-digoxigenin antibody, for example, alkaline phosphatase complexes, followed by evaluation on the hybridization results through signals to be expressed by the chromogenic substrates in the complexes. For example, when a probe is labelled with digoxigenin 11-dUTP as noted above, anti-digoxigenin alkaline phosphatase complexes will be employed, and the probe may be detected with a substrate (Nitro Blue Tetrazolium, 5-Bromo-4-Chloro-3-Indolyl Phosphate or the like) to be usually employed on the alkaline phosphatase. Then, the smear samples, which are washed after the coloration reaction, are subjected to counterstain with Naphthol Black, Fast Green (20 mg/50 ml, Wako Chemicals) or the like, and in-cell signals are detected by an optical microscopy.

Particularly, in order to take signals in hybridization by employing, for example, DNA probes labelled with digoxigenin as detective DNA probes, labelled antibody solution is prepared by diluting from 10 to 200-fold, preferably 50-fold the labelled antibody (prepared with 12.6 µl of Buffer A (prepared with quantum sufficient of sterilized-purified water to be 100 ml as their total volume containing 746 mg of Triethanolamine, 17.5 mg of Sodium Chloride, 20.3 mg of Magnesium Chloride Hexahydrate, 1.36 mg of Zinc Chloride, 1000 mg of Bovine Serum Albumin and quantum sufficient of Hydrochloric Acid) to be 14 µl as their total volume containing 1.05 Unit of alkaline-phosphatase-labelled anti-digoxigenin antibody solution) with the antibody dilution (prepared with quantum sufficient of sterilized-purified water to be 0.7 ml as their total volume containing 8.48 mg of Tris-(Hydroxymethyl)-Aminomethane, 6.14 mg of Sodium Chloride, and quantum sufficient of Hydrochloric Acid), then 10 µl of the labelled antibody solution is dropped onto each of the smeared area, and they may be left for from 15 to 60 minutes. After then, they are immersed in from two-fold to fifty-fold diluted solution, preferably ten-fold diluted solution of the labelled antibody detergent solution (prepared with sterilized-purified water to be 100 ml as their total volume containing 1 ml of Polysolvate 20 and 50 ml of PBS Raw Solution) and are centrifuged for from five to 30 minutes during which they are being immersed in the detergent solution. This operation is repeated twice, then the samples are immersed in the treatment solution prepared by mixing Preliminary Treatment Solution 1 (prepared with quantum sufficient of sterilized-purified water to be 50 ml as their total volume containing 6.06 g of Tris-(Hydroxymethyl)-Aminomethane, 2.92 g of Sodium Chloride, and quantum sufficient of Hydrochloric Acid) with equal amount of Preliminary Treatment Solution 2 (prepared with quantum sufficient of sterilized-purified water to be 50 ml as their total volume containing 5.08 g of Magnesium Chloride Hexahydrate), then diluting approximately 5-fold with sterilized-purified water, and are centrifuged for from five to 30 minutes during which they are being immersed in the detergent solution. 1 ml of chromogenic agent (Nitro Blue Tetrazolium (NBT)/5-Bromo-4-Chloro-3-Indolyl Phosphate (BCIP) per single slide is dropped onto the smeared area of the slides by filtrating with a disposable syringe equipped with 0.2 µm syringe top filter, and is kept in the dark and is left in a wet chamber for from about 15 minutes to about 60 minutes at from about 10° C. to about 45° C., preferably at 37° C. Then, they are immersed for from about two to about 10 minutes in the solution prepared by diluting from two-fold to about 50-fold, preferably about ten-fold the chromogenic agent cleaner (prepared with quantum sufficient of sterilized-purified water to be 50 ml as their total volume containing 606 mg of Tris-(Hydroxymethyl)-Aminomethane, quantum sufficient of Hydrochloric Acid and 186 mg of Disodium Ethylenediaminetetraacetic acid Dihydrate) and are air-dried. Further, they are immersed in the solution prepared by diluting from two-fold to 50-fold, preferably 10-fold the counterstain solution (prepared with quantum sufficient of sterilized-purified water to be 50 ml as their total volume containing 50 mg of Fast Green FCF (Edible Dye Green No. 3)) and in an acetic acid solution of from about 0.1% to about 5%, preferably about 1%. Thereafter, they may be immersed again in the solution prepared by diluting about two-fold to about 50-fold, preferably 10-fold the cleaner aforenoted to remove excessive counterstain solution and are completely air-dried. Each of such chromogenic agents may be prepared individually.

Preferable solution of the anti-digoxigenin antibodies labelled with alkaline phosphatase may include a solution which will offer color in the blotted area made by blotting one ng of DNA labelled with digoxigenin onto a blotting membrane, blocking the same, then treating those with the 10,000-fold diluted solution of the anti-digoxigenin antibody labelled with alkaline phosphatase, and reacting those with chromogenic substrates (NBT/BCIP), while it will not offer any color according to the same procedure employing DNA without digoxigenin label. Anti-digoxigenin antibodies taken from sheep are preferable. In particular, it is recommended to take such antibodies by purifying the immunized sheep serum with an ion-exchange chromatography and an antibody column chromatography.

Chromogenic agent (NBT/BCIP solution, pH 9.0-10.0) is an agent prepared preferably with quantum sufficient of sterilized-purified water to be 10 ml as their total volume containing 3.3 mg of Nitro Blue Tetrazolium (NBT), 1.65 mg of 5-Bromo-4-Chloro-3-Indolyl Phosphate (BCIP), 99 µg of N,N-dimethyl-formamide, 121 mg of Tris-(Hydroxymethyl)-Aminomethane, quantum sufficient of Hydrochloric Acid, 58.4 mg of Sodium Chloride, 101.6 mg of Magnesium Chloride Hexahydrate.

Preferable chromogenic agents may include an agent which will offer violet signals in the blotted area made by blotting proteins labelled with alkaline phosphatase onto a blotting membrane and treating the same with such chromogenic agents in the dark at room temperature.

In the counterstain above, edible dye, for example, Yellow No. 4 (Tartrazine) can be used to present more clearly contrast between signals and cells. Factors of such poor counter contrast may include similarity of the colors to be expressed, namely, between violet color offered by the substrate and blue color offered by Naphthol Black. When this methodology is applied to the present invention, it came to know that such methodology is useful at the counterstain. Any conventional methodology has never employed a food dye.

Nick translation methodology is applicable as a method to label the digoxigenin. The other methodology may include, for example, PCR Method, Random Primer Labelling Method, in vitro Transcription Labelling Method, Terminal Transferase Labelling Method or the like.

When at least one expressed violet signal(s) is/are confirmed by the optical microscopy (×1,000) on the subjected cells in the single well which is stained with the counterstain solution aforenoted, the sample may be designated as positive.

Then, Japanese Patent Nos. 2558420, 2798499, 2965543, 2965544 and 3026789 can be referred at the producing of the detective probes.

For example, in order to culture bacteria taken from working-cell-banks, the working-cell-banks (SA-24) are smeared streakily with a platinum loop, a disposable plastic loop or the like onto L-broth solid medium containing 50 µg/ml ampicillin mounted on the sterilized laboratory dishes (Screening).

After an overnight cultivation thereof, single colony so cultured is inoculated into 5 ml of L-broth medium containing 50 µg/ml ampicillin and is shaking cultured overnight at 37° C. (Precultivation).

2.5 ml of the culture solution is inoculated individually into 400 ml of the medium in a flask and is shaking cultured overnight at about 37° C. (Main Cultivation).

Then, in order to extract SA-24 plasmid DNA, the cultured solution prepared through the main cultivation are centrifugated at 4° C., in 4,000×g, for 10 minutes to collect the bacteria. Supernatant are removed, 20 ml of STE (10 mmol/l Tris-HCl (pH 8.0), 1 mmol/l Disodium Ethylenediaminetetraacetic acid (EDTA), 0.1 mmol/l Sodium Chloride) are added to the remained bacteria to resuspend the same, and they are centrifugated at 4° C., in 4,000×g, for 10 minutes to collect the bacteria. The bacteria is suspended with 5 ml of Solution-1 (50 mmol/l glucose, 25 mmol/l Tris-HCl (pH 8.0), 10 mmol/l EDTA) containing 10 mg/ml Lysozyme and is left for five minutes under the room temperature. Thereafter, 10 ml of Solution-2 (0.2 mmol/l Sodium Hydroxide, 1% Sodium Dodecyl Sulfate (SDS)) is added, then they are upset to mix, and are left for ten minutes on ice. 7.5 ml of Iced Solution-3 (3 mol/l potassium acetate (pH 4.8)) is added, then they are upset to mix, and are left for ten minutes on ice.

After centrifugation by a high speed refrigerated centrifuge at 4° C. for 30 minutes at 45,000×g, the supernatant is recovered, and left to stand to cool to room temperature. After leaving to stand, 0.6 volume of isopropanol (about 24 ml) is added thereto, mixed by inversion and left to stand at room temperature for 5 minutes or longer. After centrifugation by a high speed refrigerated centrifuge at 25° C., for 30 minutes at 28,000×g, the supernatant is discarded, and thus resulting pellet is washed with 70% ethanol and air dried. After air drying, 8 ml of TE (10 mmol/l Tris-hydrochloric acid (pH 8.0), 1 mmol/l EDTA) is added thereto to dissolve the pellet (extraction of plasmid DNA).

Next, for the purification of the plasmid DNA containing SA-24, 800 μl of 10 mg/ml ethidium bromide and 8.6 g of cesium chloride are added to the resulting plasmid DNA followed by mixing by inversion to dissolve the plasmid. The solution is placed in a centrifuge tube, which is then capped or sealed. After centrifugation at 20° C. for 5 hours at 500,000×g with a vertical rotor, a band of the plasmid DNA is fractionated using a glass syringe or an injection needle under the irradiation of an ultraviolet ray light. To the fractionated plasmid DNA solution is added an equivalent amount of TE-saturated 1-butanol followed by mixing by inversion and centrifugation at 15,000×g for 5 minutes by a high speed microcentrifuge to remove the supernatant. This operation is repeated to eliminate ethidium bromide in the plasmid DNA solution. Next, thereto is added TE to give the volume of 1.5 ml followed by desalting on a demineralization column (NAP-10). To the desalted plasmid DNA solution is added 30 μl of a 3 mol/l sodium acetate solution followed by mixing, and 3 fold amount of 99.5% ethanol is added thereto followed by mixing by inversion and leaving to stand at −20° C. for 30 minutes or longer. After leaving to stand, centrifugation is conducted with a high speed refrigerated micro centrifuge at 4° C. for 20 minutes at 15,000×g to remove the supernatant. Thereafter, cold 70% ethanol is added thereto to suspend therein, and once again, centrifugation is conducted with a high speed refrigerated micro centrifuge at 4° C. for 20 minutes at 15,000×g to remove the supernatant. Thus resulting precipitate of the plasmid DNA is evaporated to dryness under a reduced pressure. TE in an amount of 100 μl is added to the plasmid DNA to dissolve completely, and the concentration is measured on the basis of the absorbance at 260 nm (Purification of plasmid DNA containing SA-24). Then, size check of the plasmid DNA containing SA-24 is carried out by a treatment with a restriction enzyme and agarose electrophoresis.

In order to purify SA-24 by digesting the plasmid DNA containing SA-24 with restriction enzyme(s) and successively applying them to an agarose electrophoresis, 1 mg of the plasmid DNA with SA-24, molecular weight of which had been determined, are digested through a reaction to be performed at 37° C. for one and half hours or more under the presence of the restriction enzyme HindIII alone or the combination of HindIII and the other restriction enzyme(s). After digesting the plasmid DNA, completion of such digestion is confirmed by applying a part of the reactionary solution to 0.8% agarose electrophoresis. Then, after confirming such digestion, SA-24 band is taken by applying the solution to an electrophoresis with 0.8% agarose as a fractionator. SA-24 so taken are extracted from the agarose gel and are purified, then, concentration thereof is determined with an absorptiometer. A part of the purified SA-24 is applied to an electrophoresis with 0.8% agarose gel and is appeared as a single band.

SA-24 may preferably be labelled with digoxigenin with the reactionary solution having the composition listed in the following Table 1 including 2 μg of the purified SA-24.

TABLE 1

Composition in Reactionary Solution to Label

| | Amount(μL) |
|---|---|
| DNA probe | X |
| 10 × L.B.[a] | 10 |
| 100 mmol/L dithiothreitol | 10 |
| dNTPs[b] (A, G, C 0.5 mmol/L) | 4 |
| digoxigenin-dUTP[c] (0.4 mmol/L) | 5 |
| DNAseI[d] | 6 |
| 10 U/μL DNA polymerase I | 2 |
| Sterilized-Purified Water | Y |
| Total | 100 |

[REMARKS]
[a]10 × L.B.: 0.5 mol/L Tris-HCl (pH 7.5), 50 mmol/L magnesium chloride, 0.5 mg/mL bovine serum albumin
[b]dNTPs: 0.5 mmol/L 2'-dioxyadenosine-5'-triphosphate, 0.5 mmol/L 2'-dioxyguanosine-5'-triphosphate, 0.5 mmol/L 2'-dioxycytidine-5'-triphosphate
[c]digoxigenin-dUTP: 0.4 mmol/L digoxigenin-11-2'-dioxy-uridine-5'-triphosphate
[d]DNAseI: Deoxyribonuclease I is diluted with 25 mmol/L Tris-HCl (pH 7.5), 50% glycerin solution to be used at 50–150 mU per total amount of 100 μL and is adjusted to the amount aforenoted.

In Table 1, the volume X is adjustable to realize preferable probe concentration aforenoted according to the concentration of raw probe solution, then, the final volume is adjusted by determining, based on the volume X, the volume Y of Sterilized-Purified Water. After putting the labels, the reaction is terminated by adding 100 μl of TE to the reaction solution.

Free nucleotides are then removed by adding solution to terminate the reaction into the spin column and centrifuging the same at 4° C., in 380×g, for 10 minutes. Thereafter, concentration of the eluted solution is determined with an absorptiometer and is adjusted with TE to the unit level of ng/μl.

To confirm the labelled subjects, 0.5 μl of the labelled SA-24 is dropped onto a membrane and is air-dried. The membrane is immersed into the blocking reagent and is kept for 30 minutes under the room temperature. The membrane is then immersed for 30 minutes under the room temperature into the solution of anti-digoxigenin antibody labelled with alkaline phosphatase prepared by diluting 5,000-fold with a solution containing 0.1 mol/l Tris-HCl (pH 7.5) and 0.15 mol/l sodium chloride. The membrane is immersed into a solution containing 0.1 mol/l Tris-HCl (pH 7.5) and 0.15 mol/l sodium chloride, then is shaked for 10 minutes under the room temperature, and is rinsed twice. Further, the membrane is immersed for 10 minutes under the room temperature into a solution containing 0.5 mol/l Tris-HCl (pH 9.5), 0.15 mol/l sodium chloride and 50 mmol/l magnesium chloride.

The membrane is then immersed into chromogenic agent for 10 minutes, in the dark, under the room temperature. Labelled subjects are confirmed with violet color appeared under the spotted position.

Spin column is produced by filling a few amount of sterilized grass wool into 1 ml volume of disposable syringe. Sephadex G-50 swelled with 1 mmol/l Tris-HCl (pH 7.5), 1 mmol/l EDTA and 0.1% SDS is then filled into the syringe. The syringe is inserted into 15 ml volume of the disposable conical tube and is centrifuged at 4° C., in 320×g, for 10 minutes to remove the excess buffer solution. The syringe is then detached from the disposable conical tube and the excess buffer solution is discarded. Thereafter, the spin column is assembled by engaging 1.5 ml volume of Eppendolf Tube with the bottom of the disposable conical tube and entering the syringe into the conical tube.

Dot Blot Hybridization according to the following procedure is recommended to confirm specificity of the probes.

First of all, in order to denature each of the spotted genomic DNA, according to the standard procedure, 100 ng of the various bacterial genome so prepared are spotted onto nylon membranes (Pall BioDine Type B; Nihon Pall Ltd.), and air-dried membranes are kept for 10 minutes on the filter papers (3 mm: Wattman) saturated with solution containing 0.5 mol/l sodium hydroxide and 1.5 mol/l sodium chloride. The denatured DNA are then neutralized by leaving them for 10 minutes on the previously noted filter papers saturated with solution containing 0.5 mol/l Tris-HCl (pH 7.5) and 1.5 mol/l sodium chloride. They are further left for five minutes on the previously noted filter papers saturated with 2×SSC (Standard Saline Citrate) Solution and are rinsed. After then, such membranes are air-dried and are immersed into 2×SSC Solution for five minutes. In accordance with the standard procedure, the membranes are immersed into Prehybridization Solution in plastic bags and are kept at 42° C. for 60 minutes. In the plastic bag, the membranes are immersed in 15 ml of Hybridization Solution containing 400 ng of Probes and are reacted overnight at 42° C. Next, the membranes are immersed into the solution containing 2×SSC and 0.1% SDS (sodium dodecyl sulfate) and are rinced for five minutes (this is repeated twice). The membranes are then immersed into the solution containing 0.1×SSC, 0.1% SDS and are rinced for ten minutes (this is repeated three times). The membranes are immersed into 2×SSC solution and are rinced for five minutes. The membranes are immersed into the solution containing 3% bovine serum albumin, 1% Blocking Buffer (Boehringer), 0.1 mol/l Tris-Hcl (pH 7.5) and 0.15 mol/l Sodium Chloride, and are gently shaked for 30 minutes. The membranes are immersed into the solution prepared by diluting 5,000-fold the alkaline-phosphatase labelled anti-digoxigenin antibody (Boehringer) with the solution containing 0.1 mol/l Tris-HCl (pH 7.5) and 0.15 mol/l Sodium Chloride, and are gently shaked for 30 minutes. Next, the membranes are immersed into the solution containing 0.1 mol/l Tris-HCl (pH 7.5) and 0.15 mol/l sodium chloride, and are shaked for 15 minutes (twice). The membranes are immersed into the solution containing 0.1 mol/l Tris-HCl (pH 9.5), 0.1 mol/l Sodium Chloride and 5 mmol/l Magnesium Chloride, and are shaked for 5 minutes. The membranes are immersed into NBT-BCIP Solution (GIBCO BRL) and are subjected to chromogenic reaction in the dark. The membranes are then immersed into TE (10 mmol/l Tris-HCl (pH 8.0), 1 mmol/l EDTA) to terminate the chromogenic reaction and are air-dried. Particulars of Prehybridization Solution and Hybridization Solution are illustrated in the following Table 2.

TABLE 2

| | Prehybridization Solution | Hybridization Solution |
|---|---|---|
| Formamide | 7.5 | 6.75 |
| 20 × SSC Solution | 3.75 | 3.75 |
| 100 × Denhart Solution | 0.75 | 0.15 |
| 0.5 mol/L Phosphatized Buffer Solution | 0.75 | 0.6 |
| Sterized-Distillated Water | 1.5 | 1.95 |
| 10 mg/mL Salmon Sperm DNA | 0.75 | 0.3 |
| 50% Dextran Sulfate | — | 1.5 |
| Total Liquid Amount | 15.0 | 15.0 |

[Unit: ml]

Conventional surfactants can be employed as those to be used in the step of in situ hybridization. Typically, the surfactants are roughly divided into anionic surfactant, non-ionic surfactant, cationic surfactant and amphoteric surfactant.

Anion surfactants are also referred to as anionic surfactants, which yield an organic anion upon ionization in water. When a lipophilic group in the molecule of the surfactant is represented by R, examples of the anion surfactant include $RCOONa$, $RSO_3Na$, $RSO_4Na$ and the like. An aqueous solution of the surfactant containing a weakly acidic group such as $RCOONa$ is liable to be hydrolyzed and is weak alkaline. However, an aqueous solution of a surfactant having a strongly acidic group such as $RSO_3Na$, $RSO_4Na$ or the like is resistant to hydrolysis, which shall be neutral. Because it is anionic, it may lose surface activity in the presence of a large quantity of cationic substance, and may be inactivated in a strongly acidic circumstance.

Nonionic surfactants refer to those having a hydrophilic group which is nonionic. An ethylene oxide group ($—CH_2CH_2O—$) is often used as the hydrophilic group. As number of this group increases, hydrophilicity is increased. To the contrary, as number of the lipophilic group increases, lipophilicity is increased. Therefore, it is characterized in that surfactants with variously altered hydrophilicity and lipophilicity can be obtained. Because a nonionic surfactant does not ionize in water and is hardly affected by inorganic salts, less action is exerted also on a living body. In addition, the detergent action thereof is potent with comparatively less foaming, therefore, it is widely used not alone as a detergent, but in pharmaceuticals, cosmetics, foods and the like. Water soluble nonionic surfactant becomes insoluble in water at a certain temperature as the temperature rises, and then the aqueous solution starts to be turbid. Such turbidity results from the cleavage of hydrogen bonds between the hydrophilic groups and water.

Cation surfactants are also referred to as cationic surfactants, which yield an organic cation upon ionization in water. Although cation surfactants do not have potent detergent action in general, they strongly bind to anionic substances such as bacteria, leading to a great bactericidal action. Moreover, they also have an anti-static ability for fibers and plastics. Although dodecyltrimethyl chloride $[C_{12}H_{25}(CH_3)_3N]Cl$ as a typical exemplary cation surfactant is water soluble, didodecyldimethylammonium chloride $[(C_{12}H_{25})_2(CH_3)_2N]Cl$ is insoluble in water, which forms a vesicle in the form of a bimolecular film in water, and is soluble in benzene.

Ampholytic surfactants are surfactants having both an anionic group and a cationic group in the molecule. Ionization state thereof in water is similar to those of amino acids, and thus many of ampholytic surfactants are amino acid derivatives. Therefore, they have an isoelectric point similarly to amino acids, which act as an anion surfactant in an alkaline region from the isoelectric point, whilst as a cation surfactant in an acidic region. Water solubility becomes the lowest at the isoelectric point, and the surface tension is also reduced. Ampholytic surfactants are used for a bactericide, an antistatic agent or the like.

Furthermore, anion surfactants are classified into the carboxylic acid type, sulfonic acid type, sulfate ester type and phosphate ester type, whilst nonionic surfactants are classified into the ester type, ether type, ester ether type and alkanolamide type. Cation surfactants are classified into alkylamine salt type and quaternary ammonium salt type, whilst ampholytic surfactants are classified into carboxy betaine type, 2-alkylimidazoline derivative type and glycine type.

Moreover, the anion surfactants of carboxylic acid type are further classified into fatty acid monocarboxylate salts, N-acylsarcosine salts and N-acylglutamate salts. Representative examples thereof respectively include: sodium laurate and medicated soap as the fatty acid monocarboxylate salts; sodium N-lauroylsarcosine as the N-acylsarcosine salt; and disodium N-lauroylglutamate as the N-acylglutamate. Still more, the sulfonic acid type is further classified into dialkyl sulfosuccinate salts, alkane sulfonate salts, alpha-olefin sulfonate salts, straight chain alkyl benzenesulfonate salts, alkyl (branched chain) benzenesulfonate salts, alkyl naphthalenesulfonate salts, naphthalenesulfonate salts-formaldehyde condensates and N-methyl-N-acyltaurine salts. Representative examples include: sodium dioctyl sulfosuccinate as the dialkyl sulfosuccinate salt; sodium dodecane sulfonate as the alkane sulfonate; sodium straight chain dodecyl benzenesulfonate as the straight chain alkyl benzenesulfonate salt; sodium dodecyl benzenesulfonate as the alkyl (branched chain) benzenesulfonate salt; sodium butyl naphthalenesulfonate as the alkyl naphthalenesulfonate salt; and sodium N-methyl-N-stearoyltaurine as the N-methyl N-acyltaurine salt. In addition, the sulfate ester type is further classified into alkyl sulfate salts, polyoxyethylene alkyl ether sulfate salts and oil-and-fat sulfate ester salts. Representative examples include sodium dodecyl sulfate, sodium lauryl sulfate and sodium cetyl sulfate as the alkyl sulfate salt; and polyoxyethylene lauryl ether sulfate triethanolamine as the polyoxyethylene alkyl ether sulfate salt. Moreover, the phosphate ester type is further classified into alkyl phosphate salts, polyoxyethylene alkyl ether phosphate salts and polyoxyethylene alkylphenyl ether phosphate salts. Representative examples include disodium monolauryl phosphate as the alkyl phosphate salt; and sodium polyoxyethylene lauryl ether phosphate and polyoxyethylene oleyl ether phosphate (8 MOL) as the polyoxyethylene alkyl ether phosphate salt.

Ester type of the nonionic surfactants is further classified into fatty acid glycerin, fatty acid sorbitan and fatty acid sucrose ester. Representative examples respectively include: glycerin monostearate as the fatty acid glycerin; sorbitan monostearate, sorbitan trioleate, sorbitan sesquioleate, sorbitan monolaurate, polysorbate 20 (polyoxyethylene sorbitan fatty acid ester), polysorbate 60 and polysorbate 80 as the fatty acid sorbitan; and stearic acid sucrose ester as the fatty acid sucrose ester. Additionally, the ether type is further classified into polyoxyethylene alkyl ether, polyoxyethylene alkyl phenyl ether and polyoxyethylene polyoxypropylene glycol. Representative examples include: polyoxyethylene lauryl ether, polyoxyethylene stearyl ether and polyoxyethylene cetyl ether as the polyoxyethylene alkyl ether; and polyoxyethylene nonyl phenyl ether and polyoxyethylene octyl phenyl ether as the polyoxyethylene alkyl phenyl ether. In addition, the ester ether type is further classified into fatty acid polyethylene glycol and fatty acid polyoxyethylene sorbitan. Representative examples thereof respectively include oleic acid polyethylene glycol as the fatty acid polyethylene glycol; and polyoxyethylene sorbitan palmitate and polyoxyethylene sorbitan monolaurate as the fatty acid polyoxyethylene sorbitan. In addition, the alkanolamide type involves only fatty acid alkanolamide alone. Representative example is lauric diethanolamide.

The alkyl amine salt type of the cation surfactant includes monoalkyl amine salts, dialkyl amine salt and trialkyl amine salts. Representative examples thereof include monostearyl amine hydrochloride. Moreover, the quaternary ammonium salt type is further classified into alkyltrimethyl ammonium chloride (or bromide or iodide), dialkyldimethyl ammonium chloride (or bromide or iodide), and alkyl benzalkonium chloride. Representative examples respectively include: stearyltrimethyl ammonium chloride as the alkyltrimethyl ammonium chloride (or bromide or iodide); distearyldimethyl ammonium chloride as the dialkyldimethyl ammonium chloride (or bromide or iodide); and lauryl benzalkonium chloride as the alkyl benzalkonium chloride.

The carboxy betaine type of the ampholytic surfactant is only alkyl betaine alone. Representative example is lauryl betaine. Additionally, the 2-alkyl imidazoline derivative type is only 2-alkyl-N-carboxymethyl-N-hydroxyethyl imidazolinium betaine alone. Representative example includes 2-undecyl-N-carboxymethyl-N-hydroxyethyl imidazolinium betaine. In addition, the glycine type may be alkyl (or dialkyl) diethylene triaminoacetic acid, and the representative example includes dioctyl diethylene triaminoacetic acid.

Moreover, in addition to the representative examples as described above, Triton X-100, lauryl sarcosine, saponin, BRIJ35, alkyl allyl polyether alcohol, higher alcohol sulfate, N-cocoyl-L-arginine ethyl ester DL-pyrrolidone carboxylate salt, sodium N-cocoyl-N-methyl aminoethyl sulfonate, cholesterol, self emulsifying type monostearate glycerin, squalane, stearyl alcohol, stearic acid polyoxyl 40, cetyl alcohol, cetomacrogol 1000, sebacate diethyl, nonylphenoxy polyoxyethylene ethane sulfate ester ammonium, polyoxyethylene oleylamine, polyoxyethylene sorbit yellow bees wax, polyoxyl 35 castor oil, macrogol 400, N-coconut oil fatty acid acyl L-arginine ethyl-DL-pyrrolidone carboxylate salt, lauryldimethylamine oxide solution, lauromacrogol, methylcellulose, CMC (carboxymethylcellulose), polyoxyethylene hardened castor oil 20 and polyoxyethylene hardened castor oil 60, CHAPS, deoxycholic acid, digitonin, n-dodecyl maltoside, Nonidet P40, n-octyl glucoside, octyl thioglucoside, laurate sucrose, dodecyl poly(ethylene glycol ether)n,n-dodecyl-N,N-dimethyl-3-ammonio-1-propanesulfonate and the like are also included.

It is important to apply the various surfactants listed above at the in situ hybridization step, while application embodiment thereof is not limited anyway. For example, one skilled in the art would mix the surfactants previously into probe solution or probe dilution, otherwise, the skilled artisan may prepare the separate solution containing surfactants and add the same before, simultaneously or after application of the probe solution onto the area to be smeared.

If any positive control probe is necessary in the present invention, such probe may be prepared as follows. For example, in order to conduct the extraction and purification of the genomic DNA of U937 cell (ATCC CRL-1593.2), U937 cells are first cultured in a 5% carbon dioxide gas incubator at 37° C. using an RPMI1640 medium (25 ml) in a cell culture flask (175 cm$^2$). The U937 culture solution is placed in a 50 ml centrifuge tube, and centrifuged at 4° C. for 10 minutes at 220×g to recover the U937 cells. The cells are suspended and washed in 10 ml of PBS, and again centrifuged at 4° C. for 10 minutes at 180×g to recover the cells. Thereafter, the supernatant is discarded, and the cells are suspended in 1 ml of a TE solution containing 200 µg/ml proteinase K and containing 1% SDS, followed by leaving to stand at 37° C. for 30 minutes. Phenol extraction is repeated three to four times to execute deproteinization. Genome deposited through the ethanol precipitation is recovered, dissolved in 500 µl of sterile purified water containing 2.5 μg of ribonuclease, and left to stand at 42° C. for 30 minutes. The phenol extraction is repeated two to three times to execute deproteinization. Genome deposited through the ethanol precipitation is recovered, and dissolved in 500 μl of TE. Thereafter, a positive control probe can be produced by measuring the concentration with an absorbance meter, and subjecting to digoxigenin labelling. Moreover, the positive control probe which may preferably used is one which permits to ascertain the hybrid formation when the positive control probe is subjected to dot hybridization on a membrane with 100 ng of U937 genome spotted thereon. When a negative control probe is required, it can be produced by any known method.

Further, the present invention also includes a kit for detecting and/or identifying causative microorganisms of infectious diseases by taking phagocytes from the clinical specimens containing active phagocytes, immobilizing the phagocytes so taken, treating the phagocytes to improve cell membrane permeabilities thereof, further treating the phagocytes to bare DNA in the causative microorganisms which might be existed in the phagocytes, in situ hybridizing DNA so bared with detective DNA probe(s) which can hybridize with such bared DNA under stringent conditions, and detecting and/or identifying the causative microorganisms based on signals so detected, the kit comprises at least one or more enzyme selected from the group consisting of lysostafin, lysozyme, N-acetylmuramidase and zymolase used in the exposing step of the DNA, probe solution containing surfactant, and one or more DNA probe for detection. The kit includes, reagent for separating blood, enzyme pretreatment reagent, enzyme reagent, acetylation reagent, probe solution, blocking reagent, labelled antibody, labelled antibody diluent, coloring pretreatment liquid-1, coloring pretreatment liquid-2, coloring reagent, counter staining solution, PBS stock solution, hybridization stock solution, labelled antibody washing solution, coloring reagent washing solution, APS coated slide glass, probe dilution solution, buffer A and the like as demonstrated in the following Examples. Among these, it is preferred that at least the enzyme reagent and the probe solution are included. In addition, various reagents used in the present invention may be included for example, chloroform, ethanol, acetic anhydride, DMSO, PMSF, formamide, acetic acid, hydrochloric acid, sodium hydroxide and the like. Moreover, instrument and machine such as low speed centrifuge, incubator, counting chamber, shaker, humid box, incubator, light microscope, variable pipette, blood collection tube, tip, pipette, staining bottle, measuring cylinder, glass syringe, 0.2 μm syringe top filter may be included.

Furthermore, the present invention provides a process for monitoring the gene of a foreign microorganism digested by a phagocyte included in a clinical specimen which contains a phagocyte derived from a living body. Moreover, the present invention provides a process for identifying the gene of a microorganism which becomes a candidate of the causative microorganism which a causative microorganism of sepsis or a causative microorganism of bacteriemia is specified on the basis of the results identified.

It was revealed that when this process was applied in practice to diagnoses for blood of a variety of patients suspected as suffering from sepsis, causative microorganism could be detected with about four times higher sensitivity compared to the blood culture process with no influence of the administered antimicrobial agent, and the identity of the detected microorganism strain was favorable. Furthermore, in comparison with the blood culture which requires three days or longer and approximately 14 days for the examination, an accurate result can be achieved by a simple operation within a short time period, i.e., about 8 hours, until the completion of the entire operation, according to the process of the present invention, an useful marker can therefore be realized in monitoring and the like in prognosis or diagnosis of an infectious disease such as sepsis, bacteriemia or the like in which a rapid and favorable care is particularly necessary.

EXAMPLES

The present invention will be described in detail along with the following Examples, but as a matter of course would not be limited to the Examples because of the following disclosures.

Example 1

Blooding and Preparation of Blood-Specimens

Twelve blood specimens (Specimen A-L) were obtained as a clinical specimen from the patients who are under the suspicion about sepsis. 10 ml of heparinized venous bloods were obtained from each patient and were mixed with the blood components separative reagent (adjusted with sterilized-purified water to be 25 ml as their final volume containing 225 mg of Sodium Chloride and 1.5 g of Dextran (Molecular Weight: 200,000-300,000)) in the ratio of 4:1. Leukocyte fractions (the upper layer) were then obtained by leaving them at 37° C. for 30 minutes. Leukocytes were appeared by centrifuging the leukocyte fractions in 160×g, at 4° C. and for 10 minutes. Pelletized leukocytes so obtained were suspended with 1 ml of sterilized-purified water and the suspension were immediately put into an isotonic state by adding thereto excessive amounts of PBS (prepared by diluting twenty-fold with sterilized-purified water the PBS Raw Solution which have been adjusted with sterilized-purified water to be 120 ml as their final volume containing 18.24 g of Sodium Chloride, 6.012 g of Sodium Monohydrogen Phosphate Didecahydrate and 1.123 g of Sodium Dihydrogen Phosphate Dihydrate). Such suspension were then re centrifuged in 160×g, at 4° C. and for 10 minutes.

Example 2

Fixation of Leukocytes

APS coated slides were employed wherein they were made by coating 3-aminopropyltriethoxysilane (APS, SIGMA) onto the slides (JAPAN AR BROWN CO., LTD., PRODUCTS ID. S311BL). Namely, such APS coated slides were produced by putting the slides (PRODUCTS ID. S311BL) into holders, immersing them into a diluted neutral detergent to wash the same, removing the detergent well therefrom with tap water then with purified water, leaving them under the higher temperature (100° C. or more) to dry the slides, and leaving the same under the room temperature to cool the slides. After then, these slides were immersed in Acetone containing 2% APS for one minute and were immediately rinsed gently with Acetone then with sterilized-purified water. These slides were then air-dried. Such performance was repeated and includes the immersion of these slides in Acetone containing 2% APS for one minute, immediate gentle rinse of the slides with Acetone and sterilized-purified water, and air-dry of the same. Finally, the slides were dried under the temperature of 42° C. to realize the APS coated slides.

Pelletized leukocytes were prepared by centrifuging leukocyte fractions in 160×g, at 4° C. and for 10 minutes. Then, leukocyte population was determined by adding small amount of PBS to the pelletized leukocytes, suspending the same, and counting the population with a hemacytometer. Leukocytes were duly mounted on the APS coated slides by smearing 5 μl of the leukocyte suspension into each well of the slides adjusted with PBS to be cell population of $1 \times 10^5$ cells/well, realizing the extended mono-layer of the leukocytes, and completely air-drying the same. After then, they were immersed in Carnoy s fixative solution (prepared by mixing Ethanol, Chloroform and Acetic Acid in the volume ratio of 6:3:1) for 20 minutes and were immersed in 75% Ethanol solution for five minutes. Finally, they were completely air-dried.

Example 3

Treatment to Improve Permeability of Leukocyte Cell Membrane

They were immersed in PBS for 10 minutes, then in the solution prepared by diluting ten-fold a pretreatment reagent (prepared by mixing 1.25 g of Saponin, 1.25 ml t-octylphenoxy-polyethoxyethanol (specific gravity of 1.068-1.075 (20/4° C.), pH (5 w/v %) 5.5-7.5) and 25 ml PBS Raw Solution, and adjusting with sterilized-purified water to be 50 ml as their final volume), and were applied to a centrifuge for 10 minutes to accelerate their permeability.

Example 4

Treatment of Bacterial Cell Wall with Lytic Enzymes

In order to bare DNA in the causative microorganisms, an enzyme solution was prepared by adding, per single slide, 1 ml of a reagent solvent (prepared by diluting 100-fold, with PBS, Dimethyl Sulfoxide (DMSO) containing 0.1 mol/l Phenylmethyl Sulfonylfluoride (PMSF)) to an enzyme reagent (N-acetylmuramidase 1,000 Units/ml, Lysozyme 100,000 Units/ml and/or Lysostaphin 100 Units/ml) then 1 ml of which were dropped under the temperature of 37° C.-42° C. in the wet chamber onto the area where the leukocytes were smeared and were left for 30 minutes. Then, they were immersed in PBS containing 0.2 mol/l Hydrochloric Acid (prepared by adding hydrochloric acid to PBS Raw Solution, diluting 20-fold the same with sterilized-purified water and adjusting final concentration of Hydrochloric Acid to 0.2 mol/l), and were applied to a centrifuge for 10 minutes to accelerate their permeability.

Example 5

Acetylation of Cell Membrane Proteins

Slides were then immersed in the acetylation reagent prepared by adding Acetic Anhydrate to the raw acetylation reagent (adjusted with quantum sufficient of sterilized-purified water to be 50 ml as their total volume containing 7.46 g of Triethanolamine and quantum sufficient of Hydrochloric Acid), diluting 10-fold with sterilized-purified water, and adjusting final concentration of Acetic Anhydride to 0.8%, and were applied to a centrifuge for 10 minutes. After then, they were completely air-dried by immersing them successively into 75%, 85% and 98% Ethanol for three minutes respectively.

Example 6

Alkalization of Bacterial DNA

Denaturation of Double-Stranded DNA into Single-Stranded DNA

Slides were then immersed for three minutes in PBS containing 70 mmol/l Sodium Hydroxide (prepared by adding Sodium Hydroxide to PBS Raw Solution, diluting 20-fold with sterilized-purified water, and adjusting final concentration of Sodium Hydroxide to 70 mmol/l). After then, they were completely air-dried by immersing them successively into 75%, 85% and 98% Ethanol for three minutes respectively.

Example 7

Hybridization

Probe Solution (1.0 ng/µl) containing 15 ng of DNA probes labelled with digoxigenin prepared with the diluted probe solution (containing 0.25% SDS, 600 µl of Salmon Sperm DNA, 50 µl of 100×Denhurt's Solution, 500 µl of Hybridization Raw Solution, 2250 µl of Formamide and 1000 µl of 50% Dextran Sulfate) was applied to the smeared area and was left for two hours under the temperature of 37° C.-42° C. in the wet chamber. Probe Solution without SDS was employed as a control. DNA probes labelled with digoxigenin were prepared through nick translation methodology. Then, three stained bottles containing the hybridization detergent (prepared by mixing Hybridization Raw Solution (prepared with sterilized-purified water to be 75 ml as their total volume containing 13.15 g of Sodium Chloride, 6.615 g of Trisodium Citrate Dihydrate) in the ratio of Hybridization Raw Solution: sterilized-purified water:Formamide=5:45:50) were provided and they were successively immersed therein at 42° C. for 10 minutes respectively.

After then, they were centrifuged for 10 minutes during which they were being immersed in PBS. As DNA probes labelled with digoxigenin, probes from *Staphylococcus aureus* of SA-24 (SEQ ID NO: 1), SA-36 (SEQ ID NO: 2) and SA-77 (SEQ ID NO: 3) as well as those from *Staphylococcus epidermidis* of SE-22 (SEQ ID NO: 4), SE-3 (SEQ ID NO: 5) and SE-32 (SEQ ID NO: 6) (See, Japanese Patent No. 2798499) were employed. Also, as a probe from *Pseudomonas aeruginosa*, that of P2-2 (SEQ ID NO: 7) (See, Japanese Patent No. 2965544) was employed. Then, as probes from *Enterococcus faecalis*, those of EF-1 (SEQ ID NO: 8), EF-27 (SEQ ID NO: 9) and EF-7 (SEQ ID NO: 10) (See, Japanese Patent No. 2965543) were employed. Then, probes from *Escherichia coli* of EC-24 (SEQ ID NO: 11), EC-34 (SEQ ID NO: 12) and EC-39 (SEQ ID NO: 13), that from *Enterobacter cloacae* of ET-49 (SEQ ID NO: 14), and that from *Klebsiella pneumoniae* of KI-50 (SEQ ID NO: 15) (See, Japanese Patent No. 3026789) were also employed. Further, as probes from *Candida albicans*, those of CA-26 (SEQ ID NO: 16), CA-26-1 (SEQ ID NO: 17), CA-26-2 (SEQ ID NO: 18) and CA-26-3 (SEQ ID NO: 19) (See, Japanese Patent No. 2558420) were employed. The present probes were produced with the probes listed above through nick-translation methodologies.

Example 8

Blocking

After in situ hybridization, blocking operation was performed. 1 ml of Blocking reagent (prepared with sterilized-purified water to be 10 ml as their final volume containing 2 ml of Rabbit Normal Serum and 0.5 ml of PBS Raw Solution) per single slide was dropped onto the smeared area thereof and the slides were left for 30 minutes. Then, Blocking reagent was removed.

Example 9

Reaction with Labelled Antibody

Labelled antibody solution was prepared by diluting 50-fold the labelled antibody (prepared with 12.6 µl of Buffer A (prepared with quantum sufficient of sterilized-purified water to be 100 ml as their total volume containing 746 mg of Triethanolamine, 17.5 mg of Sodium Chloride, 20.3 mg of Magnesium Chloride Hexahydrate, 1.36 mg of Zinc Chloride, 1000 mg of Bovine Serum Albumin and quantum sufficient of Hydrochloric Acid) to be 14 µl as their total volume containing 1.05 Unit of alkaline-phosphatase-labelled anti-digoxigenin antibody solution) with the antibody dilution (prepared with quantum sufficient of sterilized-purified water to be 0.7 ml as their total volume containing 8.48 mg of Tris-(Hydroxymethyl)-Aminomethane, 6.14 mg of Sodium Chloride, and quantum sufficient of Hydrochloric Acid), then 10 µl of the labelled antibody solution were dropped onto each of the smeared area, and they were left for 30 minutes. After then, they were immersed in the ten-fold diluted solution of the labelled antibody detergent solution (prepared with sterilized-purified water to be 100 ml as their total volume containing 1 ml of Polysolvate 20 and 50 ml of PBS Raw Solution) and were centrifuged for 10 minutes during which they were being immersed in the detergent solution. This operation was repeated twice, then the samples were immersed in the treatment solution prepared by mixing Preliminary Treatment Solution 1 (prepared with quantum sufficient of sterilized-purified water to be 50 ml as their total volume containing 6.06 g of Tris-(Hydroxymethyl)-Aminomethane, 2.92 g of Sodium Chloride, and quantum sufficient of Hydrochloric Acid) with equal amount of Preliminary Treatment Solution 2 (prepared with quantum sufficient of sterilized-purified water to be 50 ml as their total volume containing 5.08 g of Magnesium Chloride Hexahydrate) and diluting 5-fold with sterilized-purified water. The samples were then centrifuged for 10 minutes during which they were being immersed in the treatment solution.

Example 10

Detection 1 ml of chromogenic agent (Nitro Blue Tetrazolium (NBT)/5-Bromo-4-Chloro-3-Indolyl Phosphate (BCIP) Solution, pH 9.0-10.0: prepared with quantum sufficient of sterilized-purified water to be 10 ml as their total volume containing 3.3 mg of NBT, 1.65 mg of BCIP, 99 µg of N,N-dimethyl-formamide, 121 mg of Tris-(Hydroxymethyl)-Aminomethane, quantum sufficient of Hydrochloric Acid, 58.4 mg of Sodium Chloride, 101.6 mg of Magnesium Chloride Hexahydrate) per single slide was dropped onto the smeared area of the slides by filtrating with a disposable syringe equipped with 0.2 µm syringe top filter, and was kept in the dark and was left for 30 minutes at 37° C. in a wet chamber. Then, they were immersed for five minutes in the solution prepared by diluting ten-fold the chromogenic agent cleaner (prepared with quantum sufficient of sterilized-purified water to be 50 ml as their total volume containing 606 mg of Tris-(Hydroxymethyl)-Aminomethane, quantum sufficient of Hydrochloric Acid and 186 mg of Disodium Ethylenediaminetetraacetic acid Dihydrate) and were air-dried. Further, they were immersed in the solution prepared by diluting 10-fold the counterstain solution (prepared with quantum sufficient of sterilized-purified water to be 50 ml as their total volume containing 50 mg of Fast Green FCF (Food Dye Green No. 3)) and in the 1% acetic acid solution. Thereafter, they were immersed again in the solution prepared by diluting 10-fold the cleaner aforenoted to remove excessive counterstain solution and were completely air-dried.

Example 11

Criterion

When at least one expressed violet signal(s) is/are confirmed by the optical microscopy (×1,000) on the subjected cells which were stained with the counterstain solution in single well, the sample was designated as positive. As the result of the present method, of twelve specimens, bacteria had been detected in the five specimens of Specimen A-SA (*Staphylococcus aureus*), Specimen F and G-SE (*Staphylococcus epidermidis*), Specimen J-SE and EF (*Enterococcus faecalis*), and Specimen L-SA and CA (*Candida albicans*). In the meantime, when the same specimens were subjected to the hemoculture methodologies according to the known procedures, although the identical result was confirmed in Specimen A as a detection of SA, no bacteria had been detected in any of Specimen F, G, J and L. Accordingly, it became apparent that the present method could detect those rapidly with better sensitivity in comparison with the hemoculture methodologies.

With regard to the result on Specimen A-SA, the effect offered by adding SDS to the probe dilution is shown in FIG. 1. Obviously from FIG. 1, detection sensivity on the signal could be improved remarkably with addition of 0.25% SDS. Turning to the other specimens, signals could similarly be detected clearly by adding SDS thereto. Meanwhile, the probes employed in this Example were those produced by performing nick translation on a combination of the base sequences from SA-24 (SEQ ID NO:1), SA-36 (SEQ ID NO:2) and SA-77 (SEQ ID NO:3).

Example 12

Investigation on Optimum Cell Population of Leukocytes to be Smeared and Mounted Optimum Cell Population of Leukocytes to be smeared onto the well (the circular well of 5 mm diameter) of APS coated slides had been investigated. 10 ml of heparinized healthy human bloods were collected, then, the leukocytes were obtained therefrom according to the procedures of Example 1. Leukocytes so obtained were suspended in the quantum sufficient of PBS and the leukocyte population per 1 ml was determined with a hematimeter. A serial dilution commencing at (a) $1 \times 10^8$ cells/ml and followed by (b) $5 \times 10^7$ cells/ml, (c) $1 \times 10^7$ cells/ml, (d) $5 \times 10^6$ cells/ml, (e) $1 \times 10^6$ cells/ml, (f) $5 \times 10^5$ cells/ml and (g) $1 \times 10^5$ cells/ml was prepared and 5 µl of each population were smeared onto the slides.

Figure 2:
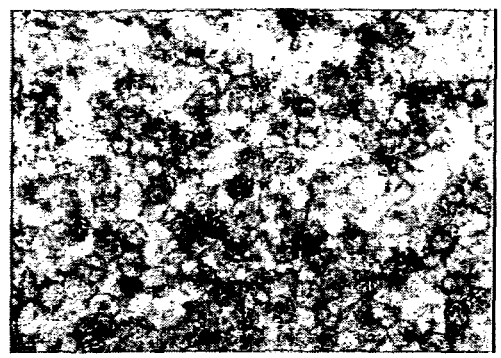
FIG. 2 is a view of illustrating a manner of leukocytes immobilized with the various cell density.
Figure 2:
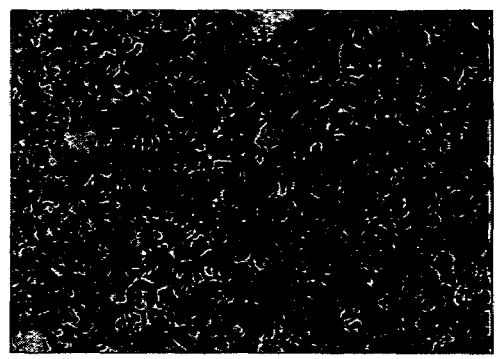
Figure 2:
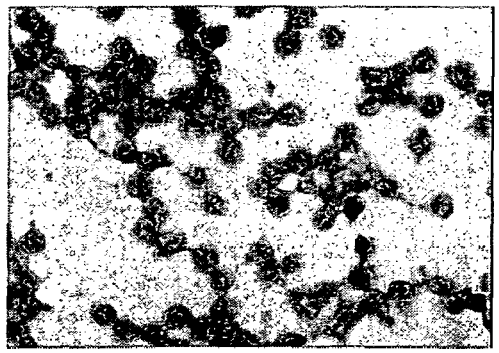
Figure 2:
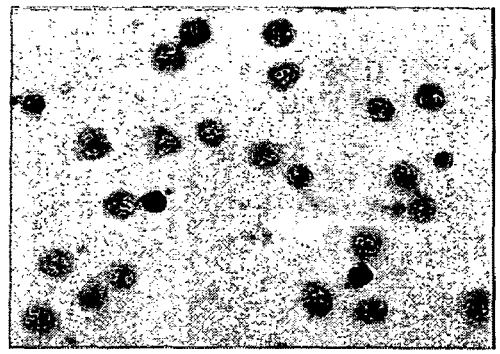
Figure 2:
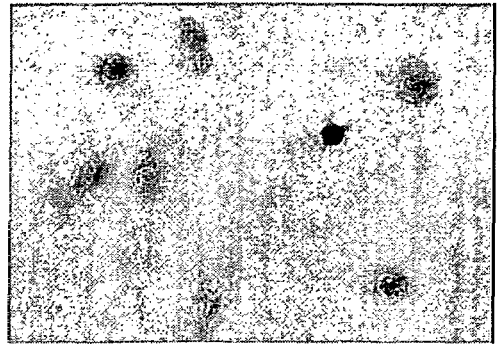
Figure 2:
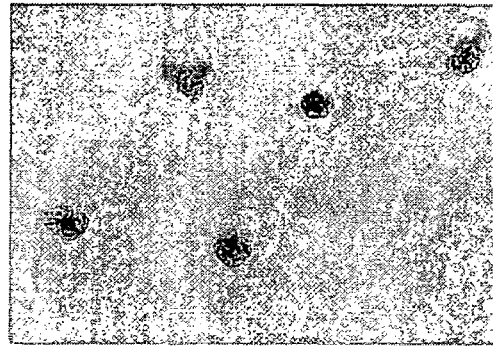

Smeared slides were air-dried and were fixed with Carnoy s fixative solution (See, Example 2). Immediately thereafter, they were stained with the counterstain solution aforenoted and were subjected to the criterion according to the method of Example 11. As a result thereof, the cell population of $1 \times 10^8$ cells/ml was too many to detect and was not appropriate. Then, the cell populations of $5 \times 10^6$ cells/ml or less were not appropriate, because little population were observed in the well. Accordingly, phagocyte density (X cells/ml) to be immobilized should be adjusted to the range of about $5 \times 10^6$ cells/ml<X cells/ml<about $1 \times 10^8$ cells/ml, preferably, to that of about $1 \times 10^7$ cells/ml≦X cells/ml≦about $5 \times 10^7$ cells/ml. It was concurrently apparent therefrom that leukocyte population (y cells/well (5 mm diameter)) to be immobilized in the single well of APS coated slides should be adjusted to the range of about 2.5×10⁴ cells/well<y cells/well (5 mm diameter)<about 5×10⁵ cells/well, preferably, about 5×10⁴ cells/well≦y cells/well (5 mm diameter)≦about 2.5×10⁵ cells/well. Experimental results on the samples (a)-(f) were illustrated in FIG. 2 (*a*)-(*f*) respectively.

Example 13

Investigation of Lytic Enzyme to be Employed

Enzymatic conditions to lyse *Staphylococcus aureus* (ATCC 12600), *Staphylococcus epidermidis* (ATCC 14990), *Pseudomonas aeruginosa* (ATCC 10145), *Enterococcus faecalis* (ATCC 19433) and *Escherichia coli* (ATCC 11775) had been investigated. Lysostaphin (Bur. J. Biochem., 38, pp. 293-300, 1973) was used as an lytic enzyme for *Staphylococcus aureus* and *Staphylococcus epidermidis*. As for *Enterococcus faecalis*, N-acetylmuramidase (Archs. Oral Biol., 23, pp. 543-549, 1978), Lysozyme (SEIKAGAKU CORPORATION) was used. Then, as for *Pseudomonas aeruginosa* and *Escherichia coli*, PBS containing 70 mmol/l sodium hydroxide was used. All of these bacteria were inoculated into 5 ml of BHI (Brain Heart Infusion) liquid medium (DIFCO) and were cultivated under 37° C. for eight hours or more. Cultivated solution were collected by centrifuging them in 2,000×g, at 4° C., for 10 minutes. Samples to be subjected were prepared by suspending the collected bacteria in PBS.

Figure 3:
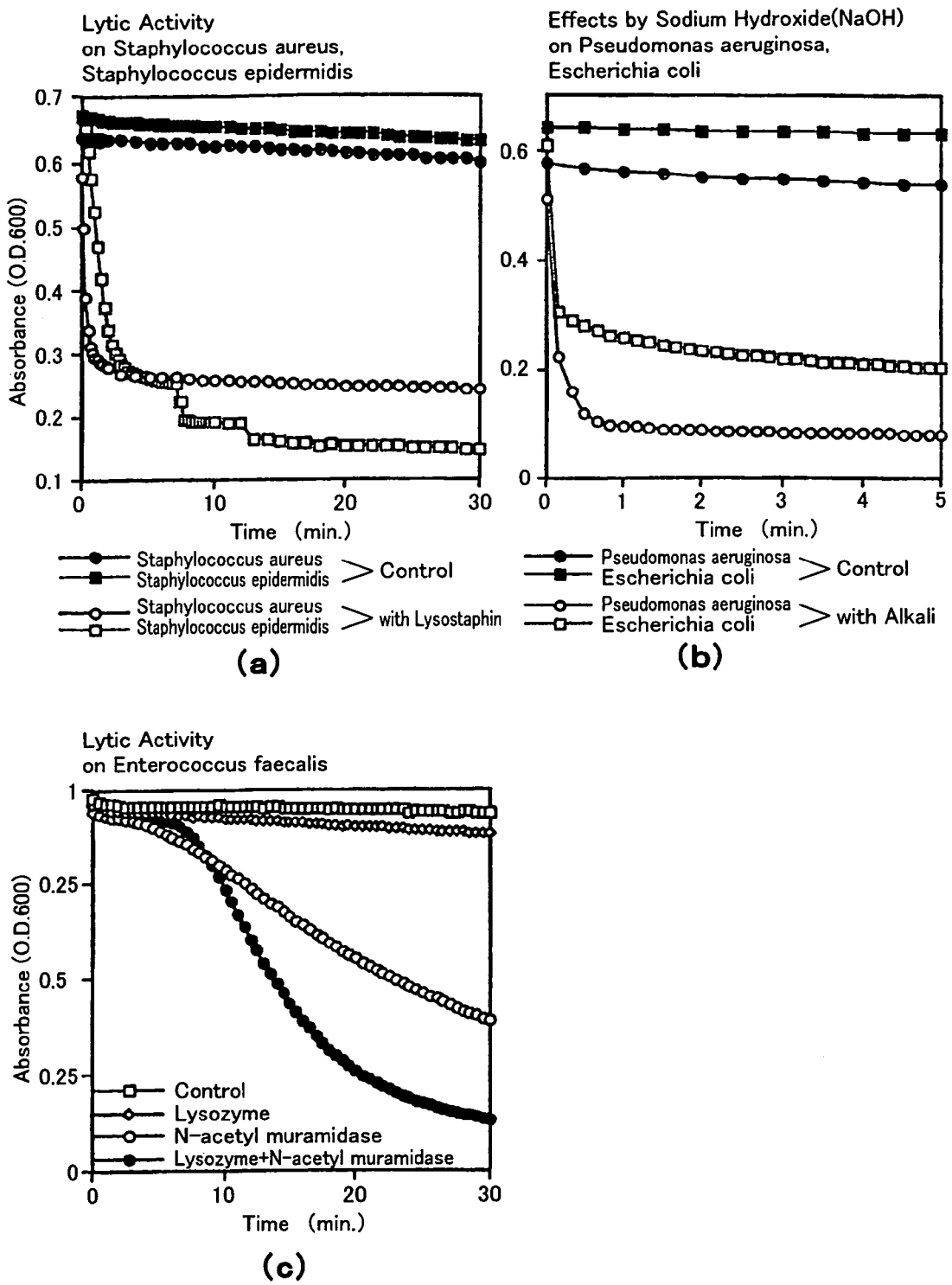
FIG. 3 is a view of illustrating a time-coursely change on lytic enzyme activity against (a) *Staphylococcus aureus* and *Staphylococcus epidermidis*, (b) *Pseudomonas aeruginosa* and *Escherichia coli*, and (c) *Enterococcus faecalis*.

Lysis activities were determined with a microplate reader by evaluating decreased density at 600 nm absorbance on the subjected sample solution. As a result thereof, *Staphylococcus aureus* and *Staphylococcus epidermidis* were lysed with Lysostaphin. As for *Pseudomonas aeruginosa* and *Escherichia coli*, enzyme treatment was not necessary, because they were lysed with PBS containing 70 mmol/l sodium hydroxide. Then, as for *Enterococcus faecalis*, it was discovered that lysis activities therefor were improved by not relying on N-acetylmuramidase alone but on the combination of N-acetylmuramidase with Lysozyme. But, for example, when *Pseudomonas aeruginosa*, *Escherichia coli* or the like are the digested bacteria with phagocytosis, such enzyme treatments may not be necessary, because their cell walls are solved at the alkaline treatment, thereby, their genes are bared. Each enzyme to be employed in the pretreatment procedure of the present invention for solving the exogenous microorganism would be valid not only for the previously noted bacteria strain, but also for the other bacterial strains including those belonged to *Staphylococcus* genus, *Streptococcus* genus, *Bacillus* genus and *Micrococcus* genus. Such enzymes can be used as an individual enzyme, but to employ them as the mixed enzymes is quite useful. These results were illustrated in FIG. 3, in particular, as FIG. 3 (*a*) *Staphylococcus aureus* and *Staphylococcus epidermidis*, (*b*) *Pseudomonas aeruginosa* and *Escherichia coli*, and (*c*) *Enterococcus faecalis*.

Example 14

Investigation of Enzyme Solution

Investigation of Optimum Concentration of DMSO

Since protease contained in the enzyme reagent degrades a form of leukocyte, enzyme activity of DMSO which is solvent of PMSF to be used to keep the form of leukocyte had been investigated. *Enterococcus faecalis* was inoculated in 50 ml of BHI liquid medium noted previously and was cultivated, at 37° C., for eight hours or more. Bacterial cells/were collected by centrifuging the cultivation liquid, at 4° C., in 2,000×g, for 10 minutes, then were suspended in PBS and were subjected to heat-treatment in an autoclave (120° C., 10 minutes). Next, these were centrifuged, at 4° C., in 2,000×g, for 10 minutes, then discarding the supernatant, and the precipitates were suspended in 1 ml of PBS and were lyophilized. The lyophilized samples were suspended in 5 mmol/l Tris-HCl (pH 6.0) containing 0-10% DMSO then 2 mmol/l Magnesium Chloride and were designated as a sample on N-acetylmuramidase. *Micrococcus luteus* (JCM1464) was inoculated in 5 ml of BHI liquid medium (supra) and was cultivated, at 37%, for eight hours or more. Bacterial cells/were collected by centrifuging the cultivated bacterial solution, at 4° C., in 2,000×g, for 10 minutes. Then the supernatant was discarded, then, bacterial cells/were collected by rinsing the bacterial pellets though suspension of them in PBS and recentrifuging the same, at 4° C., in 2,000×g, for 10 minutes. The bacteria so collected were suspended in PBS containing 0-10% DMSO and were designated as a sample on Lysozyme. On the other hand, samples on Lysostaphin were also prepared by culturing and collecting *Staphylococcus epidermidis* substantially along with the procedure for the samples on Lysozyme, and suspending the cultured bacteria with PBS containing 0%~10% DMSO.

Figure 4:
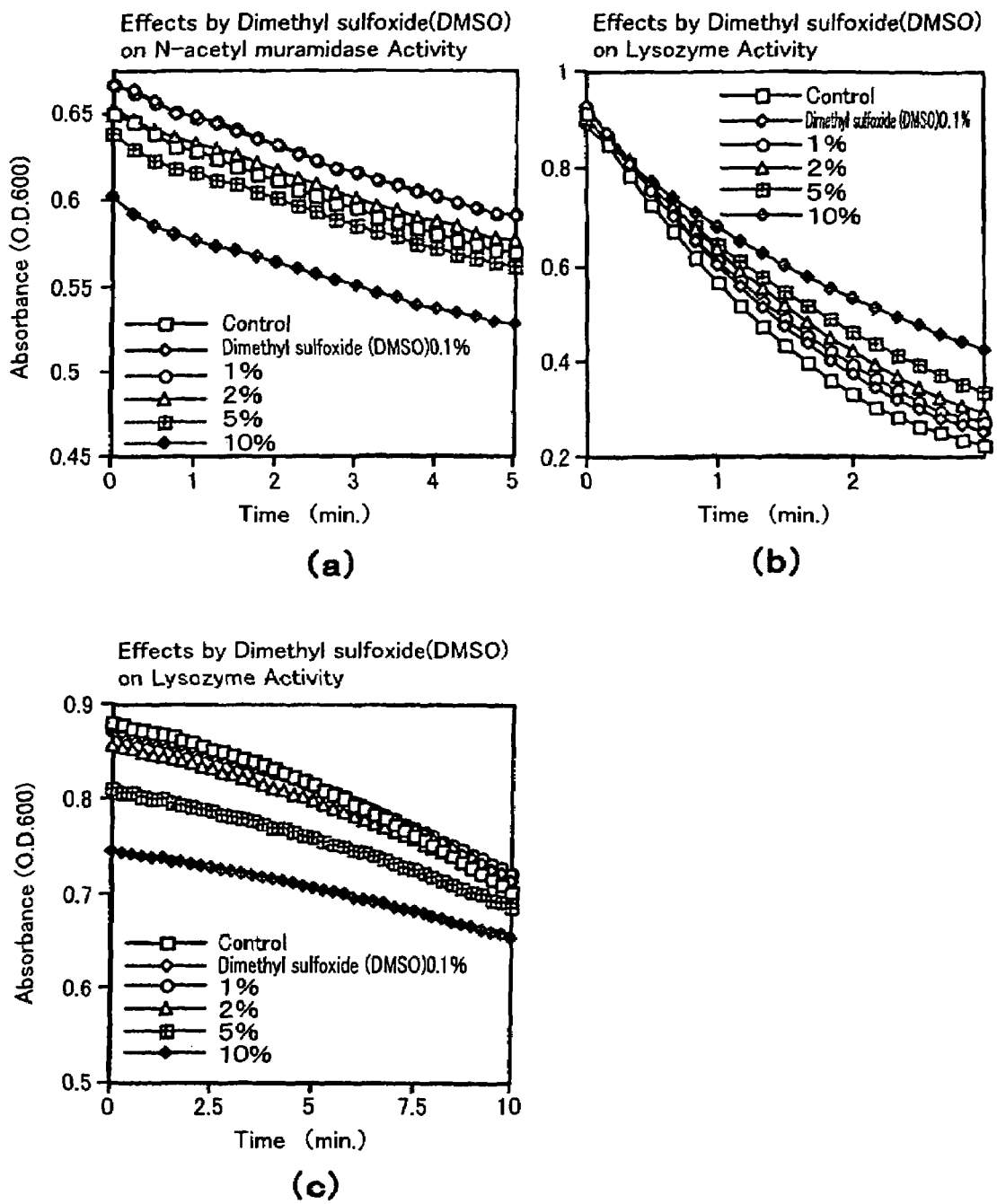
FIG. 4 is a view of illustrating concentration-dependency effects by addition of DMSO against lytic activity to be offered by (a) 300 Units/ml of N-acetylmuramidase, (b) 10,000 Units/ml of Lysozyme, and (c) 50 Units/ml of Lysostaphin.

Enzymatic activities were evaluated by determining, with a micro plate reader, decrease of absorbance at 600 nm on the subjected samples. Correlation between DMSO and the enzymatic activities were experimented in this example under the enzymatic titer of (a) N-acetylmuramidase 300 Units/ml, (b) Lysozyme 10,000 Units/ml and (c) Lysostaphin 50 Units/ml. When each enzymatic activity was evaluated with decrease of the density of bacteria suspension (O.D.=600 nm) per predetermined time, there is little correlation between DMSO and N-acetylmuramidase activity, while 5% or more of DMSO lowered activities of Lysozyme and Lysostaphin. There was no decrease on the enzymatic activities in DMSO concentration of 2% or less. Accordingly, concentration of DMSO to solve PMSF is adjusted to less that 5%, preferably 2% or less, more preferably about 1%. Results were shown in FIG. 4 (*a*)-(*c*) and in the following Table 3.

TABLE 3

Correlation between DMSO and Enzymatic Activity
(Density Decrease in Bacteria Suspension)

| Amounts of DMSO Added (%) | N-acetylmuramidase O.D./5 minutes | Lysozyme O.D./3 minutes | Lysostaphin O.D./10 minutes |
|---|---|---|---|
| 0 (control) | 79.3 ± 4.8 | 0.689 ± 0.028 | 0.168 ± 0.017 |
| 0.1 | 75.0 ± 3.2 | 0.678 ± 0.026 | 0.164 ± 0.009 |
| 1 | 75.8 ± 2.8 | 0.660 ± 0.026 | 0.160 ± 0.008 |
| 2 | 75.8 ± 2.5 | 0.653 ± 0.024 | 0.145 ± 0.009 |
| 5 | 76.3 ± 4.9 | 0.566 ± 0.017 | 0.124 ± 0.006 |
| 10 | 73.8 ± 3.5 | 0.464 ± 0.016 | 0.094 ± 0.006 |

Example 15

Examination on Enzymatic Lysis Solution

Examination on Optimal Concentration of PMSF

Figure 5:
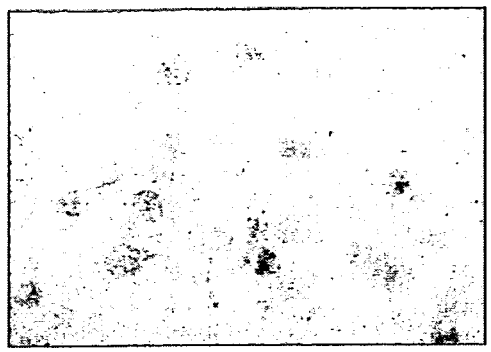
FIG. 5 is a view of illustrating results on addition of (a) protease 0.2 Units/ml only, (b) PMSF 1 μmol/ml, (c) PMSF 10 μmol/ml, (d) PMSF 0.1 mmol/ml, and (e) PMSF 1 mmol/ml to study effects of PMSF to be used to suppress the function of protease which changes a morphological form of leukocyte.
Figure 5:
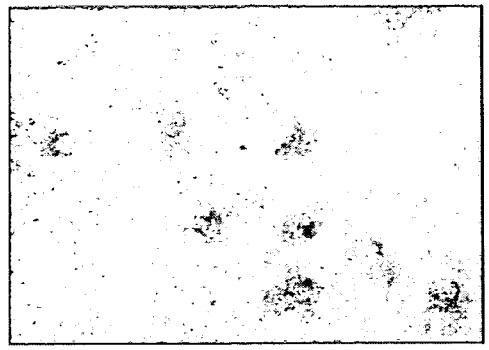
Figure 5:
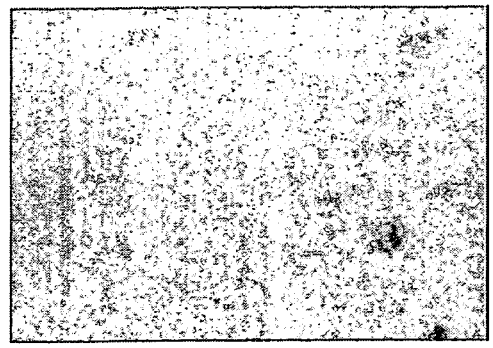
Figure 5:
Figure 5:

Because protease included in the enzyme reagent deteriorates the morphology of leukocytes, effects of PMSF (manufactured by PIERCE), which is added for the purpose of retaining the morphology of the leukocytes, on enzymatic activity were examined. PMSF was dissolved in 100 μl of DMSO (manufactured by Wako Pure Chemical Industries, Ltd), and diluted to 10 ml with PBS such that the final concentration of PMSF becomes none (0 mmol/l) to 1 mmol/l. To this solution was added proteinase K (manufactured by Boeringer Mannheim) such that titer of the protease becomes 0.2 unit/ml. Heparinized healthy human blood in an amount of 5 ml was collected, and leukocytes were obtained according to the process described in Example 1. Next, the leukocytes were suspended in an appropriate amount of PBS, and the cell number was measured using a counting chamber. Cell number was adjusted to about $5 \times 10^4$ cells/well to about $2.5 \times 10^5$ cells/well, and 5 µl therefrom was smeared on the well of the APS coated slide glass. After air drying, fixation was executed according to the method of Carnoy fixation described in Example 2. Using this sample, tests were performed according to the process described in Examples 3 to 11. As a consequence of performing the tests at the concentration of PMSF of 1 µmol/l to 1 mmol/l, effects were found at the concentration of 10 µmol/l or greater, while deterioration of morphology of the leukocytes was completely suppressed at the concentration of PMSF of 0.1 mmol/l or greater. The results are shown in FIG. 5, for (a): protease 0.2 unit/ml alone, (b): 1 µmol/ml PMSF added, (c): 10 µmol/ml PMSF added, (d): 0.1 mmol/ml PMSF added, and (e): 1 mmol/ml PMSF added, respectively.

Example 16

Examination of Optimal Titer of Lytic Enzyme, Zymolase

Optimal titer of zymolase for exposing DNA was examined through lysis of *Candida albicans*. *Candida albicans* was inoculated in YPD medium, and cultured over day and night at 30° C. Then, two types of the solutions were prepared: a solution of *Candida albicans* as a substrate suspended in PBS (substrate 1); and a solution prepared by Carnoy s fixation, immersing in 70% ethanol, air drying and suspension in PBS (substrate 2). Upon the reaction, a mixture of zymolase/PBS: 0.5 ml, substrate: 1.5 ml, M/15 phosphate buffer: 2.5 ml and sterile purified water: 0.5 ml, adjusted to give the total volume of 5.0 ml was used.

Thereafter, the reaction was allowed at 37° C. for 2 hours, and the $OD_{800}$ was measured. Furthermore, the concentration of zymolase (Zymolyase-100T) for use was 0 mg/ml, 0.01 mg/ml, 0.025 mg/ml, 0.05 mg/ml, 0.1 mg/ml, 0.25 mg/ml, 0.5 mg/ml, 1 mg/ml, 2.5 mg/ml and 5 mg/ml. Consequently, each $OD_{800}$ value when the substrate 1 was used was 0.533, 0.521, 0.553, 0.554, 0.548, 0.417, 0.394, 0.288, 0.163 and 0.113, and each $OD_{800}$ value when the substrate 2 was used was 0.445, 0.411, 0.359, 0.282, 0.232, 0.146, 0.115, 0.096, 0.08 and 0.057. It was proven that effectiveness was brought when both of the substrate 1 and substrate 2 were in the range of 0.5 mg/ml to 5 mg/ml, and particularly 1 mg/ml to 5 mg/ml. That is, the amount of zymolase to be used is preferably 50 unit/ml to 500 unit/ml, particularly 100 unit/ml to 500 unit/ml.

Example 17

Examination of Optimal Condition (Titer) of Enzymatic Treatment (1) Production of Digested Sample

[1] Preparation of U937 Cell

U937 cells (monocyte established cell line: ATCC CRL-1593.2) were cultured in an RPMI 1640 medium (25 ml) within a cell culture flask (175 cm²) in a 5% carbon dioxide gas incubator at 37° C. Next, the U937 cell culture liquid was placed in a 50 ml centrifuge tube, and centrifuged at 4° C. for 10 minutes at 220×g to recover the U937 cells. Then, thus recovered U937 cells were suspended in 200 µl of PBS, and the cell number was counted with a counting chamber. The cell number was adjusted to $1 \times 10^4$ cells/µl to $2 \times 10^4$ cells/µl.

[2] Preparation of Bacterial Digested Sample

*Staphylococcus aureus* (ATCC 12600), *Staphylococcus epidermidis* (ATCC 14990), *Pseudomonas aeruginosa* (ATCC 10145), *Enterococcus faecalis* (ATCC 19433) and *Escherichia coli* (ATCC 11775) were inoculated in each 5 ml of BHI culture medium, and cultured at 37° C. for 8 hours or longer. The cultured bacterial liquid was centrifuged at 4° C. for 10 minutes at 2,000×g to collect the bacteria. After discarding the supernatant, the bacterial pellet was suspended in 5 ml of PBS, and centrifugation was conducted once again at 4° C. for 10 minutes at 2,000×g to collect the bacteria. Thus collected bacteria were suspended in 5 ml of PBS and thereafter, 15 ml of bacterial liquids was produced prepared by diluting in PBS to give the turbidity (O.D.=600 nm) of the bacterial liquid, which was measured with a absorbance meter, of 0.01 to 0.03 for *Staphylococcus aureus*, 0.01 to 0.03 for *Staphylococcus epidermidis*, 0.02 to 0.03 for *Pseudomonas aeruginosa*, 0.01 to 0.03 for *Enterococcus faecalis*, 0.02 to 0.03 for *Escherichia coli*, respectively. Thus produced bacterial liquid was transferred into a separate 175 cm² flask for culture, and left to stand still at room temperature for 30 minutes. Fifty ml of heparinized healthy human blood was collected, and thereto was added the reagent for separating haemocyte at a ratio of 4:1, and left to stand still at 37° C. for 30 minutes to yield the leukocyte fraction. Thus obtained leukocyte fraction was adjusted to 50 ml with PBS. The supernatant in the culture flask (supra) was gently discarded, and each 10 ml of the leukocyte fraction diluted in PBS was added to the flask followed by leaving to stand still at room temperature for 10 minutes. The supernatant in the flask for culture was discarded, and the leukocytes attached to the bottom of the flask were recovered in a 15 ml centrifuge tube with 10 ml of PBS containing 0.02% EDTA, and centrifuged at 4° C. for 10 minutes at 140×g to 180×g to collect the leukocytes. Because contamination of erythrocytes was found in the collected leukocytes, precipitates of the leukocytes were gently suspended in 1 ml of sterile purified water to allow hemolysis, subjected to isotonization through adding 14 ml of PBS, followed by centrifugation once again at 4° C. for 10 minutes at 140×g to 180×g to collect the leukocytes. The collected leukocytes were suspended in PBS, and cell number was counted with a counting chamber to adjust to give $1 \times 10^4$ cells/µl to $5 \times 10^4$ cells/µl. These digested samples were referred to as SA digested sample, SE digested sample, PA digested sample, EF digested sample and EK digested sample.

[3] Smear and Fixation

Each 5 µl of U937 cells prepared in Example 17 (1) [1] and each 5 µl of each bacterial digested sample produced in Example 17 (1) [2] were smeared on each well of the APS coated slide glass, and air dried. Next, after immersing the slide glass in the Carnoy s fixative described in Example 2 for 20 minutes, it was immersed in 75% ethanol for 5 minutes. After washing Carnoy's fixative and air drying, the slide glass was stored at 4° C. until use in the test (see, Example 2). Next, pretreatment of the fixed sample was carried out according to Example 3.

(2) Standard and Process for Testing Digested Sample

[1] Cell Number

Cell number to be smeared and fixed on the slide glass of each bacterial digested sample was $5.0 \times 10^4$ to $2.5 \times 10^5$ cells/well, whilst cell number of U937 cells was $5.0 \times 10^4$ to $1.0 \times 10^5$ cells/well.

[2] Phagocytosis Rate

Figure 6:
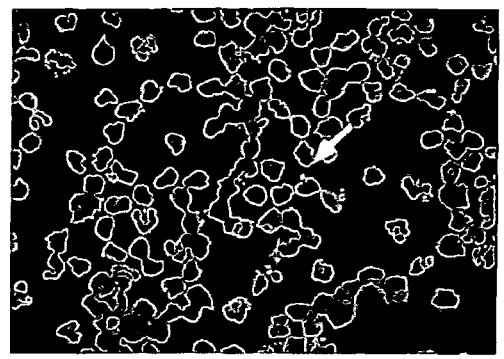
FIG. 6 is a view of illustrating that, in the phagocytosis samples prepared according to the present invention, phagocytes digested bacteria and morphological forms of such digested bacteria were changed.
Figure 6:
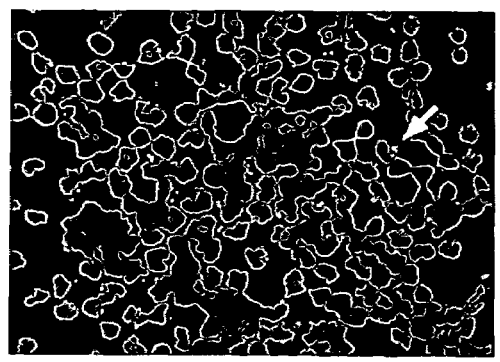
Figure 6:
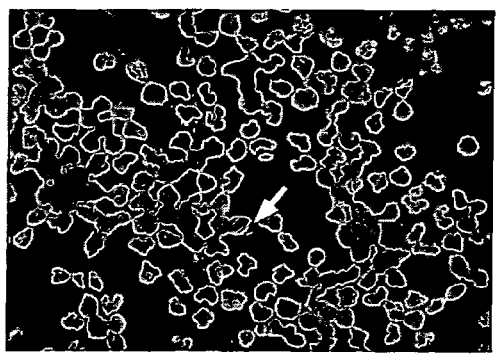
Figure 6:
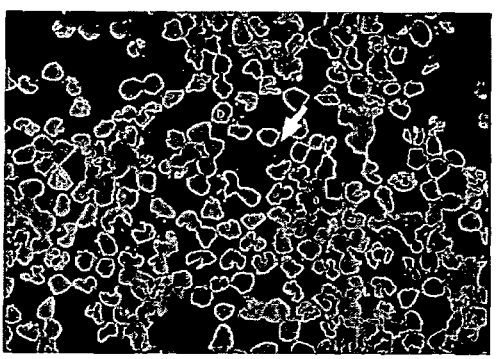
Figure 6:
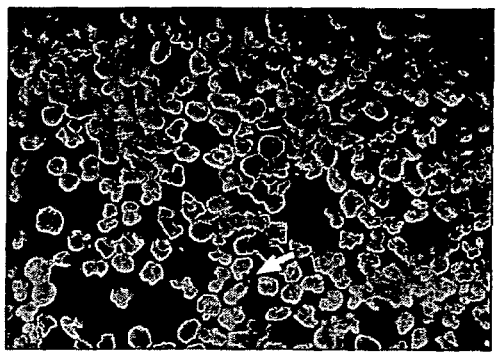

The bacterial digested sample smeared and fixed on the slide glass was stained with an acridine orange staining solution, and about 200 cells were randomly counted with a fluorescence microscope ($\times 1,000$). Among the measured cells, cells including bacteria phagocytized within the cells (cells with any change characteristic in phagocytosis found in morphology, as shown by arrows in FIG. 6) were determined as positive cells, and the phagocytosis rate (%) was calculated according to the mathematical formula below.

Phagocytosis rate (%)=[(Positive cell number/Measured cell number)$\times 100$]

Thus calculated phagocytosis rate (%) of each bacterial digested sample was 10% or greater.

[3] Test Process

The digested sample produced in Example 17 (2) [1] and [2] was employed as a specimen. The SA digested sample used had the phagocytosis rate of 23% with $1.98 \times 10^5$ cells/well. The SE digested sample had the phagocytosis rate of 27% with $1.74 \times 10^5$ cells/well. Moreover, the EF digested sample had the phagocytosis rate of 34% with $6.40 \times 10^4$ cells/well.

Using the slide glass having each digested sample smeared thereon, the enzymatic pretreatment was performed according to the process described in Example 3. Next, the slide glass after completing the enzymatic pretreatment was placed in a humid box, and the reaction was allowed by dropping 1 ml of each enzyme solution prepared to give each titer on the smeared site of the specimen. Thereafter, the slide glass was immersed in PBS containing 0.2 mol/l hydrochloric acid, and in 70% ethanol respectively, for 10 minutes, and air dried. After immersing this slide glass in PBS containing 70 mmol/l sodium hydroxide for 3 minutes, and in 70% ethanol for 10 minutes, it was air dried and stained with 1% acridine orange staining solution. Then, evaluation was made with a fluorescence microscope (X 1,000). For *Staphylococcus aureus* and *Staphylococcus epidermidis*, examination of the optimal titer was conducted with lysostafin. In order to examine the optimal titer when N-acetylmuramidase and lysozyme are used in combination for *Enterococcus faecalis*, examination on optimal titer of lysozyme was conducted in cases where N-acetylmuramidase was fixed at 100 unit/ml, and on optimal titer of N-acetylmuramidase in cases where lysozyme was fixed at 10,000 unit/ml. The determination was made as adequate when no bacterial body was identified in the leukocytes by the enzymatic treatment.

[4] Results

Figure 7:
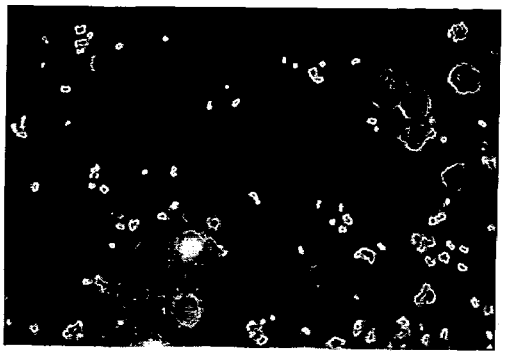
FIG. 7 is a view of illustrating effects of enzyme-treatment in the phagocytosis samples and manner of the phagocytosis samples containing (a) *Staphylococcus aureus* prior to the treatment, (b) *Enterococcus faecalis* prior to the treatment, (c) *Staphylococcus aureus* of (a) with the treatment, and (d) *Enterococcus faecalis* of (b) with the treatment.
Figure 7:
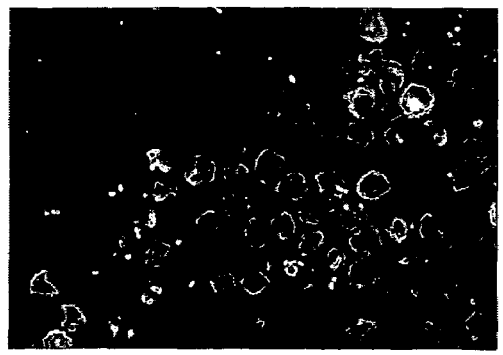
Figure 7:
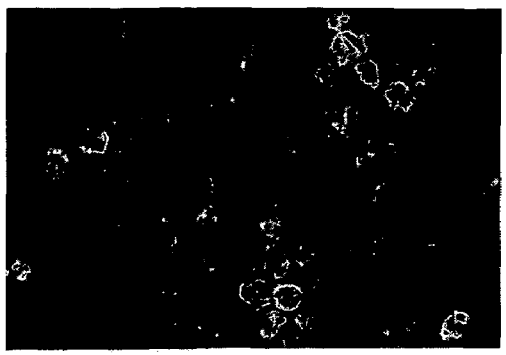
Figure 7:
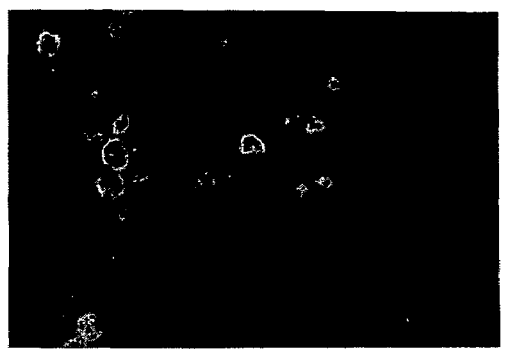

For the lysis of *Staphylococcus aureus*, as described in Table 4, sufficient effects were exerted at the titer of lysostafin of 1 unit/ml, however, upon lysis of *Staphylococcus epidermidis*, the titer of lysostafin of 10 unit/ml or greater was necessary. Therefore, the optimal titer of lysostafin was set to be 10 unit/ml to 100 unit/ml. In addition, for the lysis of *Enterococcus faecalis*, lysis did not occur with the titer of N-acetylmuramidase of 10 unit/ml or less when the titer of lysozyme was fixed at 10,000 unit/ml. In respect of lysozyme, when the titer of N-acetylmuramidase was fixed at 100 unit/ml, lysis did not occur with the titer of lysozyme of 1,000 unit/ml or less, as described in Table 5. Therefore, the optimal titer of N-acetylmuramidase was set to be 100 unit/ml to 1,000 unit/ml, whilst the optimal titer of lysozyme was set to be 10,000 unit/ml to 100,000 unit/ml. The results are shown in FIG. 7. In the Figure, depicted are states of: (a) the digested sample of *Staphylococcus aureus* prior to the enzymatic treatment, (b) the digested sample of *Enterococcus faecalis* prior to the enzymatic treatment, (c) the sample (a) following the enzymatic treatment, and (d) the sample (b) following the enzymatic treatment.

TABLE 4

Optimal Titer for Enzymatic Treatment of Lysostafin on *S. Aureus*, *S. epidermidis*

| (U/mL) Digested Samples | | Lysostafin Titer | | | | | |
|---|---|---|---|---|---|---|---|
| | | 0 | 0.1 | 1 | 10 | 100 | 1,000 |
| SA | once | inadequate | Inadequate | adequate | adequate | adequate | adequate |
| Digested | twice | inadequate | inadequate | adequate | adequate | adequate | adequate |
| Sample | thrice | inadequate | inadequate | adequate | adequate | adequate | adequate |
| SE | once | inadequate | inadequate | inadequate | adequate | adequate | adequate |
| Digested | twice | inadequate | inadequate | inadequate | adequate | adequate | adequate |
| Sample | thrice | inadequate | inadequate | inadequate | adequate | adequate | adequate |

TABLE 5

Optimal Titer of Enzymatic Treatment
of N-acetylmuramidase and lysozyme on E. faecalis

| titer (U/mL) Digested Sample | | N-acetyl muramidase | | | | | |
|---|---|---|---|---|---|---|---|
| | | 0 | 1 | 10 | 100 | 1,000 | 10,000 |
| EF | once | Inadequate | inadequate | inadequate | adequate | adequate | adequate |
| Digested | twice | Inadequate | inadequate | inadequate | adequate | adequate | adequate |
| Sample | thrice | Inadequate | inadequate | inadequate | adequate | adequate | adequate |

| (U/mL) Digested Sample | | Lysozyme titer | | | | | |
|---|---|---|---|---|---|---|---|
| | | 0 | 10 | 100 | 1,000 | 10,000 | 100,000 |
| EF | once | Inadequate | inadequate | inadequate | inadequate | adequate | adequate |
| Digested | twice | Inadequate | inadequate | inadequate | inadequate | adequate | adequate |
| Sample | thrice | Inadequate | inadequate | inadequate | inadequate | adequate | adequate |

Applications of these results obtained using the digested samples to the present invention could result in similar results. Therefore, the optimal titer of each enzyme as described above in the identification of a causative microorganism of an infectious disease in the clinical specimen of the present invention was also set similarly.

Example 18

Examination on Optimal Condition of Enzymatic Treatment (Temperature)

Using a slide glass including each digested sample smeared thereon, examination was conducted according to the process described in example 17 (2) [3]. Time period of the enzymatic treatment in this test was 30 minutes, and the temperature for examination was 4° C., 25° C., 37° C., 42° C., and 60° C. Moreover, titer of each enzyme was N-acetylmuramidase (100 unit/ml, manufactured by Seikagaku Corporation), lysozyme (10,000 unit/ml, manufactured by Seikagaku Corporation), lysostafin (10 unit/ml, manufactured by SIGMA).

Determination was conducted according to the process described in example 17 (2) [3]. As a consequence, for *Staphylococcus aureus*, no bacterial body was found in the leukocytes in the range of temperature of 4° C. to 60° C. For *Staphylococcus epidermidis*, although bacterial bodies remained in the leukocytes at the temperature of 4° C. and 25° C., no bacterial body was found at 37° C. or higher. Further, for *Enterococcus faecalis*, although bacterial bodies remained at the temperature of treatment of 4° C., 25° C. and 60° C., no bacterial body was found at 37° C. and 42° C. Hence, the optimal temperature for the enzymatic treatment was set to be 37° C. to 42° C. The results are shown in Table 6.

TABLE 6

Optimal Temperature for Treatment of Enzyme Reagent

| Digested Samples | | Temperature for Treatment (° C.) | | | | |
|---|---|---|---|---|---|---|
| | | 4 | 25 | 37 | 42 | 60 |
| SA | Once | adequate | adequate | adequate | adequate | adequate |
| Digested | twice | adequate | adequate | adequate | adequate | adequate |
| Sample | thrice | adequate | adequate | adequate | adequate | adequate |
| SE | once | inadequate | inadequate | adequate | adequate | adequate |
| Digested | twice | inadequate | inadequate | adequate | adequate | adequate |
| Sample | thrice | inadequate | inadequate | adequate | adequate | adequate |
| EF | once | inadequate | inadequate | adequate | adequate | inadequate |
| Digested | twice | inadequate | inadequate | adequate | adequate | inadequate |
| Sample | thrice | inadequate | inadequate | adequate | adequate | inadequate |

Applications of these results obtained using the digested samples to the present invention could result in similar results. Therefore, the optimal temperature of the enzymatic treatment in the identification of a causative microorganism of an infectious disease in the clinical specimen of the present invention was also set similarly.

Example 19

Examination on Optimal Condition of Enzymatic Treatment (Time)

Digested samples produced according to the process described in Example 17 (1) [1] and [2] were used as specimens. Time period of the examination was 0 minute, 10 minutes, 20 minutes, 30 minutes, 60 minutes and 120 minutes. Phagocytosis rate of the used SA digested sample was 18% with $7.80 \times 10^4$ cells/well. Phagocytosis rate of the used SE digested sample was 34% with $1.10 \times 10^5$ cells/well. Further, phagocytosis rate of the EF digested sample was 28% with $1.30 \times 10^5$ cells/well.

Using the slide glass including each digested sample smeared thereon, examination was conducted according to the process described in example 17 (2) [3]. Temperature for the enzymatic treatment in this test was 37° C., and titer of each enzyme was 100 unit/ml for N-acetylmuramidase, 10,000 unit/ml for lysozyme, 10 unit/ml for lysostafin. Determination was conducted according to the process described in example 17 (2) [3]. As a consequence, for all of *Staphylococcus aureus, Staphylococcus epidermidis* and *Enterococcus faecalis* digested samples, no bacterial body was found in the leukocytes with the time period of the enzymatic treatment of 20 minutes or longer (inadequate at 0 minute and 10 minutes). Therefore, the optimal time period of the enzymatic treatment is at least 15 minutes or longer, preferably 20 minutes or longer, and still preferably 30 minutes to 60 minutes. The results are shown in Table 7.

which affects the hybridizing velocity. When the probe concentration is too low, the reaction velocity may be lowered, leading to the possibility of unclear signal. Furthermore, use of an excess amount of probe may result in grounds for nonspecific reaction.

Figure 8:
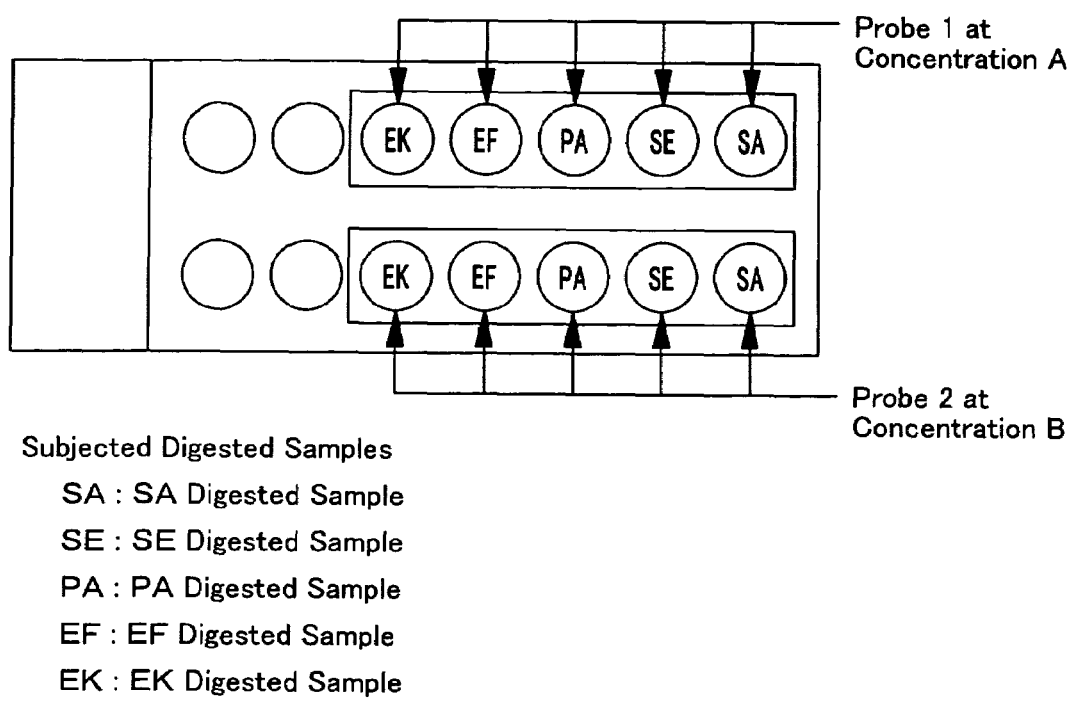
FIG. 8 is a schematic view of the slide on which the phagocytosis samples were smeared to study optimum probe concentration under the in situ hybridization.

Thus, optimal concentration was examined in connection with various probe solutions. First, the digested samples produced according to the process described in Example 17(1) [1] and [2] were used as specimens. The phagocytosis rate of the used SA digested sample was 24% with $1.48 \times 10^5$ cells/well. The phagocytosis rate of the SE digested sample was 28% with $2.07 \times 10^5$ cells/well. The phagocytosis rate of the PA digested sample was 11% with $1.59 \times 10^5$ cells/well. In addition, the phagocytosis rate of the EF digested sample was 24% with $1.72 \times 10^5$ cells/well. The phagocytosis rate of the EK digested sample was 12% with $1.63 \times 10^5$ cells/well. Using the slide glass including each digested sample smeared thereon, examination was conducted according to the process described in Example 17(2) [3]. The probes for use were labelled with digoxigenin, and the concentration of each probe for *Staphylococcus aureus, Staphylococcus epidermidis, Enterococcus faecalis, Pseudomonas aeruginosa* and *Escherichia coli* was adjusted to 0.06 ng/μl, 0.6 ng/μl, 1.2 ng/μl, 1.8 ng/μl, 2.4 ng/μl, 3 ng/μl, respectively. The probe solution prepared to each concentration described above was used on the slide glass including the digested sample smeared thereon (see, FIG. 8), and examined according to the process described in Examples 3-11.

Consequently, the signal became unclear at lower concentration (0.06 ng/μl), and on the other hand, increase in background was observed at higher concentration (2.4 ng/μl and 3 ng/μl). Therefore, the concentrations of probes of SA, SE, PA, EF and EK were determined to be 0.6 to 1.8 ng/μl, preferably 0.6 to 1.2 ng/μl. Moreover, since an inadequate result was yielded at 0.06 ng/μl, while an adequate result was yielded at 0.6 ng/μl, it is preferably determined to be 0.1 ng/μl or greater.

TABLE 7

Optimal Time Period of Treatment of Enzyme Reagent

| Digested Samples | | Time of enzyme-treatment (minutes) | | | | | |
|---|---|---|---|---|---|---|---|
| | | 0 | 10 | 20 | 30 | 60 | 120 |
| SA Digested Sample | once | inadequate | inadequate | adequate | adequate | adequate | adequate |
| | twice | inadequate | inadequate | adequate | adequate | adequate | adequate |
| | thrice | inadequate | inadequate | adequate | adequate | adequate | adequate |
| SE Digested Sample | once | inadequate | inadequate | adequate | adequate | adequate | adequate |
| | twice | inadequate | inadequate | adequate | adequate | adequate | adequate |
| | thrice | inadequate | inadequate | adequate | adequate | adequate | adequate |
| EF Digested Sample | once | inadequate | inadequate | adequate | adequate | adequate | adequate |
| | twice | inadequate | inadequate | adequate | adequate | adequate | adequate |
| | thrice | inadequate | inadequate | adequate | adequate | adequate | adequate |

Applications of these results obtained using the digested samples to the present invention could result in similar results. Therefore, the optimal time period of the enzymatic treatment in the identification of a causative microorganism of an infectious disease in the clinical specimen of the present invention was also set similarly.

Example 20

Examination on Optimal Condition of Enzymatic Treatment (Time)

In in situ hybridization reaction according to the present invention, concentration of the probe is an important factor Furthermore, since an inadequate result was yielded at 2.4 ng/μl, and an adequate result was yielded at 1.8 ng/μl, it is preferably determined to be 2.2 ng/μl or less. The results are shown in Tables 8-12 below.

TABLE 8

SA probe

| | Probe concentration (ng/μL) | | | | | |
|---|---|---|---|---|---|---|
| Digested sample | 0.06 | 0.6 | 1.2 | 1.8 | 2.4 | 3 |
| SA digested sample | − | + | + | + | + | + |
| SE digested sample | − | − | − | − | + | + |

TABLE 8-continued

SA probe

| Digested sample | Probe concentration (ng/μL) | | | | | |
|---|---|---|---|---|---|---|
| | 0.06 | 0.6 | 1.2 | 1.8 | 2.4 | 3 |
| PA digested sample | − | − | − | − | + | + |
| EF digested sample | − | − | − | − | + | + |
| EK digested sample | − | − | − | − | + | + |

TABLE 9

SE probe

| Digested sample | Probe concentration (ng/μL) | | | | | |
|---|---|---|---|---|---|---|
| | 0.06 | 0.6 | 1.2 | 1.8 | 2.4 | 3 |
| SA digested sample | − | − | − | − | − | + |
| SE digested sample | − | + | + | + | + | + |
| PA digested sample | − | − | − | − | − | + |
| EF digested sample | − | − | − | − | − | + |
| EK digested sample | − | − | − | − | − | + |

TABLE 10

PA probe

| Digested sample | Probe concentration (ng/μL) | | | | | |
|---|---|---|---|---|---|---|
| | 0.06 | 0.6 | 1.2 | 1.8 | 2.4 | 3 |
| SA digested sample | − | − | − | − | − | − |
| SE digested sample | − | − | − | − | + | + |
| PA digested sample | − | + | + | + | + | + |
| EF digested sample | − | − | − | − | − | + |
| EK digested sample | − | − | − | − | − | + |

TABLE 11

EF probe

| Digested sample | Probe concentration (ng/μL) | | | | | |
|---|---|---|---|---|---|---|
| | 0.06 | 0.6 | 1.2 | 1.8 | 2.4 | 3 |
| SA digested sample | − | − | − | − | − | + |
| SE digested sample | − | − | − | − | + | + |
| PA digested sample | − | − | − | − | + | + |
| EF digested sample | − | + | + | + | + | + |
| EK digested sample | − | − | − | − | − | − |

TABLE 12

EK probe

| Digested sample | Probe concentration (ng/μL) | | | | | |
|---|---|---|---|---|---|---|
| | 0.06 | 0.6 | 1.2 | 1.8 | 2.4 | 3 |
| SA digested sample | − | − | − | − | + | + |
| SE digested sample | − | − | − | − | + | + |
| PA digested sample | − | − | − | − | + | + |
| EF digested sample | − | − | − | − | + | + |
| EK digested sample | − | + | + | + | + | + |

Applications of these results obtained using the digested samples to the present invention could result in similar results. Therefore, the optimal concentration of each probe described above in the identification of a causative microorganism of an infectious disease in the clinical specimen of the present invention was also set similarly.

Example 21

Examination on Hybridization Temperature

Reaction temperature in the hybridization reaction is a parameter which affects the hybridizing velocity and stability of the hybrid. Because high temperature of the hybridization reaction is known to deteriorate the cell morphology, examination of the optimal temperature (4° C., 25° C., 37° C., 42° C., 50° C. and 60° C.) was performed.

First, the digested samples produced according to the process described in Example 17(1) [1] and [2] were used as specimens. The phagocytosis rate of the used SA digested sample was 31% with $1.38 \times 10^5$ cells/well. The phagocytosis rate of the SE digested sample was 42% with $1.95 \times 10^5$ cells/well. The phagocytosis rate of the PA digested sample was 14% with $1.27 \times 10^5$ cells/well. In addition, the phagocytosis rate of the EF digested sample was 48% with $1.05 \times 10^5$ cells/well. The phagocytosis rate of the EK digested sample was 17% with $1.85 \times 10^5$ cells/well.

Figure 9:
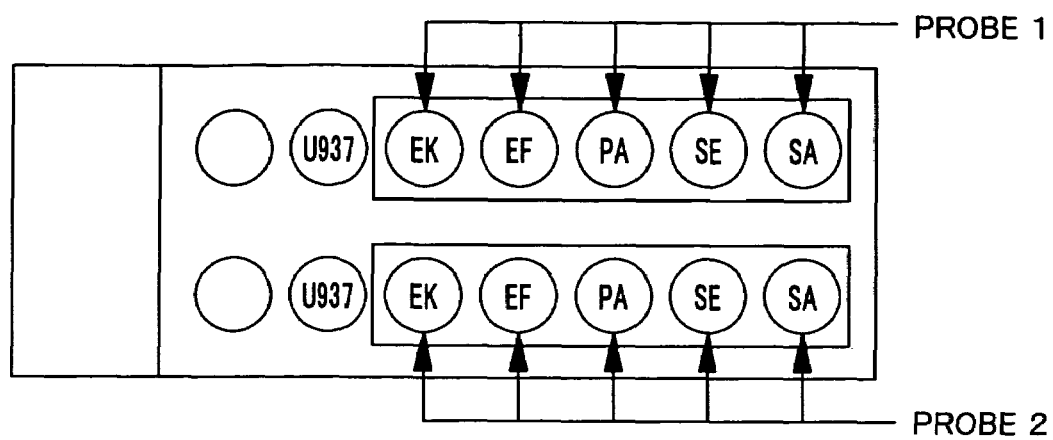
FIG. 9 is a schematic view of the slide on which the phagocytosis samples were smeared to study optimum temperature under the in situ hybridization.

Using the slide glass including the digested sample and U937 cells smeared and fixed thereon (see, FIG. 9), examination was conducted according to the process described in Examples 3-11. Consequently, no stable signal was observed for each type of probe at the hybridization temperature of 4° C. or less owing to the lowered hybridization velocity. Further, at 60° C., changes in cell morphology were detected, and thus no stable signal was observed. In addition, at 25° C. and 50° C., detection could be executed better compared to at the temperature of 37° C. and 42° C., although the signal was unclear. Hence, optimal temperature of the hybridization may be 25° C. to 50° C., more preferably 37 to 42° C. The results are shown in Tables 13-17 below.

TABLE 13

SA probe

| Digested sample | Hybridization temperature (° C.) | | | | | |
|---|---|---|---|---|---|---|
| | 4 | 25 | 37 | 42 | 50 | 60 |
| SA digested sample | − | + | + | + | + | + |
| SE digested sample | − | − | − | − | − | − |
| PA digested sample | − | − | − | − | − | − |
| EF digested sample | − | − | − | − | − | − |
| EK digested sample | − | − | − | − | − | − |

TABLE 14

SE probe

| Digested sample | Hybridization temperature (° C.) | | | | | |
|---|---|---|---|---|---|---|
| | 4 | 25 | 37 | 42 | 50 | 60 |
| SA digested sample | − | − | − | − | − | − |
| SE digested sample | + | + | + | + | + | − |
| PA digested sample | − | − | − | − | − | − |
| EF digested sample | − | − | − | − | − | − |
| EK digested sample | − | − | − | − | − | − |

TABLE 15

PA probe

| Digested sample | Hybridization temperature (° C.) | | | | | |
|---|---|---|---|---|---|---|
| | 4 | 25 | 37 | 42 | 50 | 60 |
| SA digested sample | − | − | − | − | − | − |
| SE digested sample | − | − | − | − | − | − |
| PA digested sample | − | + | + | + | + | − |
| EF digested sample | − | − | − | − | − | − |
| EK digested sample | − | − | − | − | − | − |

TABLE 16

EF probe

| Digested sample | Hybridization temperature (° C.) | | | | | |
|---|---|---|---|---|---|---|
| | 4 | 25 | 37 | 42 | 50 | 60 |
| SA digested sample | − | − | − | − | − | − |
| SE digested sample | − | − | − | − | − | − |
| PA digested sample | − | − | − | − | − | − |
| EF digested sample | + | + | + | + | + | − |
| EK digested sample | − | − | − | − | − | − |

TABLE 17

EK probe

| Digested sample | Hybridization temperature (° C.) | | | | | |
|---|---|---|---|---|---|---|
| | 4 | 25 | 37 | 42 | 50 | 60 |
| SA digested sample | − | − | − | − | − | − |
| SE digested sample | − | − | − | − | − | − |
| PA digested sample | − | − | − | − | − | − |
| EF digested sample | − | − | − | − | − | − |
| EK digested sample | − | + | + | + | + | − |

Applications of these results obtained using the digested samples to the present invention could result in similar results. Therefore, the optimal temperature of hybridization in the identification of a causative microorganism of an infectious disease in the clinical specimen of the present invention was also set similarly.

Example 22

Examination on Hybridization Time Period

The digested samples produced according to the process described in Example 17(1) [1] and [2] were used as specimens, and examination was conducted on the time period of hybridization of 10 minutes, 60 minutes, 90 minutes, 120 minutes, 180 minutes and 900 minutes. The phagocytosis rate of the used SA digested sample was 47% with $1.45 \times 10^5$ cells/well. The phagocytosis rate of the SE digested sample was 47% with $1.33 \times 10^5$ cells/well. The phagocytosis rate of the PA digested sample was 15% with $1.91 \times 10^5$ cells/well. In addition, the phagocytosis rate of the EF digested sample was 41% with $1.45 \times 10^5$ cells/well. The phagocytosis rate of the EK digested sample was 20% with $1.23 \times 10^5$ cells/well.

Using the slide glass including the digested sample and U937 cells smeared and fixed thereon (same as one shown in FIG. 9), examination was conducted according to the process described in Examples 3-11. Consequently, although no signal was observed with the time period of hybridization of 10 minutes, a signal was observed at 60 minutes or greater, and a stable signal was observed at 90 minutes or greater. Further, no alteration in detection of the signal was observed also with the time period of hybridization of 900 minutes. Therefore, it is preferred that the time period is at least 30 minutes or greater, preferably 60 minutes or greater, and more preferably 90 minutes or greater. More preferred optimal time period of hybridization may be set to be 120 minutes to 900 minutes. The results are shown in Tables 18-22 below.

TABLE 18

SA probe

| Digested sample | Hybridization time (minutes) | | | | | |
|---|---|---|---|---|---|---|
| | 10 | 60 | 90 | 120 | 180 | 900 |
| SA digested sample | − | + | + | + | + | + |
| SE digested sample | − | − | − | − | − | − |
| PA digested sample | − | − | − | − | − | − |
| EF digested sample | − | − | − | − | − | − |
| EK digested sample | − | − | − | − | − | − |

TABLE 19

SE probe

| Digested sample | Hybridization time (minutes) | | | | | |
|---|---|---|---|---|---|---|
| | 10 | 60 | 90 | 120 | 180 | 900 |
| SA digested sample | − | − | − | − | − | − |
| SE digested sample | + | + | + | + | + | + |
| PA digested sample | − | − | − | − | − | − |
| EF digested sample | − | − | − | − | − | − |
| EK digested sample | − | − | − | − | − | − |

TABLE 20

SE probe

| Digested sample | Hybridization time (minutes) | | | | | |
|---|---|---|---|---|---|---|
| | 10 | 60 | 90 | 120 | 180 | 900 |
| SA digested sample | − | − | − | − | − | − |
| SE digested sample | − | − | − | − | − | − |
| PA digested sample | − | + | + | + | + | + |
| EF digested sample | − | − | − | − | − | − |
| EK digested sample | − | − | − | − | − | − |

TABLE 21

EF probe

| Digested sample | Hybridization time (minutes) | | | | | |
|---|---|---|---|---|---|---|
| | 10 | 60 | 90 | 120 | 180 | 900 |
| SA digested sample | − | − | − | − | − | − |
| SE digested sample | − | − | − | − | − | − |
| PA digested sample | − | − | − | − | − | − |
| EF digested sample | + | + | + | + | + | + |
| EK digested sample | − | − | − | − | − | − |

TABLE 22

| | EK probe | | | | | |
|---|---|---|---|---|---|---|
| | Hybridization time (minutes) | | | | | |
| Digested sample | 10 | 60 | 90 | 120 | 180 | 900 |
| SA digested sample | – | – | – | – | – | – |
| SE digested sample | – | – | – | – | – | – |
| PA digested sample | – | – | – | – | – | – |
| EF digested sample | – | – | – | – | – | – |
| EK digested sample | – | + | + | + | + | + |

Applications of these results obtained using the digested samples to the present invention could result in similar results. Therefore, the optimal time period of hybridization in the identification of a causative microorganism of an infectious disease in the clinical specimen of the present invention was also set similarly.

Example 23

Influence of Surfactant Added to Hybridization Solution

The digested samples produced according to the process described in Example 17(1) [1] and [2] were used as specimens. When any of various surfactants (SDS, lauryl sarcosine, saponin, BRIJ35, Tween 20, Triton X-100) was added to the probe dilution solution followed by hybridization carried out according to Example 7, the detection sensitivity was dramatically enhanced by adding 0.25% SDS. In addition, the detection sensitivity could be improved by lauryl sarcosine, BRIJ 35 or Tween 20. The results are shown in Table 23 below.

TABLE 23

| Surfactant | Signal detection |
|---|---|
| None added | + |
| SDS | +++ |
| Lauryl sarcosine | ++ |
| Saponin | + |
| BRIJ 35 | ++ |
| Tween 20 | ++ |
| Triton X-100 | + |

Furthermore, as a consequence of using SDS at various concentrations, it was revealed that preferable concentration was 1% or less, more preferably 0.1% to 0.5%, and still more preferably 0.25%.

Applications of these results obtained using the digested samples to the present invention could result in similar results. Therefore, also in the present invention, it is preferred that a surfactant, particularly SDS, is added at the step of in situ hybridization.

Example 24

Examination on Chain Length of Probe Used in Hybridization

*Staphylococcus aureus* probe (SA-24 (SEQ ID NO: 1)) and *Pseudomonas aeruginosa* probe (P2-2 (SEQ ID NO: 7)) were labelled with digoxigenin.

First, 1 μg of purified each type of the DNA probe was prepared to give the total volume of 50 μg with 5 μl of 10×L.B. (0.5 mol/l Tris-hydrochloric acid (pH 7.5), 50 mmol/l magnesium chloride, 5 μl of 0.5 mg bovine serum albumin), 5 μl of 100 mmol/l dithiothreitol, each 1 nmol of dNTPs (A, G, C), 0.5 nmol of digoxigenin-dUTP (Dig-dUTP), each 0.5 nmol of dTTP, 3 μl of DNase (amount corresponding to 25 mU, 75 mU and 200 mU), 1 μl of 10 U/μl DNA polymerase and an appropriate amount of sterile purified water. Digoxigenin labelling was performed at 15° C. for 2 hours. After the labelling, the mixture was boiled for 5 minutes to terminate the reaction. The reaction liquid after the termination was injected into a spin column (CENTRI-SEP COLUMNS CS901, PRINCETON SEPARATIONS, INC.), and centrifuged at 25° C. for 2 minutes (3,000×g) to remove free nucleotides. Then, concentration of the eluate was measured by an absorbance meter. Electrophoresis was performed on a 3% agarose gel to confirm the size.

Next, DNA in the agarose gel was transferred to a nitrocellulose membrane by Southern blotting method. Then, the membrane was immersed in 2% blocking reagent (manufactured by Roche) for 30 minutes, and thereafter, alkaline phosphatase labelled anti-digoxigenin antibody in an amount of 1/5,000 was added thereto and the immersion was allowed for 30 minutes. Next, the membrane was washed twice by shaking in 100 mmol/l Tris-hydrochloric acid (pH 7.5) and 150 mmol/l sodium chloride for 10 minutes. Thereafter, washing was executed by shaking in 100 mmol/l Tris-hydrochloric acid (pH9.5) and 150 mmol/l sodium chloride for 10 minutes. Then, color development was conducted by immersing in an NBT/BCIP solution.

Figure 10:
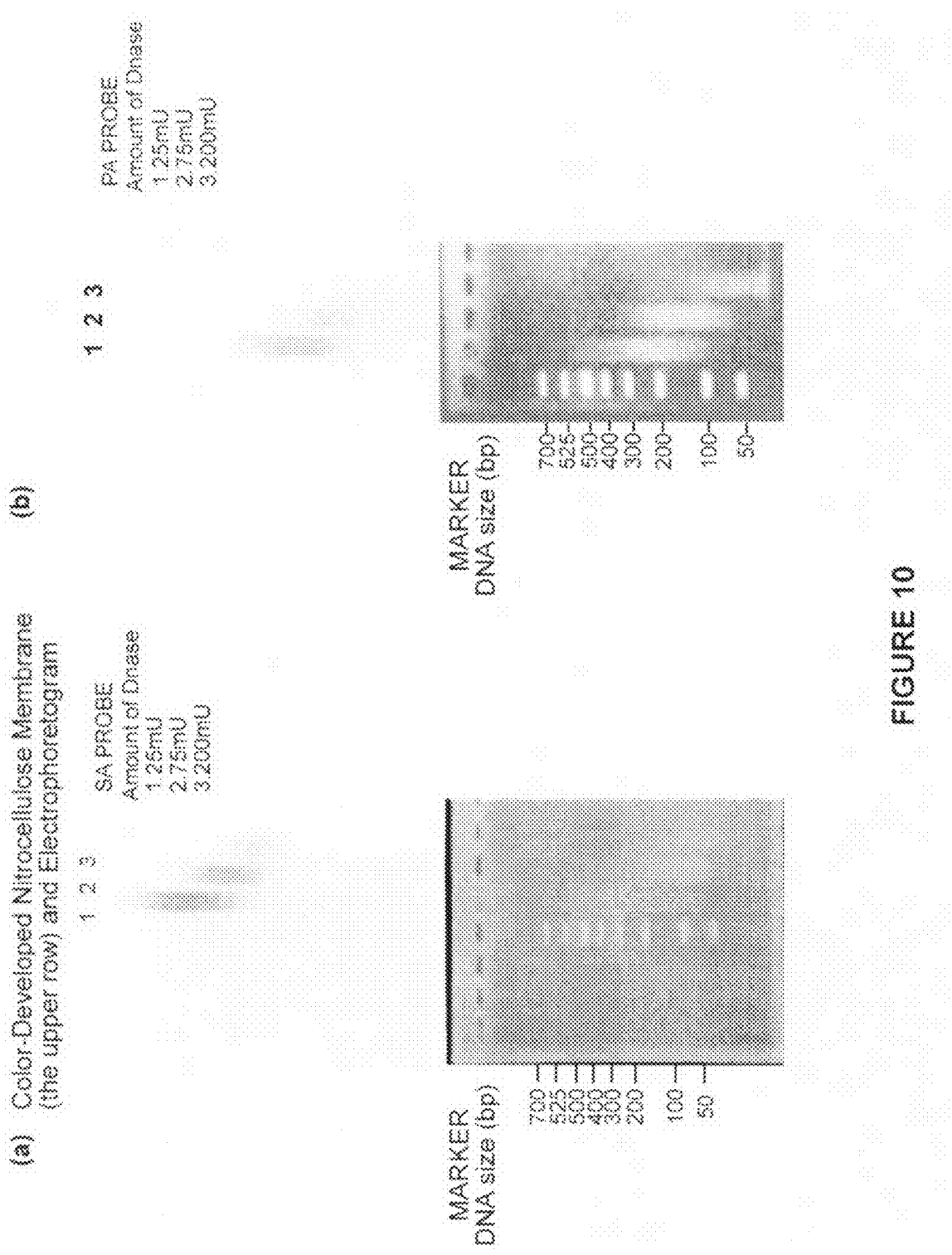
FIG. 10 is a view of illustrating the signals appeared in the results of Southern Blot (the upper row) and Electrophoresis (the lower row) together with the length of the labelled detective probes prepared by putting digoxigenin-labels on (a) SA probes and (b) PA probes.

Finally, the membrane was immersed in purified water to stop the color development, and dried. Consequently, as shown in FIG. 10 for (a) use of the SA probe and (b) use of the PA probe, respectively, it was indicates that in cases where cleavage was conducted using 25 mU of DNase (in Figure, lane 1) such that the chain length distributes the base length of predominantly about 350 to about 600, high labelling efficiency was achieved. When thus resulting probe for detection was used in the process for detecting a causative microorganism of an infectious disease according to the present invention in which a digested sample or a clinical specimen from a patient suffering from an infectious disease was used to carry out hybridization, a signal could be detected with excellent sensitivity. Therefore, it was reveled that chain length of the probe used in the hybridization may be the base length of about 350 to about 600, and preferably the base length of about 350 to about 550.

Example 25

Examination on Probe Used in Hybridization

*Escherichia coli* digested samples produced according to the process described in Example 17(1) [1] and [2] were used as specimens to examine on the probes for detection.

Figure 11:
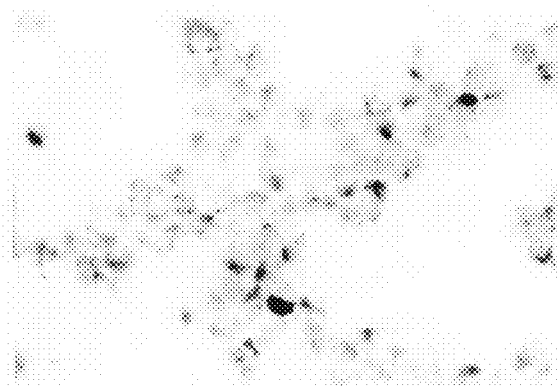
FIG. 11 is a view of illustrating the signals detected by in situ hybridization of the digested *Escherichia coli* with detective probes of (a) EC-24, (b) EC-34, (c) EC-39 and (d) the mixed probes (MIX) of the foregoing probes (a)-(c).
Figure 11:
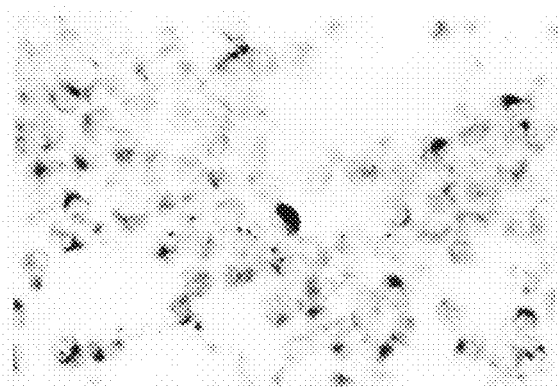
Figure 11:
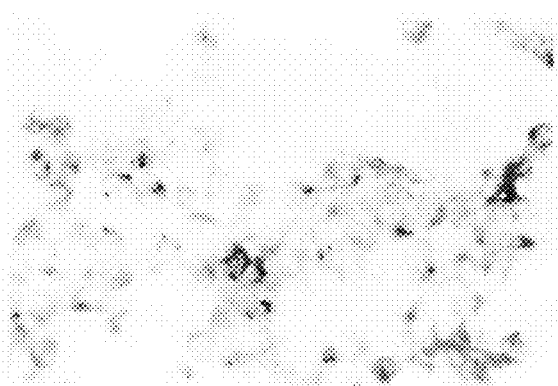
Figure 11:
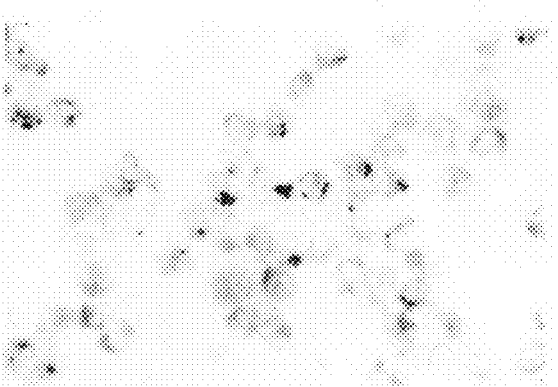

Probes for detection were prepared through labelling with digoxigenin as described in Example 24 from EC-24 (SEQ ID NO: 11), EC-34 (SEQ ID NO: 12) and EC-39 (SEQ ID NO: 13) such that they have the base length of about 350 to about 600, and used alone or in combination of those three, respectively. From thus obtained results, it was evident that the signal could be detected more clearly resulting in elevated sensitivity for (d) the mixed probe MIX prepared by mixing the three ((a) EC-24, (b) EC-34 and (c) EC-39), than for each (a) EC-24, (b) EC-34 or (c) EC-39 used alone, as shown in FIG. 11.

INDUSTRIAL APPLICABILITY

Since the in situ hybridization according to the present method can offer the stable signals within two hours or less, detection results can be presented very rapidly. Obviously, such rapid detection demonstrates the value of the present method in the rapid diagnosis of sepsis.

The invention claimed is:

1. A method for detecting and/or identifying microorganisms causative of infectious diseases, comprising the steps of:
  (a) taking phagocytes from a clinical specimen and adjusting cell density of the phagocytes to between $5 \times 10^6$ cells/ml and $1 \times 10^8$ cells/ml;
  (b) immobilizing the phagocytes onto a solid support;
  (c) treating the phagocytes with lytic enzyme under the presence of protease inhibitor to increase phagocyte cell membrane permeability and bare DNA in the phagocytes;
  (d) in situ hybridizing the bared DNA with at least one DNA probe which can hybridize with DNA of at least one microorganism causative of an infectious disease under conditions wherein the hybridization of the at least one DNA probe is specific to the DNA of the at least one microorganism causative of an infectious disease; and
  (e) detecting and/or identifying the at least one microorganism causative of an infectious disease by detecting hybridization the of at least one probe to the bared DNA.

2. The method according to claim 1, wherein the lytic enzyme in step (c) is selected from the group consisting of Lysostaphin in a titer of from 1 Unit/ml to 1,000 Units/ml; Lysozyme in a titer of from 1,000 Units/ml to 1,000,000 Units/ml; N-acetylmuramidase in a titer of from 10 Units/ml to 10,000 Units/ml; Zymolase in a titer of from 50 Units/ml to 500 Units/ml, and a combination of any of the foregoing.

3. The method according to claim 1, wherein step (c) is performed under a temperature of about 26° C. to about 59° C. for about 15 to about 120 minutes.

4. The method according to claim 1, wherein the protease inhibitor in said step (c) is phenylmethylsulfonyl fluoride (PMSF).

5. The method according to claim 4, wherein the PMSF is employed at a concentration of about 10 µmol/l to about 10 mmol/l.

6. The method according to claim 1, wherein the protease inhibitor in said step (c) is dissolved into dimethylsulfoxide (DMSO).

7. The method according to claim 6, wherein the DMSO is in a concentration of less than about 5% by volume.

8. The method according to claim 1, wherein step (d) is performed at a temperature of about 25° C. to about 50° C. for about 30 to about 900 minutes.

9. The method according to claim 1, wherein the solid support in step (b) is a slide coated with 3-aminopropyl triethoxysilane.

10. The method according to claim 1, wherein step (e) comprises detecting signals resulting from hybridization, wherein pigment is employed to distinguish between said signals and cells.

11. The method according to claim 1, wherein the clinical specimen is blood.

12. The method according to claim 1, wherein length of the at least one DNA probe is from about 350 bases to about 600 bases.

13. The method according to claim 1, wherein concentration of the at least one DNA probe is from about 0.1 ng/µl to about 2.2 ng/µl.

14. The method of claim 1, wherein the in situ hybridizing of step (d) is performed in the presence of a surfactant.

15. The method according to claim 14, wherein the surfactant is sodium dodecyl sulfate (SDS).

16. A method for diagnosing sepsis or bacteremia, comprising:
  (a) taking phagocytes from a clinical specimen and adjusting cell density of the phagocytes to between $5 \times 10^6$ cells/ml and $1 \times 10^8$ cells/ml;
  (b) immobilizing the phagocytes onto a solid support;
  (c) treating the phagocytes with lytic enzyme under the presence of protease inhibitor to increase phagocyte cell membrane permeability and bare DNA in the phagocytes;
  (d) in situ hybridizing the bared DNA with at least one DNA probe which can hybridize with DNA of at least one microorganism causative of sepsis or bacteremia under conditions wherein the hybridization of the at least one DNA probe is specific to DNA of the at least one microorganism causative of sepsis or bacteremia; and
  (e) diagnosing sepsis or bacteremia by detecting hybridization of at least one probe to the bared DNA.

17. The method of claim 16, wherein the in situ hybridizing of step (d) is performed in the presence of a surfactant.

* * * * *

UNITED STATES PATENT AND TRADEMARK OFFICE
CERTIFICATE OF CORRECTION

PATENT NO.      : 7,651,837 B2                                          Page 1 of 1
APPLICATION NO. : 10/479185
DATED           : January 26, 2010
INVENTOR(S)     : Ohno et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 848 days.

Signed and Sealed this

Twenty-third Day of November, 2010

David J. Kappos
*Director of the United States Patent and Trademark Office*

SEQUENCE LISTING

<160> NUMBER OF SEQ ID NOS: 19

<210> SEQ ID NO 1
<211> LENGTH: 10207
<212> TYPE: DNA
<213> ORGANISM: Staphylococcus aureus
<220> FEATURE:
<223> OTHER INFORMATION: Designated as SA-24

<400> SEQUENCE: 1

| | | | | | |
|---|---|---|---|---|---|
| aagcttatgg | acctatttta | ggtatattga | ttagttggct | tggattaatt | tctggaacat | 60 |
| ttacagtcta | tttgatctgt | aaacgattgg | tgaacactga | gaggatgcag | cgaattaaac | 120 |
| aacgtactgc | tgttcaacgc | ttgattagtt | ttattgatcg | ccaaggatta | atcccattgt | 180 |
| ttattttact | ttgttttcct | tttacgccaa | atacattaat | aaattttgta | gcgagtctat | 240 |
| ctcatattag | acctaaatat | tatttcattg | ttttggcatc | atcaaagtta | gtttcaacaa | 300 |
| ttatttttagg | ttatttaggt | aaggaaatta | ctacaatttt | aacgcatcct | ttaagaggga | 360 |
| tattaatgtt | agttgtgttg | gttgtatttt | ggattgttgg | aaaaaagtta | gaacagcatt | 420 |
| ttatgggatc | gaaaaaggag | tgacatcgtg | aaaaaagttg | taaaatattt | gatttcattg | 480 |
| atacttgcta | ttatcattgt | actgttcgta | caaacttttg | taatagttgg | tcatgtcatt | 540 |
| ccgaataatg | atatgtcacc | aacccttaac | aaagggacgt | gttattgtaa | ataaaattaa | 600 |
| agttacattt | aatcaattga | ataatggtga | tatcattaca | tataggcgtg | gtaacgagat | 660 |
| atatactagt | cgaattattg | ccaaacctgg | tcaatcaatg | gcgtttcgtc | agggacaatt | 720 |
| ataccgtgat | gaccgaccgg | ttgacgcatc | ttatgccaag | aacagaaaaa | ttaaagattt | 780 |
| tagtttgcgc | aattttaaag | aattagatgg | agatattata | ccgcctaaca | ttttgttgt | 840 |
| gctaaatgat | catgataaca | atcagcatga | ttctagacaa | tttggtttaa | ttgataaaaa | 900 |
| ggatattatt | ggtaatataa | gtttgagata | ttatccttt | tcaaaatgga | cgattcagtt | 960 |
| caaatcttaa | aaagaggtgt | caaaattgaa | aaaagaatta | ttggaatgga | ttatttcaat | 1020 |
| tgcagtcgct | tttgtcattt | tatttatagt | aggtaaattt | attgttacac | catatacaat | 1080 |
| taaaggtgaa | tcaatggatc | caactttgaa | agatggcgag | cgagtagctg | taaacattat | 1140 |
| tggatataaa | acaggtggtt | tggaaaaagg | taatgtagtt | gtcttccatg | caaacaaaaa | 1200 |
| tgatgactat | gttaaacgtg | tcatcggtgt | tcctggtgat | aaagtagaat | ataaaaatga | 1260 |
| tacattatat | gtcaatggta | aaaaacaaga | tgaaccatat | ttaaactata | atttaaaaca | 1320 |
| taaacaaggt | gattacatta | ctgggacttt | ccaagttaaa | gatttaccga | atgcgaatcc | 1380 |
| taaatcaaat | gtcattccaa | aaggtaaata | tttagttctt | ggagataatc | gtgaagtaag | 1440 |
| taaagatagc | cgtgcgtttg | gcctcattga | tgaagaccaa | attgttggta | agtttcatt | 1500 |
| tagattctgg | ccatttagtg | aatttaaaca | taatttcaat | cctgaaaata | ctaaaaatta | 1560 |
| atatgaaaca | aatacaacat | cgtttgtcgg | ttttaatact | gataaacgat | gttttatttt | 1620 |
| gttagtacca | caataaaagc | taagttcgaa | atgaacttat | aataaatcaa | tcacaatcac | 1680 |
| tttgtgttaa | aatatgtgtc | aaaggaagtg | agggtttgtc | atgacattac | atgcttattt | 1740 |
| aggtagagcg | ggaacaggta | agtctacgaa | aatgttgacc | gaaataaaac | aaaaaatgaa | 1800 |
| agcagatccg | cttggagatc | caatcatttt | aattgcgcca | actcaaagta | catttcaatt | 1860 |
| agaacaagcc | tttgtcaatg | atccggaatt | aaatggtagt | ttaagaacag | aagtgttgca | 1920 |
| ttttgaacga | ttaagtcatc | gtattttcca | agaagttggt | agttatagcg | aacaaaagtt | 1980 |

```
atctaaagct gcaacggaaa tgatgattta taacattgtt caagaacaac aaaagtattt   2040
aaaactttat caatcacaag caaaatatta tgggtttagt gaaaaattaa cagaacaaat   2100
tcaagatttt aaaaaatatg cagtaacgcc tgaacattta gaacacttta ttgctgataa   2160
aaatatgcaa actcgaacta aaaataagtt agaggatatt gctttaatat accgtgagtt   2220
cgaacaacgc attcaaaacg agtttattac tggtgaggat tcattacaat attttattga   2280
ttgtatgccg aaatcagagt ggctaaaacg tgctgatata tatattgatg gttttcacaa   2340
cttttcaacg attgagtatt taataatcaa aggattaatt aaatatgcga gagtgtcaca   2400
attatattga cgacagatgg taaccacgat caatttagtt ttttagaaaa ccatcggaag   2460
tgttacgaca tattgaagaa atagcaaatg aactcaatat ttctattgaa cgtcaatatt   2520
tcaaccaatt atatcgcttc aataatcaag atttaaagca tcttgaacaa gaatttgatg   2580
tacttcaaat caatcgagtg gcatgtcaag gtcatatcaa tattttagaa tctgcgacta   2640
tgagagagga ataaatgaa attgcgcgac gtatcatcgt tgatattcgt gataagcaat   2700
tacgatatca agatattgca attttatatc gtgacgagtc ttatgcttat ttatttgatt   2760
ccatattacc gctttataat attccttata acattgatac aaagcgttcg atgacacatc   2820
atccggtcat ggaaatgatt cgttcattga ttgaagttat tcaatctaat tggcaagtga   2880
atccaatgct acgcttattg aagactgatg tgttaacggc atcatatcta aaaagtgcat   2940
acttagttga tttacttgaa aattttgtac ttgaacgtgg tatatacggt aaacgttggt   3000
tagatgatga gctatttaat gtcgaacatt ttagcaaaat ggggcgtaaa gcgcataaac   3060
tgaccgaaga tgaacgtaac acatttgaac aagtcgttaa gttaaagaaa gatgtcattg   3120
ataaaatttt acattttgaa aagcaaatgt cacaagcgga aactgtaaaa gactttgcaa   3180
ctgcttttta tgaaagtatg gaatatttcg aactgccaaa tcaattgatg acagagcgag   3240
atgaacttga tttaaatggt aatcatgaaa aggcggagga aattgatcaa atatggaatg   3300
gcttaattca aatccttgac gacttagttc tagtatttgg agatgaacca atgtcgatgg   3360 aacgttctt agaagtattt gatattggtt tagaacaatt agaatttgtc atgattccac   3420
aaacattaga tcaagttagt attggtacga tggatttggc taaagtcgac aataagcaac   3480
atgtttactt agttggaatg aacgacggca ccatgccaca accagtaact gcatcaagtt   3540
taattactga tgaagaaaag aaatattttg aacaacaagc aaatgtagag ttgagtccta   3600
catcagatat tttacagatg gatgaagcat ttgtttgcta tgttgctatg actagagcta   3660
agggagatgt tacattttct tacagtctaa tgggatcaag tggtgatgat aaggagatca   3720
gcccattttt aaatcaaatt caatcattgt tcaaccaatt ggaaattact aacattcctc   3780
aataccatga agttaaccca ttgtcactaa tgcaacatgc taagcaaacc aaaattacat   3840
tatttgaagc attgcgtgct tggttagatg atgaaattgt ggctgatagt tggttagatg   3900
cttatcaagt aattagagat agcgatcatt taaatcaagg tttagattat ttaatgtcag   3960
cattaacgtt tgacaatgaa actgtaaaat taggtgaaac gttgtctaaa gatttatatg   4020
gtaaggaaat caatgccagt gtatctcgtt ttgaaggtta tcaacaatgc ccatttaaac   4080
actatgcttc acatggtctg aaactaaatg aacgaacgaa atatgaactt caaaactttg   4140
atttaggtga tattttccat tccgttttaa aatatatatc tgaacgtatt aatggcgatt   4200
ttaaacaatt agacctgaaa aaaataagac aattaacgaa tgaagcattg gaagaaattt   4260
tacctaaagt tcagtttaat ttattaaatt cttcagctta ctatcgttat ttatcaagac   4320
```

```
gcattggcgc tattgtagaa acaacactaa gcgcattaaa atatcaaggc acgtattcaa   4380
agtttatgcc aaaacatttt gagacaagtt ttagaaggaa accaagaacc aaatgtacga   4440
attaattgca caaacattaa cgacaactca aggtattcca attaatatta gagggcaaat   4500
tgaccgtatc gatacgtata caaagaatga tacaagtttt gttaatatca ttgactataa   4560
atcctctgaa ggtagtgcga cacttgattt aacgaaagta tattatggta tgcaaatgca   4620
aatgatgaca tacatggata tcgttttaca aaataaacaa cgccttggat taacagatat   4680
tgtgaaacca ggtggattat tatacttcca tgtacatgaa cctagaatta aatttaaatc   4740
atggtctgat attgatgaag ataaactaga acaagattta attaaaaagt ttaagctgag   4800
tggtttagtg aatgcagacc aaactgttat tgatgcattg gatattcgtt tagaacctaa   4860
attcacttca gatattgtac cagttggttt gaataaagat ggctctttga gtaaacgagg   4920
cagccaagtg gcagatgaag caacaattta taaattcatt cagcataaca agagaatttt   4980
tatagaaaca gcttcaaata ttatggatgg acatactgaa gtgcaccatt aaagtacaaa   5040
caaaaattgc catgtgcttt ttgtagttat caatcggtat gtcatgtaga tggcatgatt   5100
gatagtaagc gatatcgaac tgtagatgaa acaataaatc caattgaagc aattcaaaat   5160
attaacatta atgatgaatt tgggggtgag taatagatga caattccaga gaaaccacaa   5220
ggcgtgattt ggactgacgc gcaatggcaa agtatttacg caactggaca agatgtactt   5280
gttgcagccg cggcaggttc aggtaaaaca gctgtactag ttgagcgtat tatccaaaag   5340
attttacgtg atggcattga tgtcgatcga cttttagtcg taacgtttac aaacttaagc   5400
gcacgtgaaa tgaagcatcg tgtagaccaa cgtattcaag aggcatcgat tgctgatcct   5460
gcaaatgcac acttgaaaaa ccaacgcatc aaaattcatc aagcacaaat atctacactt   5520
catagttttt gcttgaaatt aattcaacag cattatgatg tattaaatat tgacccgaac   5580
tttagaacaa gcagtgaagc tgaaaatatt ttattattag aacaaacgat agatgaggtc   5640
atagaacaac attacgatat ccttgatcct gcttttattg aattaacaga acaattgtct   5700
tcagatagaa gtgatgatca gtttcgaatg attattaaac aattgtattt ctttagcgtt   5760
gcaaatccaa atcctacaaa ttggttggat caattggtga caccatacga agaagaagca   5820
caacaagcgc aacttattca actactaaca gacttatcta agtatttat cacagctgcc   5880 tatgatgctt taaataaggc gtatgatttg tttagtatga tggatggcgt cgataaacat   5940
ttagctgtta tagaagatga acgacgttta atggggcgtg ttttagaagg tggttttatt   6000
gatataccTT atttaactga tcacgaattt ggcgcgcgtt tgcctaatgt aacagcgaaa   6060
attaaagaag caaatgaaat gatggtcgat gccttagaag atgctaaaact tcagtataaa   6120 aaatataaat cattaattga taaagtgaaa aatgattact tttcaagaga agctgatgat   6180
ttgaaagctg atatgcaaca attggcgcca cgagtaaagt accttgcgcg tattgtgaaa   6240
gatgttatgt cagaattcaa tcgaaaaaag cgtagcaaaa atattctgga ttttctgat   6300 tatgaacaat ttgcattaca aattttaact aatgaggatg gttcgccttc agaaattgcc   6360
gaatcatacc gtcaacactt tcaagaaata ttggtcgatg agtatcaaga tacgaaccgg   6420
gttcaagaga aaatactatc ttgcatcaaa acgggtgatg aacataatgg taatttattt   6480
atggttggag atgttaagca atccatttat aaatttagac aagctgatcc aagtttattt   6540
attgaaaagt atcaacgctt tactatagat ggagatggca ctggacgtcg aattgatttg   6600 tcgcaaaaact ccgttctcga aaagaagtac tgtcaacgac taactatata tcaaacatat   6660
gatggatgaa caagtcggtg aagtaaaata tgatgaagcg gcacagttgt attatggtgc   6720
```

```
accatatgat gaatcggacc atccagtaaa cttaaaagtg cttgttgaag cggatcaaga    6780
acatagtgat ttaactggta gtgaacaaga agcgcatttt atagtagaac aagttaaaga    6840
tatcttagaa catcaaaaag tttatgatat gaaaacagga agctatagaa gtgcgacata    6900
caaagatatc gttattctag aacgcagctt tggacaagct cgcaatttac aacaagcctt    6960
taaaaatgaa gatattccat tccatgtgaa tagtcgtgaa ggttactttg aacaaacaga    7020
agtccgctta gtattatcat ttttaagagc gatagataat ccattacaag atatttattt    7080
agttgggtta atgcgctccg ttatatatca gttcaaagaa gacgaattag ctcaaattag    7140
aatattgagt caaatgatga ctacttctat caatcgattg taaattacat taatgacgaa    7200
gcagcagatg ctattttagt tgataaatta aaaatgtttt tatcagatat tcaaagttac    7260
caacaatata gtaaagatca tccggtgtat cagttaattg ataaattta taatgatcat    7320 tatgttattc aatactttag tggacttatt ggtggacgtg gacgacgtgc aaacctttat    7380
ggtttattta ataaagctat cgagtttgag aattcaagtt ttagaggttt atatcaattt    7440
attcgtttta tcgatgaatt gattgaaaga ggcaaagatt ttggtgagga aaatgtagtt    7500
ggtccaaacg ataatgttgt tagaatgatg acaattcata gtagtaaagg tctagagttt    7560
ccatttgtca tttattctgg attgtcaaaa gattttaata aacgtgattt gaaacaacca    7620 gttatttaa atcagcaatt tggtctcgga atggattatt ttgatgtgga taaagaaatg    7680
gcatttccat ctttagcttc ggttgcatat aaagctgttg ccgaaaaaga acttgtgtca    7740
gaagaaatgc gattagtcta tgtagcatta acaagagcga aagaacaact ttatttaatt    7800
ggtagagtga aaaattgata aatcgttact agaactagag caattgtcta tttctggtga    7860
gcacattgct gtcaatgaac gattaacttc accaaatccg ttccatctta tttatagtat    7920
tttatctaaa catcaatctg cgtcaattcc agatgattta aatttgaaa agatatagc     7980 acaagttgaa gatagtagtc gtccgaatgt aaatatttca attatatact ttgaagatgt    8040
gtctacagaa accattttag ataataatga atatcgttcg gttaatcaat tagaaactat    8100
gcaaaatggt aatgaggatg ttaaagcaca aattaaacac caacttgatt atcaatatcc    8160
atatgtaaat gatactaaaa agccatccaa aacaatctgt ttctgaattg aaaaggcaat    8220
atgaaagaag aaagtggcac aagttacgaa cgagtaagac aatatcgtat cggttttcaa    8280
cgtatgaacg acctaaattt ctaagtgaac aaggtaaacg aaaaagcgaa ttgaaattgg    8340
tacgttaatg catacagtga tgcaacattt accattcaaa aaagaacgca tatctgaagt    8400
tgagttacat cagtatatcg atggattaat cgataaacat attatcgaag cagatgcgaa    8460 aaagatatc cgtatggatg aaataatgac attatcaata gtgagtatat tcgattattg    8520
ctgaagcaga gcaagtttat cgtgaattac cgtttgtagt taaccaagca ttagttgacc    8580
aattgccaca aggagacgaa gacgtctcaa ttattcaagg tatgattgac ttaatctttg    8640
ttaaagatgg tgtgcattat tttgtagact ataaaaccga tgcatttaat cgtcgccgtg    8700
ggatgacaga tgaagaaatt ggtacacaat taaaaaataa atataagata cagatgaaat    8760
attatcaaaa tacgcttcaa acgatactta ataaagaagt taaaggttat ttatacttct    8820
tcaaatttgg tacattgcaa ctgtagtatt ttgattttca aaagaataaa aataaatttc    8880
gattaagtgc aaagtccttg tagcagaatg aacacaactc attttcaaaa ttgtcttact    8940
tatttatttg ttatttgata acgaaaaaag ttataatgtg aattaagata aagatgagga    9000
gttgagaatg aatgaaattc ttatcattca agtataatga caaaacttca tatggcgtta    9060
```

-continued

| | |
|---|---|
| aagtaaaacg cgaagatgct gtatgggatt taacacaagt atttgctgac tttgcagaag | 9120 |
| gagatttcca tcctaaaaca ttgttagctg gtttacaaca aaatcatact ttagattttc | 9180 |
| aagaacaagt acgtaaagca gttgtagcag cagaagatag cggcaaagct gaagactata | 9240 |
| aaatttcatt taatgacatt gaattcttac caccagtaac acctccgaat aatgtgattg | 9300 |
| cttttggtag aaattacaaa gatcatgcga acgaattaaa tcatgaagta gaaaaattat | 9360 |
| atgtatttac aaaagcagcg tcatctttaa caggagataa tgcaacaatt ccaaatcata | 9420 |
| aagatattac tgatcaatta gattatgaag gtgaattagg tattgttatt ggtaagtctg | 9480 |
| gtgaaaagat tccaaaagca ttagctttag attatgttta cggctataca attattaacg | 9540 |
| atatcactga tcgcaaagca caaagtgaac aagatcaagc attttatca aaagtttaa | 9600 |
| ctggcggttg cccaatgggt ccttatatcg ttactaaaga cgaactacca ttacctgaaa | 9660 |
| atgtaaatat tgttacaaaa gttaacaatg aaattagaca agatggtaac actggcgaaa | 9720 |
| tgattcttaa aattgatgaa ttaatagaag aaatttcaaa atatgttgca ctactaccgg | 9780 |
| gagattatta ttgcaactgg tacaccagct ggcgttggtg caggtatgca accacctaaa | 9840 |
| tttttacaac caggtgatga agttaaagtg actattgata atattggaac gctgacaact | 9900 |
| tatatcgcta ataattatc atttaaaaag ctaaccaggt ctttatatag attggttagt | 9960 |
| tttttcttgc ttttctaaaa aggtgttaaa gataaattat ttataatgtt accatttga | 10020 |
| gatgaaagtg aaatattgat attaagaagt agttgattat tttacagcag attcacaata | 10080 |
| ttctaataag ggcaatgcaa atgtcatgtt cttcctctca aatatagaag tgtggtagaa | 10140 |
| tatatattcg tgtataatca aatctagatt aaattacaag caagtgggta ttaatcccaa | 10200 |
| gaagctt | 10207 |

<210> SEQ ID NO 2
<211> LENGTH: 2082
<212> TYPE: DNA
<213> ORGANISM: Staphylococcus aureus
<220> FEATURE:
<223> OTHER INFORMATION: Designated as SA-36

<400> SEQUENCE: 2

| | |
|---|---|
| aagctttcta atctatcgtt aatgatttgc tttaaaattg ggtcgaagtt aattgaaggt | 60 |
| gtgaagtgta tatctgtatt aataaccatg tcattcattt gctgcttcac tttgttaaca | 120 |
| agtcttccgt catataaaaa taatggtacg acaatcaatt tttgataccg tttcgagatg | 180 |
| cttttctaaat catgtgtaaa actaatctct ccatatagcg ttctcgcata agtaggttta | 240 |
| ttaatctgca aatgttgagc gcatatttgt aactcttcgt gtgccttagt aaaatttcca | 300 |
| ttaatattgc cgtgtgcaac aaccataact ccaacttgtt gttcgtcacc tgctaatgcg | 360 |
| tcacaaatac gttgttcaat taatcgtctc attaaaggat gtgtgccaag tggctcgctt | 420 |
| acttctacct ttatgtctgg ataccgtcgt ttcatttcat gaacgatatt cggtatatcc | 480 |
| ttgagataat gcattgcact aaagattagc aatggtacaa ttttaaaatg gtcaacccca | 540 |
| ctttgaatca acgtcgtcat taccgtctct aaatcctgat gctcactttc taaaaacgca | 600 |
| atatcatagt gatgtatatc atctttact aattcagaaa taaatgcttc taacgcttga | 660 |
| ttctgtcgtc cgtgcctcat gccatgtgca acaatgatat tcccattcac atttaccaac | 720 |
| cctttcacac gtattgtata ccaaatcatt tgtttttgt gaaaagaatc acattataat | 780 |
| gtaaaatcag ggaattccct gatgcctgta gtcatgcata ttccttatac attttcccctt | 840 |
| tttgttaaat caaaaaaagc gaccgatata tgaatcccta ctcaacattt atttgagcaa | 900 |

-continued

| | |
|---|---|
| gcatcaatat atcggtcgct tgtagtgtat attattatct taaaatggtg gttggcctaa | 960 |
| tattgtttcg tcaaagcgct cgggtatcaa tactttgcgc atgatcacac ctaaatcgcc | 1020 |
| atcatcattt tcatgttcgc tgtatatttc ataacctctt ttttcataaa ttttaagtaa | 1080 |
| ccacggatgc aatcttgcag atgtacctaa agtaactgcc gctgacttta acgtatctcg | 1140 |
| caaaaatgct cttcaacata agtaagtaat tggctaccat agcctttccc ttcatactca | 1200 |
| ggatttgtcg caaaccacca gacaaaagga tagcccgaaa tacttttcac acttccccaa | 1260 |
| ggatatctaa ccgtaatcgt agatataatt tcatcatcaa ttgtcatgac aaatgtagta | 1320 |
| ttttatcta tattttctt aacagcatct aaattagcat taactgaagg ccaatcaata | 1380 |
| cctagttctc ttagaggcgt aaatgcttca tgcatgagtt gttgcaattt ttctgcatct | 1440 |
| tgttcacttg cgagtcgaat catcgttttt gtcatattaa tccccactct tttttaaatg | 1500 |
| atttaaccat attttatttt taaaataaat atccatcaaa gtgtatcaat aaatttatca | 1560 |
| catgtcagaa agtatgcttc atctgaatac accaatactc tcatgaaact tattaaaaat | 1620 |
| tactctctca acgtaaaaaa accattcaaa ttcatgaatg gtttggaaga atgattcatt | 1680 |
| gttacgctat ttaatcacta catcttaatt attgttgctc taaacgatta cgcttaccat | 1740 |
| ttaagaaagc ataaacgaga cctacaaaaa taccgccacc gacaaagtta cctaagaaag | 1800 |
| caaaaacgat attttttaaa acatgtaacc atgaaactgc atcaaggtta aagaatacca | 1860 |
| tacctgcata tagacctgca ttgaacacaa cgtgctcata tcccatgtat acaaagacca | 1920 |
| cgacaccaca agctatgaag aatgcctttg ttaagccgcc tttgaattgc atagagatga | 1980 |
| aaataccaat attaataaag aagttacaga aaatacctt tgtaaaaata ttcaaccatg | 2040 |
| ttgaatcaac agtcttttc tgaactaaag ctgttaaagc tt | 2082 |

<210> SEQ ID NO 3
<211> LENGTH: 2885
<212> TYPE: DNA
<213> ORGANISM: Staphylococcus aureus
<220> FEATURE:
<223> OTHER INFORMATION: Designated as SA-77

<400> SEQUENCE: 3

| | |
|---|---|
| aagcttttga ttaatttggg ctttaaagta ttcccaatta taattcttca tgattttctt | 60 |
| attggatttc gaatttggtt tcatgcattg ttgcctcaaa gaacatgctg aacagtcatc | 120 |
| gcattcatat agcttgaagt cacgtttaaa accatatcta tcattacggt atgcatatct | 180 |
| tttaaaacct attctttgt tattaggaca tataaattca tcattaagtt cgtcatattt | 240 |
| ccaatttga gtgttaaaaa tgtcactttt aaactttcta gttttatctt taataaacat | 300 |
| gccatacgta ataagtggcg ttttattaaa acatctataa tagccatata gttttgctca | 360 |
| ctatcataac tgcatcagct acattaactc tggtaatacc gaggatttga atcattgtta | 420 |
| aaaatggaat taaagttcta gtatctgttg gggtttgaaa taggtcatag gataaaaaaa | 480 |
| ttgagaattt gtcgctattt gtaaattgta tcctggctta agttggccat ttttcatatg | 540 |
| gtcttccttc attctcataa aagttgcatc atgatcagcc cagaaagcta tttctatctt | 600 |
| taagaatcca ttttttgttct tcatatttat ttttctttc ggataatca tcaaatttct | 660 |
| ttttgaactt cttaatctca gttctttttt acgggtctgt tttctaattt gagcactctt | 720 |
| cgttctaaat agaatgattt aaatcttcga tttcttttat ctaaatgact accaattaaa | 780 |
| tctatttctt ctcgtgattt tgaatacttt tcttccacac aaatgtatat ctattggcat | 840 |

-continued

```
tagcttctac ttatgtacca tcaataaaaa ttgaattatt atcaataaga ttttgcttta    900
aacattgact atggaactga ataaataaag attcaattaa cgcatcagta ttaggattca    960
ctctaaaacg attaatagtt ttataagaag gtgtttgatc ttgagctaac cacatcattc   1020
gaatactgtc atgaagtaat ttctctattc tacgaccaga aaatacagat tgagtatatg   1080
catataagat gatttttaac atcattttg gatgatagga tgttgcgcca cgatgatgtc    1140
tgaattcatc gaattcgcta tcaggtatcg tttcaacaat ttcatttaca tatcgcgaaa   1200
tatcatttta aggaattcta acagaagttt ctattggtag tgtaagttgg gcaaagtgtc   1260
ttattttttt aaagtatgta aaagtaaaat tacatgttaa tacgtagtat taatggcgag   1320
actcctgagg gagcagtgcc agtcgaagac cgaggctgag acggcaccct aggaaagcga   1380
agcattcaat acgaagtatt gtataaatag agaacagcag taagatattt tctaattgaa   1440
aattatctta ctgctgtttt tttagggatt tatgtcccag cctgttttat tttcgactag   1500
tttggagaat ttattgacat tcacattatt taaacggcaa caaagattgt tttatttga    1560
taggcattat atggtgttaa aaatttgca tgaaaattaa aaaatgcttc gttcaggaag    1620
gtgtcgtaat ttacctattt gctgaatgaa gcattttatt tttaaatatg atagccaata   1680
taacaagcta taaatccaat gatgaattgt aaaagtgaat aattgagaaa aaggttaata   1740
tcaaattttg gtgtcatcat taatgtaagt tccttggcta acgttgagaa agttgttaag   1800
ccacctaaaa aaaccggtga caaagaacgc agggaaccat gagattgaaa ttgataggcc   1860
tatagttaat ccaattaaaa aactaccaac tagatttact atcaatgttg cgataggtaa   1920
ctttgaagta aatttatgat taaaataatc agtaatggca cttctagcaa ttgcgccaaa   1980
accgccgcca atcatgacta aatgattga tatcatgata aaccaccacc tagttttata    2040
ccgacgtaac ataacaaaat accaaagaca taacttgtta cagcatatag tagtaaagtt   2100
ataaattgtt gatgatcaaa catatgtatt aattctaatt gaaatgttga aaaagtcgtt   2160
aaagcaccaa gaaaaccagt cgtaatagct tttttaggg tcggatggtt tgaaaaaaat    2220
gcaattgtta aggctgttag caatcccatt acaaaggcac cagtcaaatt ggctatcagt   2280
gttccgattg gaaaacctcc gtcagtattc agaaaagaaa tgaggtaacg taataaagcg   2340
cctaaagcac caccgataaa aatatataca tattgcattt ggttcacctc gaaaagaagt   2400
agtttgaatt taaaaaagag gttttggcaa cacgacgaca aaaattgtcg atgcattatc   2460
aaacctcatt atatgttata tcttgttgta taactatagc gattagatgc atagttatga   2520
tttcgaaaat ctaatatttt ttatacgcaa caacgtcatc aaattgtttt actcattata   2580
gcatgataca ttgtattgtt ttgtattaac gctacattga catttatct tttttaaata    2640
aaaccgaatg tacgacaatt gaaaagatat gtactaaaat aacaattaga ataatccaag   2700
gcaaactttt actcgcaatt ctaatccaat ctgcatcagg ctttagtgat ttaattgaac   2760
gatctgcaaa aattatagac aaaattagta caattgagtt aataacactg cagaaaagta   2820
ttaatttaat aaaagaatta aaaaatccac ttaggaaaac gttatttgta ttaaagaaaa   2880
agctt                                                               2885
```

<210> SEQ ID NO 4
<211> LENGTH: 8654
<212> TYPE: DNA
<213> ORGANISM: Staphylococcus epidermidis
<220> FEATURE:
<223> OTHER INFORMATION: Designated as SE-22
<220> FEATURE:
<221> NAME/KEY: misc_feature

```
<222> LOCATION: (1564)..(1564)
<223> OTHER INFORMATION: n = a or t or c or g

<400> SEQUENCE: 4
aagcttgttt tattgcttag ttatatttcc aataacactc attttatatg tacgtattgc    60
caaaaaaat tatctataca gtaataagta tgaaatgaga actggaataa tcattggtat    120
tattgcttta attctagtaa ttatgcaagg gtttcacttt aactgggcta ttattcctat    180
ttctatctat ggtcatcagt ttgtattttt cgctggaatt attttaagtc ttgttggtat    240
attctttaaa cgtatagaat tgtaggagt tggcttacta ttttgtcaaa aacatagatg    300
caatggtaac tgacccggaa attgcacagt ttttctcttt agcaatttgg attatacttg    360
ttgtgctaat cattttttat acgatacgtt tatctgaacg cactaaatca tcatcatata    420
caaagattta aactcagaaa atatgctaga catatctttc tgagtttttt aatttattaa    480
aatatatcat tgtttacca tataagtttg ttttagaaaa tgaatcacta ttttaatata    540
caaataattt aattacactg aaaataacct aaaagcgtaa cactatttta atatgggtat    600
ataaatgact aaagggaggt gccaagatga ataaaattca aatttgtaat cagattgaac    660
ttaactatat tgatgaaggc gaaggcatcc ccatcatttt aattcatgga ttagatggaa    720
acttggcagg atttaaagat ttaaaaaatg aactcaagaa gcagtataga gtaattactt    780
atgatgtcag aggtcatgga aaatcttcac gaacagaatc atatgaatta aaagatcatg    840
ttgaagattt aaatgattta atgggagcat taaatatcga ttctgcacat attttaggac    900
atgatatggg gggcatcatt gcgagtgaat ttactgaaaa atatcaatat aaagtgatta    960
cattgacaat tgtttcggcc aaaagtgaag acattgcaaa tggtttcaac aaattaatgg    1020
ttgattacca agaagaatta gcaggcttta ataaatctga ggcaatgatt attttattct    1080
ctaaattatt taagagaaa gataaagcaa tgaaatgggt atcaaagcca aaaattatac    1140
aatagaccaa ctccggaaga aagtgcaatt gcagtacgtg cattgcttaa tattaaagat    1200
ttaactcgtg ttcatcataa tgtgtccata cctactttaa ttgtgaatgg taagtatgac    1260
ccactcatac aaaataaaag tcattatgat atggatcaat attatgatca agttacaaaa    1320
attgtatttg ataattcagg acatgcacca catatcgagg aaccagaaaa attcctgaaa    1380
ctctacttag attttgttag ttaaaaaata agaacataaa taaaaaccct taaatgatta    1440
ttgtcggaaa atcatttgag ggttttgtag tagcagtaaa gtttggactc agatcactat    1500
cgtattaact taataaaaga gtaaaacagt cttatctttc ataagtgaaa gaaatatctg    1560
tttnactccc tagccattat acttcatttc attatttgct tctgtgatac ggttgtttac    1620
tcgtttaagt aaatcatcga ttttttttacg ctgcttagaa tctactaaga ttaaaacagt    1680
tctttcatcg tgttcattac gttttttatt aaagtaattt tcttgagata aattttttaac    1740
agctttaaca acttgaggtt gtttataatt taagtgattg ataatatctt taagataata    1800
ttcctcttct ttattctcac taatataagt taatactgca aattcttcaa agctgattga    1860
gaattctttt ttaattattc ctttttaatct gtcagcataa gtgaccatag ctaataattc    1920
aaagcagtca ttgattttg aaatagccat taatgaaacc tccctattta tatcatatcc    1980
ataaatctta aaacccatct ttttaaattt aaagatagtt aattatatta ttgaattaag    2040
attacttgga tactataccc taatttatta atttatatct attttttctta tgaaaatacg    2100
aaagtgtccg tcataatata gtattaattt aaatttaaag aatatattta atgctatatt    2160
atttagttaa ttataactaa ataaaattaa gaagtaaaca aataagtgtt tataaaacaa    2220
```

```
attatctttt aaagtttata cttgaattag caatgtagca tttgctatat tcaaaaaaat    2280
aagattgttt ctaattttcc ttaatttaat aaaaattata ctaaaaagaa tactttttgg    2340 aaagaattt  actaacattt tttatatata aatgtttatt aatttagaag taggattttt    2400 aacaacttt  tcatctatca ataagccttt agttatatta atatacccac ttttttaaact  2460 ctttttgtat gttacttctc tttttgtaga attaaaacat agcgttttg aacaatagct    2520 gacgtaggta actctatgtc atttgaggct aatttgattt taaagtgtgt tccaatttga    2580
tgattgggtt gtgtagaaag taaaatgtcg taatatgaga cgccattttt tattttgat    2640 ggtatattcg aaatttcttt aattttacta gtaaattgag tgttgtcact agatgttaca    2700
gaaatatttt gatttatttt taataaattc aactcagatt ctgatatatt agcacgaata    2760
atacgttcgt tgctattaat ttgcactatc ttttcgtttg gttttgaagg atagaatta    2820 atatatgaaa tacttccatt aattggtgaa aataaagtgg atttaattga ggatttagtt   2880
tgaatcattt gtaattttag ctgattaagg aatgaataat aatgtaaatc attttagaa    2940 tttaaagttt tgttgttacg ttcattacta agtgtatttt ggagttcctc atataaatga    3000
tctttttcat aattgtaata ttctaacact ggagtgtttt tagatacttt gctatgattt    3060
tttactaaaa gttttggag  ttgtcctaaa gtgggagtgt agtagaaaat atagctgtta    3120 agagggctt  gtataccagt tgttgaaagg agtaatttgg gctttgcttt tatagttttt    3180 atattttaa  tatcttctgt tttagaagtt aatttagaga aagtaatgta actaaaacta    3240
caagttgtga gaatgaaaat gaatagtaat gaagaaataa cgatgcgttg cttggtcatg    3300
gatgttcacc tcataatatt attgtgaggt tattatacac tattatttta aatgaaatat    3360
attaatttta aataagcatt acttttggtt tgtatattgt tttatttcaa aaaataaagt    3420
aaatcaattt aataaattga aaaatagaag gctatctta  attttaaaat atatgattct   3480
acataaatgt tactataaga agaatcactc ataaaaactg ccaacaaaga caaaatctt    3540 gttggcagtt cgaaatagac atttatttgt atgaggaatc tacattaata taagcggata    3600 attttattc  agaataagga atttaaaata atcgtaataa aataatacct atagctatac    3660
ataataatcc acctaactta cgtgatgtta ttttgttttt aggtgaaccc aacaaaccga    3720
aatgatcgat aataataccc ataatcattt ggcccatcat agcaattata gtagttaaag    3780
ctgctcctaa gaaaggcatt aaaataatat tagatgttac gaatgccatt cctagtatcc    3840
ctccaataaa ataaatagat ttaatcttac ctagtgtttt atgagtagat gatattttca    3900
gactacgatt aaatactaat gttaatataa ataacgctat tgtaccaacg ctaaatgata    3960
tgagtgaagc aaatatggat gagtgtgtgt gttgagccag tgtgctgttg attgttgttt    4020
ggattggcgg acgaaaccaa atacgaatcc aataagcaac cagaatacta ttggtgtatt    4080
cttatgtcta ttaacaggat gtctacgaac ataattcata aatataattc cagtaattaa    4140
aaatataatt ccaacacctt taaataatgt aaaagattgt tgatgggcgc ccaataatcc    4200
aaatgtatca atgattacac ccataataat ttgccctgta accgtaataa caacagtaag    4260
tgctgcgcct aatcttggta ataataataa gtttccagtt aaatagataa cacctaatag    4320
tcctcctagg acccaagtat agttaagtgt ttgcttagaa aagaattctg gtgttaatac    4380
ttgtggatga ataatgatat taagcacaag taagcatatt gttccgacag caaagatat    4440 ggttgaagca taaaagatg  aacgggtaaa ttggcttagc cttgagttga ttgaagtttg    4500
aataggaagt aacatgccaa caaaaattcc taaaagatat agaaaaaaca atgataaaaa    4560
ccaactttct caatttaata tgattatcat accattcata atcatgtttc taaaatgatt    4620
```

```
gagccataag caaagtatag aaataagttg tgaatgttcc gaggtgtcat acagccgata    4680
ctattttgat gaatcattat aataaaatgc acattaaaca agttttagaa ttaaaaaaag    4740
cgagacatca ttttgaattt gatatctcac ttcatattaa taaagaaaca atgtaaatta    4800
agttcttttt tagacttgaa caattttaaa aaatttgttc ttcgataagt cttttttatg    4860
attttagtac tttaaataaa gcgtcaaaaa taatgtttta tgaattaatt tttatcttca    4920
aatataacag ttgtcctttt atcaataagt tgtgcagcat aaattttgac aggctttccc    4980
aaactaaatc ttaaaatgtc taattctaaa atgtctaatt ctaaaagttg gttcatactt    5040
tctttaatta attgttctgt agtaatagcg ttaaaatcgg gtaatagtaa tttgacgggt    5100
ttattaagat ttgatttaaa tacgagttcc aaagttttg acatactgat gtatcctcct    5160
taaattaaag attctgtttt aacgatctcg actttgtcat actcttcgcc actgaacgtt    5220
caatgatgga acgaaaagat ttgatttgat cattagaaac aagcggatta atgttagaaa    5280
aacgacgctt atgttcgact actttacctt cagaattatg tttgatttga gtaaagataa    5340
tcgtcacttg attgacttca ttcataataa aacctccttt cactatatat atcgaaaatag   5400 attgaaaaaa aaggacacat ttttgaaaa atataggcaa atgcctttga tgtgatacaa    5460
acgtcattta tcattaatta tgaaacctgt tttagaaggt atatgaggta agtagaattg    5520
ttaagttgta aagaaaaaa ttggaacctg atatttaaaa taaccaactt aaaagattga    5580
tcagtgtcta aaattactat ttatatatga attaaaatat taagatctcc caatatgaga    5640
atgaattagt ttaagtttat cgatgattga aaaattatag cctcatggat tctatcttat    5700
ataaaataaa gttctattcc ctttttggata taaataagaa tagttacctt tttgtgatat    5760
gccaattcag aaaaaagcg acagtgcttg aatctatgta tgctcaataa actcattcaa    5820
atcaactagc aatatcaaat cataaatcgt gttgcaccat aataaggatt aaaacctgtt    5880 agttaacta atttaagaaa aacatttgat tatcttctct ttcaatcggg aatattaatt    5940
tctatcattc aacaatattt tggatatcag ataacttaag aaatattgag atttattgaa    6000
atacgatatg tttcaaatcg ccatacaatg attcacctta ataaatgatt acacttaata    6060
taaatgtaaa aagaaaagga ggggttaaat gagtttagta tatcttatgg cgactaattt    6120
attagtcatg ctcatagttt tattcactct gagtcatcgt caactaagaa aggttgcggg    6180
ctatgttgca ttaatagctc ctattgtgac atctacatat tttattatga aaataccaga    6240
tgtgattcga aataagttta ttgctgttcg attaccatgg atgccttcaa ttgatattaa    6300
tttagattta agattagatg gtttaagttt aatgttcggc ttaattattt cgctaatagg    6360
tgtgggtgta tttttttatg ctacgcaata tttatcccac agtacggaca atcttcctag    6420 attttttcatc tatttactat tatttatgtt cagtatgatt ggcattgtaa tagctaataa    6480
taccatctta atgtatgtat tttgggaact cacaagtatt tcctcattct tgcttatatc    6540
ctattggtac aataatggtg aaagtcaatt aggcgccatt caatctttca tgattacagt    6600
gtttggtggg ctagcgttat taacaggatt tatcatttta tatatcatta caggaacaaa    6660
cacaattact gatatcttaa tcaacgcaat gcaatttcac gacatccttt atttataccca   6720 atgattttga tgctattatt aggtgctttt accaaatctg cacaatttcc gtttcatatt    6780
tggttaccaa aggccatggc agcacctaca ccagtaagtg cttatcttca ttcggcaaca    6840
atggtaaagg ctggaatctt tttactattt agatttacac ctttattggg acttagtaat    6900
gtttatattt atacagtgac atttgttggt ctaataacta tgttatttgg atctttaact    6960
```

```
gctttacgac aatacgactt aaaaggtata ctcgcttatt ctacaataag tcaattaggt      7020
atgattatga caatggtagg tctaggtggc ggttatgctc agcacacatc agatgaattg      7080
tctaagtttt atattttagt tttatttgct ggcttattcc atttaatgaa tcatgcggtt      7140
tttaaatgtg cattatttat gggcgttggt atcattgatc acgagtccgg aacacgtgat      7200
attcgtttgc taaatggtat gcgtaaagtc tcccctaaaa tgcatattgt catgttgctc      7260
gctgcattat ctatggcagg tgttcctttt taaaatggct ttttaagtaa ggaaatgttt      7320
ttagattcgt taactaaagc aaacgaactt gatcaatatg gcttcgtatt aacgtttgtg      7380
attatttcaa taggtgtcat cgcgagtata ttgactttta cttatgcact ttacatgata      7440
aaagaaacat tctggggaaa ttacaatata gaaaaattta acgtaaaaca aatacatgaa      7500
ccatggctat ttagtttacc agctgtgatt ttaatgttac tcattccagt tatcttcttt      7560
gttccaaacg tttttggcaa ctttgttatt ttgcccgcaa ccagatctgt atctgggata      7620
gggcggaggt tgatgcattt tgtgccacata tttctcagtg gcatggtgtg aatctccatt      7680
aattttaaga tagtgtatat attggactat tttagctcta gtgtgattgg aaagaggtta      7740
cgcatcaaat aatcaaaagt gctcgattac agtggctatc ggaaatttat agagaatttg      7800
aattatactc agcccgtggt atacgtgcat tgatgaataa taaattgaat tattacatca      7860
tgattacatt atttattttt gtagctattg tagttatgga tatttgactg tgggttttcc      7920
tcatgtactc agcttcatat tagttctttc ggaccgttgg aagttatctt atcagttgta      7980
acattgatta tcggcatttc attaatcttt attcgtcaac gactaacgat ggtggtattg      8040
aatggaatga ttggattcgc agttacatta tatttattg caatgaaagc tccagattta      8100
gctttaacac agtagttgt tgaaactatt acgacaatct tatttattgt tagttttcg      8160 agactaccta acatccctcg agttaaggca aatttaaaaa aagagacctt caaaatcatt      8220
gtgtcacttg ttatggcatt gacggtggta tcacttattt ttgttgctca acaagcagat      8280
ggtatgcctt caattgctaa attttatgaa gatgcatatg aacttacagg tggaaaaaat      8340
attgtcaatg ctatactagg tgacttcaga gctttagata ctatgtttga aggactagtg      8400
ttaatcatag ctggattagg tatttatacg ttacttaatt acaaagatag gaggggcaa      8460 gatgaaagag aatgatgtag tacttaaatc agttacaaaa attgtagtgt ttattttgtt      8520
aacatttgga ttttatgtat ttttttgctgg ccataataat ccaggtggtg ctttattgg      8580 tggcttgatt tttagctcgg catttatctt aatgtttctt gcctttgatg taaatgaagt      8640
gttgaaaaaa gctt                                                       8654

<210> SEQ ID NO 5
<211> LENGTH: 2362
<212> TYPE: DNA
<213> ORGANISM: Staphylococcus epidermidis
<220> FEATURE:
<223> OTHER INFORMATION: Designated as SE-3

<400> SEQUENCE: 5
aagcttcaca acttgaaaat atagcacaaa cattaaagga tttaggtaga aaacgagcaa        60
ttttaattca tggtgcaaat gggatggatg aggccacgct ttctggtgaa aatatcatttt      120 atgaagttag cagcgaaaga gcattaaaaa aatatagttt aaaagcagaa gaagtcggtt       180
tagcttatgc aaataatgac acgttgatag gtggttcacc tcaaacaaat aaacaaattg       240
cattgaatat cctaagtggc acggatcact caagtaaacg agatgtagtt ttgttaaatg       300
ctggaattgc tttatatgtt gctgagcaag tggaaagtat caaacatggc gtagagagag       360
```

```
cgaaatatct cattgataca ggtatggcaa tgaaacaata tttaaaaatg ggaggttaag      420
taatgactat tttaaatgaa attattgagt ataaaaaaac tttgcttgag cgtaaatact      480
atgataaaaa acttgaaatt ttacaagata acggaaatgt taagaggaga aagctgattg      540
attcacttta actatgatag aacattatca gttattgctg aaataaaatc gaaaagccca      600
tctgtacctc aattaccgca acgtgatctt gttcaacaag ttaaagatta tcaaaaatat      660
ggtgctaatg ctatttcaat attaactgat gaaaaatact ttggcggtag ttttgaacga      720
ttaaatcagt tatcaaagat aacatcgtta ccagttttat gtaaagattt tattattgat      780
aaaattcaaa tagatgttgc aaaacgagct ggtgcatcta ttattttatt aatagtaaat      840
attttaagtg atgaccaatt aaaagaattg tattcatatg caacaaacca taatttagaa      900
gctctagtag aagttcatac aattagagaa cttgaacgtg cacaccaaat taaccctaaa      960
attattggtg ttaataatcg tgatttaaaa cgatttgaaa ccgatgttct acatacaaat     1020
aaattactta agtttaaaaa gtctaattgc tgctacattt cagagagtgg cattcataca     1080
aaagaagatg ttgagaaaat agtagattca agtattgacg gtttacttgt aggggaggca     1140
ttaatgaaaa caaatgactt aagtcagttt tttgcctagt ttaaagttaa agaagaatct     1200
ctatgatagt taaattttgt ggttttaaaa ccgaaagtga tattaagaaa attaaaaaat     1260
tagaagttga tgcagtaggg tttatacatt atcccgatag taagagacat gtctcactga     1320
aacaattaaa atatttggct aaaatagtgc cagatcatat agagaaagta gtgtcgtagt     1380
aaatcctcaa atgtccacca taagagaat aattaatcaa actgatatta acacaatcca     1440
attacatgga aatgaaagca ttcaattaat tagaaatatt aagaaactta attcaaaaat     1500
aagaatcata aaagcaattc cagcaacaag aaatttaaat aataacattc aaaagtataa     1560
agatgagata gactatgttt attatagata caccatcaat cacatacgga gggacaggtc     1620
aaagttttga ctggaaatta ttaaaaaaaa taaaggcgtt gatttctca ttgcggtggt     1680 ttggattttg aaaagataaa acgattagaa atatattcat ttggacaatg tggttatgac     1740
atctcaactg gcattgagtc acataatgaa aaagattta taagatgac tcgaatatta     1800 aaattttga aggagacga atgattaatg aaaattcaaa cagaagtaga tgaattgggc     1860 ttttcggtg aatatggtgg ccaatatgta cctgaaacat tgatgccagc tattattgaa     1920
cttaaaaaag catatgagga cgcgaaatca gatactcact tcaagaaaga atttaattat     1980
tatttaagtg aatatgttgg tagagaaacg ccttttaacat ttgctgaatc atacacaaaa     2040
ttgttaggtg gtgccaaaat atatcttaaa agagaagact taaatcacac tggtgctcat     2100
aaaattaata acgcgatagg acaggcacta ttagctaaaa ggatgggaa aactaaatta     2160 gtagccgaaa caggtgctgg tcaacatggt gtagcaagtg ccaccatcgc tgctttattc     2220
gatatggatc ttattgtttt catgggaagt gaagatatca aacgtcaaca acttaacgta     2280
tttagaatgg aattgctagg agctaaagta gtgtctgtgt cagatgggca aggaacacta     2340
tcagatgctg taaataaagc tt                                              2362
```

<210> SEQ ID NO 6
<211> LENGTH: 5024
<212> TYPE: DNA
<213> ORGANISM: Staphylococcus epidermidis
<220> FEATURE:
<223> OTHER INFORMATION: Designated as SE-32

<400> SEQUENCE: 6

```
aagcttttg attttaaag aaaaattaa acaaggggc attgcttatg gtcaatagaa      60
gaaagatatc aattattggc gcgggacata caggtgggac tctagcattc attcttgcac   120
aaaaggaatt aggagatatt gtgttgattg aacgccagca atcagagggt atggctaaag   180
gaaaggcgtt agatatttta gaaagcggac ccatttgggg gtttgacaca tctgtacatg   240
gttcagtaaa tatagaagat attaaagatt cagacatagt ggtgatgact gcaggtatac   300
ctaggaaatc aggaatgaca aggagaagaa ttagttcaaa ctaatgaaca aatagtacga   360
gaaactgcat tacaaattgc aacgtatgca cctcattcaa taattattgt attgactaat   420
ccggttgatg ttatgacata tactgcattt aaagcatcag gttttcctaa agaacgtatt   480
attggtcaat ctggaatttt agacgctgca agatatcgaa cttttattgc tcaagaactt   540
aacgtgtctg tcaaagatgt aaatgggttt gttttaggtg acatggtga tacgatgtta   600
cctttgatta ataacacaca cattaatggg attccagtta agcatcttat ttctgaagaa   660
aagattgatc aaattgttga acgtacacgt aagggtggtg cagaaattgt tgcattacta   720
ggtcaaggct cagcatatta tgcaccagca actgctatat atgaaactat agatgcaatt   780
tttaatgatc ggaaacggtt attaccaagt attgcttatc tagagggaga atacggttgt   840
tcagatattt gtttcggagt tcctactata ataggatatc aaggaataga aaagattata   900
gaggtagata tgaataatga tgagtatcaa caactacaac actctgcgca agatgtgagt   960
gaagtcaaaa actcactaaa attcaaataa ataattatga agttctacat cttaaattgt  1020
tagattttg tgaaaattgt gtaaagggta tttttcgtt gatttataaa agcgcttttct  1080
tgatataatg aacatatatt catagaataa ggagacgatt aaaatggcta aggggacca   1140
atatcaagct catactgaaa aatatcatga gtaaaaagtc taaaaaagt tataaacctg   1200
tgtggattat cattagttt attatttaa ttacaatctt gttattaccc acaccagcag    1260
gattacctgt aatggctaaa gcagcactag ctatttagc tttcgctgta gttatgtggg   1320
ttacagaagc agttacttat ccagtttctg caacattaat tttaggatta atgatacttt   1380
tactaggttt aagtccagtt caagatttat ccgaaaaact tggaaaccta aaagtggcga   1440
cataatacta aaaggtagcg atatttagg aacgaataac gcgcttagtc acgcttttag    1500
tggttttca acctcagccg tagcacttgt agctgcagca ttattttag cagtagctat    1560
gcaggaaacc aatttacata aacgacttgc attatttgtg ctatcaattg ttggaaataa   1620
aactagaaat atagtcattg gtgctatttt agtatctatt gttctagcat tctttgtacc   1680
atcagctaca gcacgtgctg gtgcagttgt cccaatatta ctgggaatga ttgctgcatt   1740
taatgtgagt aaggatagta gacttgcttc attattaatt attactgctg tacaagcagt   1800
ttcgatatgg aatataggta ttaaaaacgg ctgcagcaca aaatattgta gccatcaatt   1860
ttattaacca aaatttagga catgatgtat catggggaga gtggttttta tatctgcgcc   1920
gtggtcaatc attatgtcta tagctctta ttttataatg attaagttta tgccacctga   1980
acatgatgca attgaaggtg aaaagagtt aattaaaaag gaacttaata aattaggacc   2040
agtcagtcat agagaatggc gactaattgt gatttcagtg cttttatatt ctctggtcga   2100
ctgagaaagt attgcatccg attgattcag cttcgattac actagttgct ctaggtatta   2160
tgctaatgcc aaagattggt gttattactt ggaaaggtgt tgaaagaag attccttggg   2220
ggacgattat agtatttggt gtaggaatct cacttggtaa tgtattactt aaaacaggag   2280
ccgctcatgg ttagtgatca acatttgttt gatgggtctt aaacatttac cgatcatagc   2340
aactattgcg ttaattacct tatttaatat attaatacat ttaggttttg caagtgcaac   2400
```

-continued

```
gagcttagcc tctgcgttaa tacctgtgtt tatttctttg acttcaacgc taaatttagg      2460
tgatcatgct attggttttg tattaataca acaatttgtg attagttttg gtttcctact      2520
acctgtcagt gcaccacaaa atatgcttgc atatggtact gggacttttta ccgtaaagga     2580 tttttttaaag acaggtatac ctttaacgat agtaggttat attttagtta tcgtatttag    2640
tttaacgtat tggaaatggc ttggtttagt gtaagtaaaa gatttaggta ttaaaatgat      2700
aattataaat gtctcgtaaa gtttaatatt ttaactttac gacacatttt ttataaactc      2760
gtggcaagtt aatcttaata gttgaaatgt atcgtataaa aaatatatga atgtaaatag     2820
aatttagtat tagagaataa caaaaaattg atgttaggtg gtaaaatcta atggctatag     2880
gtgtcatatt aaatagagtt tttaggctaa ataataatcc attatttgat tatatatata     2940
gtaataaaga atctataaat cattgttatt ttattattcc aactgaagag tttgaagaag     3000
aagcaaaaaa gaaagcacaa tactattatg ggtccataca gaagtttatg tatgaactac     3060
aacgatatga tatagaaccc tttttgatgt cttatgataa attaatagac ttttgtaaaa     3120
aacaagctat agacaaagtt gttgttgcag gtgatattat gagttatcat cacgaagaat     3180
atgacatttt acatcaaagg aaacgattta aacaagctaa tattcaagta atatcattaa     3240
gagcaaatca ttattttaac ccccgcaaaa cacataataa acaaggggaa ccatataaag     3300
tatttaccag tttttataga aaatggcgtc cttacttaat gattagagat gaatatgact     3360
atcatttaga agatatttca aaggttgtag tgaaatctca acataaaatt aaagaagatt     3420
atcattcata tggtataagt gaacgtgatg ttcaaaatcg ttggtctgaa tttttatctc     3480
aagatatcga aaattataaa gaaaacaggg aatacttgcc tgaagtatta acaagccaac     3540
taagtattta cttagcttat ggaatgatag atattataca atgttttcaa cgatttactt     3600
caaaattatg ataaaaatga acaaaattac gaaacttttta tacgtgaatt gattttttaga   3660 gagtttttatt atgtattaat gaccaattat cccgaaacag ctcatgttgc ttttaaagaa    3720
aaataccaac aattgaaatg gtcttataat gaagagaatt ttaaactgtg gaaagatggg     3780
aatactggtt ttccaattat tgatgcagca atggaggaac ttaaaacaac tggatttatg     3840
cataatcgca tgagaatggt agtttctcaa ttttttaacta agatttgtt tattgactgg     3900 atttggggtg agtcattttt caaacaaaaa ttaatagatt atgatgcagc ttcaaatgtt     3960
cacggatggc agtggtcagc ttctactgga acagatgctg taccatactt tagaatgttt     4020
aatcctataa gacaaagcga gcgttttgat aataatgcac gatatataaa aacttacatt     4080
ccaagattaa atcaggtaga tgctaagtat ttacacgata ctcataaatt cgagcaacaa     4140 ataaagggc aaggtgttga ataggtaaa gactatccta aacaaatgat tgatcacaaa       4200
gaaagtagac aacgtgtaat gtcagaattc aaagctatag attaaataaa aaagatctga    4260
acaacatgat ataggtgttc agatctttat ctagttacat aaaaaagcaa acatgaatta    4320
aaatatattc taacaaagtt aaaatataca tatatttaag atttaattta gttttcaaag     4380
gtacttccca atttgtataa cggggctcat aataaaataa ttgcatcaaa tataatccta   4440
tccctaacgg taaacacatt aataaaatag ctttagtata actccatcct atttgatgcc   4500
ataaatgacc tatcataagt tgaataatga tgagacatac cattaaaatt acttcaatta   4560
tcattggtat aatctcaccc ctttaataaa caatatgact gttgcttgta tgagcaccat    4620
taaaacgaca aatagtaacg ctttaacatc tatgattaaa aaaacctctt tcacaatttt     4680
taaaggtgca tttaataaat agacagtatg taatcttaag aatcgaccga tgtaaatacc     4740
```

-continued

```
taatccattt aagaacatta atataactat caatagtcga tttaaccata cataagacgt    4800
aaaatgtgca atttctaaaa atataagaat tgtgaggtat attgctaaga gtacgccaag    4860
tattaaatag gtgaaataaa tccattctgt gatgtttaat ccagctaaaa agttaaattg    4920
aaattggttt aagtgtatga gatcggtaat catataaaat gtgtttggaa ctaataatag    4980
aaatatgagt ccgaaaacaa taaataaggg ccattcaaaa gctt                     5024
```

<210> SEQ ID NO 7
<211> LENGTH: 9515
<212> TYPE: DNA
<213> ORGANISM: Pseudomonas aeruginosa
<220> FEATURE:
<223> OTHER INFORMATION: Designated as P2-2
<220> FEATURE:
<221> NAME/KEY: misc_feature
<222> LOCATION: (8841)..(8841)
<223> OTHER INFORMATION: n = a or t or c or g
<220> FEATURE:
<221> NAME/KEY: misc_feature
<222> LOCATION: (9111)..(9111)
<223> OTHER INFORMATION: n = a or t or c or g

<400> SEQUENCE: 7

```
aagctttcct ccagacccct caccgccgtg gagatcgacg gctgggcgat gtacagcttg      60
cgcgaggcct cggccacgct gccgcattcc acggtggtca cgaaatactt gagttgccgc     120
aaggtatagg acgccactgc aagacctcat cggcgcatca tcctccccgg gccgggcgtg     180
cgcgcctcga ttgttgtgtc cgccgcgctg caagcaagtt gcaggccgct gccgagcgtc     240
gcgcgctggc cgcggaacga ttgcccgcct gcacgataac ccagcacgac gcactttgcc     300
ggggcacgcc tggccagctt tttcttatgt cccgaggaca tttttaataa tttctcttcg     360
ccgcggcttg cgcgaccatc cttccccatc gacccatgg acagcggttc gcctcccggc      420
ggtccgggcc atgcgtgcag aaccacgacc ggcgcagacc ggcgagataa caaggagaag     480
gtggggtgtt cgaactcagc gattggcaac ggcgcgccgc gacacagcgc ttcatcgacc     540
aggccctgat cggcggccgc cagcgtccag ccgccagcgg cgctaccttc gacgccatcg     600
atccggcgag caatcgcctg ctggcgcggg tcgcggcctg cgatgcggcc gacgtcgacg     660
cggcagtggc cgccgcccgc cgcgccttcg acgaaggccc ctgggcgcgt ctcgccccgg     720
tcgagcgcaa gcgcgtgctc tgccgcctgg cgagctgatg ctggcccatc gcgaagagct     780
ggcgctgctc gactcgctga acatgggcaa gccggtgatg gacgcctgga acatcgatgt     840
acccggcgcc gcccacgtct tcgcctggta tgcggaaagc ctcgacaagc tctacgacca     900
ggtcgcgccg gccgcccagc agaccctggc caccattacc cgcgtgccgc tgggggtgat     960
cggcgcggtg gtgccgtgga acttcccgct cgacatggcc gctggaagc tcgccccggc    1020 cctggccgcc ggcaactcgg tggtgctcaa gccggccgag cagtcgccgt tctccgccct    1080
gcgcctggcc gagctggccc tggaggcggg ggtgccggaa ggcgtgctga acgtggtgcc    1140
gggcctcggc gagcaggccg gcaaggccct cggcttgcac ccggaggtgg acgcactggt    1200
gttcaccggc tccaccgagg tcggcaagta cttcatgcag tattccgcgc aatccaacct    1260
caagcaggtc tggctggagt gcggcggtaa gagtccgaac ctggtgttcg ccgattgccg    1320
cgatcttgac ctggcggcgg aaaaggcgc cttcggcatt ttcttcaatc agggcgaggt    1380
ctgttcggcg aactcgcgct tgctggtgga gcgttcgatc cacgacgagt tcgtcgagcg    1440
cctgctggcc aaggcccgcg actggcagcc gggccgatccg ctggaccgg ccagccgcg    1500 ccggcgccat cgtcgaccgc cggcagaccg ccgggattct cgccgccatc gagcgggcgc    1560
```

```
aaggcgaggg cgcgaccctg ctcgcggtgg ccgccagttg acgatcaacg gttcggacaa    1620
cttcatcgaa ccgaccctgt tcggcgacgt acgcccggac atgcagctgg cccgcgagga    1680
aatcttcggc ccggtgctgg cgatcagcgc cttcgactcc gaggacgagg ccatacgcct    1740
ggccaaggac agccgctacg gcctcgccgc ctcgctgtgg agcgacgacc tgcaccgtgc    1800
gcaccgggtg gcgcggcgct tgaatgccgg aacgtgtcgg tgaataccgt ggacgcgctg    1860
gacgtcgcgg tgccttcgg cggcggcaag cagtccggct tcggtcgcga cctgtcgctg    1920
cattccttcg acaagtacac ccagttgaag acgacctggt tccagttgcg ctgaagacgc    1980
gacggacgcg acacgactcg atgccgataa cgacaacaag aggacgatcg aatgaacgac    2040
acgccgaacg tgcgtgagcc ggccctgcgc cgcgtgctcg ggctgggacc gctgctggcg    2100
gtggccatcg gcctggtggt ttcccagggc gtgatggtac tgatgctgca aggcgccggg    2160
acggccggcc tgggcttcat cgtgccgctg ggagtggcct acctgctggc gctgactacg    2220
ccttttcctt ttccgagctg gccctgatga ttccccgcgc cggtagcctg agcagctaca    2280
ccgaggtggc catcgggcat ttcccggcga tcctggcgac cttttccggc tacgtggtgg    2340
tggcgatgtt cgccctctcg gcggaactgc tgctgctcga cctgatcatc ggcaaggtct    2400 accccgcgc gctgccgccg atgctggtgc tacggcgtgc tcggcctgtt caccctgctc    2460
aacctgctcg gcatcgacat cttcgcgcgc ctgcagagcg cgctggcgct gctgatgatg    2520
atcgtcctgc tggtgctcgg cctgggtgcg gtgagcagcg accacgcttc cgcgcagacc    2580
gccctggcga gcgctggaa cccgctgggg gtaagcgccc tggcgctcac cgcgatggcc    2640
gtgtggggct tcgtcggcgc cgagttcgtc tgcccgctgg tggaggagac gcggcgtccg    2700
gagcgcaaca tcccgcgttc gatgatcctc ggcctgagca tcatcttcct gaccatcgcc    2760
ctctactgct tcggtgcgct gctgtgcatc ccgcaggcgg aactggccgg cgacccgctg    2820
ccacacttcc tcttcgccaa ccgcgtgttc ggcgagtacg ccagctgtt cctggtgatc    2880 gccgcgatca ccgccacctg cagcaccctc aactcgtcgc tggcggcgat ccgcggatg    2940 ctctacggga tggcgcagaa cggccaggcc ttcccgcaat tcaagcagct cagccggcgg    3000
gcgcgcacgc cctgggtggc ggtgctgttc gtcgccgcga tcaccggcct gccgatcctg    3060
atcctcggcc aggacccgga ctcgatcaac ctgctgctgc tcgccgccgc gctggcctgg    3120
ctgctggcct acatcatcgc ccacgtcgac gtgctggccc tgcgccgtcg ctatccgcac    3180
atcgcccgtc cgtttcgcac gccgttctac ccgctgccgc aactgttcgg catcgccggg    3240
atgatctacg cggtggtcca cgtctcgccg accccggaaa tgaccggacg gatcttcgcc    3300
agcgccggcg tggtgctcgg cgtggtctcg ctggtgccgg tggtgtggat caagggcgtg    3360
atgcgcaagc ccctcttcgt acccgaaccg ctcgagacgg ccggtgagac tgcccagggc    3420
aagtccgtcg ccctcgatcc cctgcaatcc cttcggcctg acgcgccaag ggaacaagga    3480
gaacacagac gatgaccgct cagctcaacc cgcagcgcga caccgcgac taccagcaac    3540 tggacgccgc gcaccacatc cacgccttcc tcgaccagaa ggcgctgaac cgcgaaaggc    3600
ccgcgggtga tggtccgcgg cgatggcctg cagctctggg acaacgacgg caagcgctac    3660
ctggacggca tgtccggcct ctggtgtacc aacctcggct acggccgcca ggacctcgcc    3720
gccgccgcca gccgccagct ggaacaactg ccgtactaca acatgttctt ccacaccacc    3780
cacccggcgg tggtggagct ttccgagatg ctccttcagcc tgctgccgga ccactacagc    3840
cacgcgatct acaccaactc cggctccgag gccaacgagg tgctgatccg taccgtgcgg    3900
```

```
cgctactggc agatcctcgg caagccgcag aagaagatca tgatcggccg ctggaacggc    3960
taccacggct cgaccctggg cagcaccgcg ctcggcggga tgaagttcat gcacgagatg    4020
ggcgcatgct gccggacttc gcccacatcg acgaaccctc ctggtacgcc aacggcggcg    4080
agctgagccc ggccgaagtt cggtcgccgc gcggcgctgc aactggagga gaagatcctc    4140
gaactgggcg cggagaacgt cgccgccttc gtcgccgagc ccttccaggg cgccggtggc    4200
atgatcttcc cgccgcaaag ctattggccg gagatccagc gcatctgccg gcagtacgac    4260
gtgctgctgt cgccgacga agtgatcggc ggcttcggcc gcaccggcga atggttcgcc    4320
cacgaacact ttcgcttcca gccggacacc ttgtccatcg ccaagggcct gacgtccggc    4380
tacatcccca tgggcggcct ggtactcggc aagcgcatcg ccgaggtgct ggtggagcag    4440
ggcggggtgt tcgcccacgg cctgacctat tccggccacc cggtggcggc ggcggtggcc    4500
atcgccaacc tcaaggctgc gcgacgaggg cgtggtcacg cgggtcaggg aggagaccgg    4560
cccctacctg caacgctgcc tgcgcgaggt cttcggcgac catccgctgg tcggcgaggt    4620
ccagggcgcc ggcttcgtcg ccgcgctgca gttcgccgag gacaaggtga cccgcaagcg    4680
cttcgccaac gagaacgatc tggcctggcg ctgccgcacc atcggcggct cgaggaggg    4740 cgtgatcatc cgctccaccc tcggccgcat gatcatggcc ccggcgctgg tggccgggcg    4800
tgccgagatc gacgaactga tcgacaagac ccgtatcgcg gtggatcgca ccgcgcgcga    4860
gatcggcgtg ctctgacgcg ccccggcggc ccggcctcgg ccgggtcgcc tgcgacacgg    4920
agcgtccccc cataacgacg atgcggcgcc tggcgaccgc gcgcggaacc gtttcggcct    4980
ctggcggcaa ctgcctaagc aacatcacaa caatgccaat cggctgtggg agtgttccat    5040
gttcaagtcc ttgcaccagt acgcacacgt gttttcccgg ttgtccctgt tcgtcctggc    5100
gttcgccgcg gcggcccagg cgcagagcca gagcctgacg gtgatctcct tcggcggcgc    5160
gaccaaggcc gcccaggaac aggcctattt caaacccttc gagcgaagcg gcggcgggca    5220
ggtggtcgcc ggcgaataca acggcgaaat ggccaaggtg aaggccatgg tcgacgtcgg    5280
caaggtcagc tgggacgtgg tcgaggtgga gagccccgaa ctgctccgcg gctgcgacga    5340
ggggctgttc gaacgcctcg acccggcgcg tttcggcgac cccgcgcagt tcgtccccgg    5400
cactttcagc gagtgcgggg tggccaccta cgtctggtcg atggtgatgg cctacgactc    5460
gacgaagctg gccagggcgc cgcagtcctg ggcggatttc tggaacgtcc gcgagttccc    5520
ccggcaagcg tggcctgcgc aagggcgcca agtacaccct ggaagtgcg ttgctggccg    5580 acggggtgaa ggcggaggac ctctacaagg tactcgccac cccggagggg gtcagccgcg    5640
cctttcgcca agctcgacca gctcaagccg aacatccagt ggtgggaggc cggcgcccag    5700
ccgccgcaat ggctggcggc cggcgacgtg gtgatgagcg cggcctacaa cgggcgcatc    5760
gccgctgcgc agaaggaggg ggtgaaactg gccatcgtct ggcccggcag tctctacgat    5820
ccggagtact gggcggtggt gaagggcacc ccgaacaagg cgctggcgga gaaattcatc    5880
gccttcgcca gccagccgca gacgcagaag gtgttctccg agcagatccc ctacgggccg    5940
gtacacaagg gcaccctggc gttgctgccg aagacggtgc aggaggcgct gccgaccgc    6000 gccggccaac ctcgaaggcg cgcgggcggt ggatgccgag ttctgggtgg accacggcga    6060
ggagctggaa cagcgtttca atgcctgggc gcgcgctgag cgctgcgcgt cggcaaaaaa    6120
aatgacgggc cccaagtcgt ccgggcccgt cgggtcaaag cgctgacggg gtgatcagcg    6180
cagctcttcc aacaacccct gcagataccg acagccctcg gtatccagcg cctgcaccgg    6240
aaggcgcggc gcccccacct ccaggccgga gaggcccagg ccggccttga tggtggtcgg    6300
```

```
caggccccgg cggaggatga agtcgagcag cggcaactgc cggtagaaca gcgcgcgggc      6360
cttctccagg tcgccgtcga gcaccgcctg gtagagctgg ccgttgagcg tcgggatcag      6420
gttcggcgcg cgcgctgcacc agcctttcgc gccggccacg aaggcctcca gcgccagcgc    6480
gttgcagccg ttgtagaagg gcacccggcc ttcgccgagc aggcgcagct tgtgcatgcg      6540
ctggatgtcg ccggtgctct ccttgaccat ggtcacgttg tccacttcgc ggacgatgcg      6600
caggatcagt tccaccgaca tgtcgatgcc gctggtgccc gggttgttgt agagcatcac      6660
cggcacgccg atggcttcgc caaccgcgcg gtagtgctgg aacacttccg cctcgttgag      6720
cttccagtag gagatcggca ggaccatcac cgcctcggcg ccgagggatt cggcgaactg      6780
cgcgcggcgc acggtcttgg cggtggtcag gtcggagacg ctgacgatgg tcggcacgcg      6840
atgggcgacg gtcttcaggg tgaagtcgac cacctcgtcc cattccgggt cgctcaggta      6900
ggcgccttcg ccggtgctgc cgagcggggc gatggcgtgc acgccgccgt cgatcaggcg      6960
ctcgatggag cggccgaggg ccggcaggtc gagaccgccg tcggcgccga agggggtga      7020 tggtgtagcc gatgatgccg tggatggatg cggacattgg atgtacccgt gacattgagt      7080
gggaaatgcc aggacggacc tggtgggaaa ggtcgttcag ctcaggcagt cgctgttgcg      7140
cggcaggcag cgccgggcgt agtagttgaa tgcggcgccg tggcgcttcg gggtggagat      7200
ccagtcgtgg gcctcgcgcg ccagggccgg cgggatcggc ttgatctctc cggcggccat      7260
cgccagcaac tgcatcttcg ccgcgcgctc gagcagcacc gcgatcacgc aggcctcctc      7320
gatgctcgca ccggtggcca gcaggccgtg gtgggagagc aggatggcgc gcttgtcgcc      7380
gagggcggcg gagatgatct cgccttcctc gttgcctacc ggcacgcccg gccagtcctt      7440
gaggaaggcg cagtcgtcgt atagcgggca aaggtccatg tgcgagacct gcagcggtac      7500
ttccagggtc gacagcgcgg cgatgtgcag cgggtgggtg tggatgatgc agttgacgtc      7560
cgggcgggcg cgatagaccc agctgtggaa gcgattggcc ggattcgcca tgccgtgccc      7620
gtggaggacg ttgaggtctt cgtcgaccag cagcaggttg ccggcgctga tctcgtcgaa      7680
gcccaggccc agttgctggg tgtagtaggt ccccgcctcc gggccgcgcg aggtgatctg      7740
cccggcgagc ccggagtcgt ggccggcctc gaagagaatc cggcaggtca gggccagctt      7800
ttgccggtca gtccacgtat tatcgccgag gctgcttttc atctgcttca gcgcgtgctg      7860
gatcagttga tccttgggta attccagtgt cgtaaccatg cgaggttcct ttgacggagc      7920
gagtcggggg aaacgccagg cagttgcgcg ccacgcaacg acccgctgt aaatgacacg      7980 gatcaagtta tatgacacaa agtgtcattt agcaagagag aagtttcatc gccatcggga      8040
gaaggctgtc ctcaatgtcc atgcgcttga aattgctgaa aaaaaactc ggggtcacgc      8100 tggagaccct ggccgacaag accggcctga ccaagagcta cctgtccaag gtcgagcgcg      8160
ggctgaacac gccgtccatt gccgccgcgc tgaagctggc gaaggcgttg aacgtgcagg      8220
tggaggagct gttctccgag gaaagcgacg tgtcgacgg ctacagcatc gttcgtcgcg      8280
accagcgcaa gtcgctgtcc agcggcgacg acggcccggc ctacgcctcc ctcgtcgcag      8340
cagatcggcg cccgcgcgct gttgccgttc atcgtccacc ccccgcgcga tttcagtcac      8400
tcgacgttca aggagcacct cggcgaagag ttcatcttcg tccatgaggg ccaggtcgag      8460
gtcgacttca tgaaccagcg gatcatcctc gagcgcggcg acgccctgca tttcaacgca      8520
cagaagccgc accgcatccg ctccctgggg gagacccagg cggaattgct ggtggtgatc      8580
cacagcgacg aatgaggcga cggcttcggt cgatcggatg cttgctaacg ttctgttcga      8640
```

```
ttatcgaact gttaatcgat tatcggattg tgagccctcg gaccccggcg taaggttctc    8700
gtcacgtgcc gtccaggcag cgcacaacaa gacgagaccc gaccgatggc tgaaatcctc    8760
tccctgcgcg aacggtgcga cgcttcgtcc acgatggcga cagcgtcgcc ctcgaaggct    8820
tcactcacct gatcccgacg nccgccggcc acagctgat  ccgccaggc  aggaaagacc    8880 tgacgctgat ccgcatgact cccgacctgg tctacgacct gctgatcggt gcaggctgcg    8940
cgaagaagct ggtgttctcc tggggcggca acccggtgt  cggttcgctg caccgcctgc    9000 gcgacgcgt  ggagaagggc tcggccgcaa ccgctggaga tcgaggaaca cagccacgcc    9060
gacctcgcca acgcctattt tgccggcgcc tccgggctgc ccttcgcggt ntgcgcgcct    9120
acgccggctc cgacctgccg aaggtcaacc cgctgatccg cagcgtcacc tgcccgttca    9180
ccggcgaagt gctggcggcg gtgccctcgg tgcgtccgga cgtcagcgtg atccacgcgc    9240
agaaggccga ccgcaagggc aacgtgctgc tctggggcat cctcggcgtg cagaaggaag    9300
cggccctggc ggcgaagcgc tgcatcgtca ccgtcgagga tcgtcgac   gaactggacg    9360 ccccgatgaa cgcctgcgtc ctgccgagct ggggcgctca gcgccgtgtg cctggtgccc    9420
ggcggcgcgt atccgtccta tgcccacggc tactacgagc gcgacaaccg cttctaccag    9480
gactgggacc cgatcgcccg cgaccgcgaa agctt                               9515

<210> SEQ ID NO 8
<211> LENGTH: 2291
<212> TYPE: DNA
<213> ORGANISM: Enterococcus faecalis
<220> FEATURE:
<223> OTHER INFORMATION: Designated as EF-1
<220> FEATURE:
<221> NAME/KEY: misc_feature
<222> LOCATION: (2096)..(2096)
<223> OTHER INFORMATION: n = a or t or c or g

<400> SEQUENCE: 8
aagctttaga taatgataaa cgcgtgtatg tgaatgtcca gccgattcaa tcgcctactg      60
gagaaacagt gattggtgtc ctttatgtga aaagtaattt agaaaataaa taccaagaaa     120
ttactaacac agcaagtatc tttttcactg cttctattat tgccgcagca atctcgatta     180
ttgtgaccct actgattgca cgatcaatca cgaagccgat tggtgaaatg cgcgagcaag     240
ccattcgaat cgctcgtggt gattacgctg gaaaagtaga agtccatgga aaagatgaat     300
taggccaatt agcagaaaca tttaatcaat tatcagaacg gattgaagaa gcacaagaaa     360
caatggaagc agaagaatcg tttagatagt gtcttaacgc atatgacaga tggtgtcatt     420
gcgacggatc gccgcggaaa ggtgattacg attaatgaga tggcccttc  attattaaat     480 gtaaaaaatg aaaatgtgat tgggaccctcg ttattagagt tgttagatat tgaagaagat     540
tacacattgc ggaagctgtt agaagagcca gatgaactgc tgattgatcg ctcaacgtct     600
gatcgtgaag aagaccaaat gattatccgg gtagacttta cgatgattcg tcgggaatca     660
ggatttatta ctggcttagt ttgcgtactt catgacgtca cagaacagga aaaaacgaa      720 cgggaaagac gggaatttgt ttccaatgtt tctcatgagt tgcgacgcct ttgacaagta    780
tgcgtagtta tatagaggct ttgagtgaag gagcttggga aaaccctgag attgcgccga    840
atttcttaaa agtcacgtta gaagaaaccg accggatgat tcgtatgatt aatgatttgt    900
taaatttatc tcggatggac tctgggaata cacatcttca attagagtat gtgaattta     960 acgaattgat taatttgtc ttggatcgct ttgatatgat gattgaaaat gagcaaaaaa    1020
attacaaaat tcgccgtgaa tttactaaac gcgatttatg ggtagagtta gatacagaca    1080
```

-continued

```
aagtaattca ggttttgac aacattttga acaatgcgat taagtattcg ccagatggcg    1140
gcgtcattac ctgccgacta gttgaaacac ataataatgt cgtctttagt atctcggacc    1200
aaggtttggg catccctaaa aaagatctcg ggaaagtctt cgagcgtttt tatcgtgtgg    1260
ataaagcacg tgcgcgagca caaggtggga ctggtttagg tttagcaatt tctaaagaag    1320
taattcgggc ccataacggg agtatttggg tggaaagtac agaaggtgaa ggatcaactt    1380
tctatatttc actaccatat gaaccttatg aagaggattg gtgggaatga tgaaaaaatc    1440
agaatggatt acaagaattg gcttgatttt gatggtcatt ttaagtatat attttttcagt    1500 caatatctgg ctgaattctg ccaaaaaaat accagaaatg aagtcgggaa gccaagtcac    1560
aacagctgtc aatgaaaaag ccattggcga tgtctattta cctttgcaat tgattcgaat    1620
agccgatgga aaagcgatgc aaagtaatcg tgaaacatta attagtaatg ttcaaaatga    1680
tattaaaatg gctacgtttg gtaaattgac acaagttgtg acaaaaaatg cagagcaact    1740
taagcgctac aaccaaatgg aacaaggcat tgaacttctt tatcaaggtc ccttttaat    1800 ctcggactat gcttcgattt ataatctatc cattaatttt actaacttta atgagttgac    1860
ggaccagtat tttacgaaaa ttcaattgga ttttaacgaa aataagatac gttttttaga    1920
ttatgatcaa tccaacgtct atgaagcgcc catgactgtt aataaggcgc gcttaatggg    1980
aattatcaat aaagagggat tgcaatatca agacgtttcc gaaaatacgc taaccaaaca    2040
aggacaatgt tatttaacca atgatatgaa gttgaaaaag tacagttata tcttanttcg    2100
caaccagtta ctcgttttag gaatgctttt ttcaatgaaa cggaagatat ccaaaccaat    2160
gaagacagtc aagacttaac ctatacgagt aaagaagaac gattgtttgc agaagaaaaa    2220
ctggggaaaa tcgattttaa agggaccttg ccagaagaga ataaacggga ctcaatctat    2280
aatcaaagct t                                                        2291
```

<210> SEQ ID NO 9
<211> LENGTH: 2441
<212> TYPE: DNA
<213> ORGANISM: Enterococcus faecalis
<220> FEATURE:
<223> OTHER INFORMATION: Designated as EF-27
<220> FEATURE:
<221> NAME/KEY: misc_feature
<222> LOCATION: (1040)..(1040)
<223> OTHER INFORMATION: n = a or t or c or g

<400> SEQUENCE: 9

```
aagcttctgc gctaggaacc agcccttaa ttacatctcc ccatactgga tttgacaatg    60
ccacttgata agcaaaaatc acaaaaataa caacaattaa agcaacaaca atagcttcaa    120 ttttttctaaa accaattttt gtcaataaca acaaaagtaa aacatcaaat accgtaatga    180
agacagccag acctaaagga atatgaaata taaatataa ggcaattgcg cccccgataa    240
cttcagcgat atctgtagcc ataattgcta actctgttaa aatccataat acaataccta    300
acgtcttact agttctagca cgaatcgctt gtgctaaatc catctgtgaa caatgcctaa    360
tttagcagcc atatattgga gcaacattgc aatcaaactg gaaattaaaa taatcgacat    420 caataaaatat tgaaaatttt gtccccccagt aattgaagta gaccagtttc ctggatccat    480
ataccccact gctaccaatg ctcctggacc tgagtaagca ataacgtttt tccaaaaact    540
catattttta ggcacgtcga tggtgccatt aatttcttca agcgaaggac catttgcata    600
ttcaatcaaa tgatgtcttt gctttggttc atgttcttct gaattttca attcaattcc    660
```

```
ttctttcgtt ttgcaataat tttaaaaggc ccttcccgtt agaaggttaa cctctagtat      720 atttttaggta cacctaaaat atactgctaa aaataacaaa atgcaagact tgaaagaaaa     780
ttttgacagt gtaaaaatag attgtcgtaa atgtgcgatc ttaaagtttg aagaaatcag     840
ggtagctggt agttgattat cttaagaagt agaaaataag ggacctaagt catttcggct    900
taggtccctt attttatttt tattcggtta ttctattaag aatggatgct acaatttctg    960
tcgtgtcagc tgaatgattt ctaaaatctc gtaaacttaa tctgacgaaa accttcaagt   1020
acttcgggca acttattttn cccccattca aaagttccat catttctttt caataatctt   1080
tgtaaaattt cttctttctc gaccgctaac aaaaaatgat aaacgtcaat gcctgctcgt   1140
ctcagatatc caatcagctc ttcttcatat tcattttat aaagggtcat tgtaacaata    1200
atcggccgtc cagactcttt ggacattcgt tttaataaat gagcattcca gcaacgccat   1260
tcctgatact cctgaaaatc attttctttc atttcttcgg gaactagctc catcaatgca   1320
ctaccaataa tttctggatc ataaatgatt gcgttgggaa gttttgttg taactcatgt    1380 gcaatggtcg ttttttccgga tccaaacgca ccgtttaacc aaataattat cataatttcc   1440
ttttcttctg aacaaatttc tttgttgttt aatttaggtg ctagattact tttaattttt    1500
ttagccattc acttatagtt actacttaca tctttaacag taaacgagac aaactaaaaa   1560
tacaacatcc tacgctatta acctcgggtt atataacata ctcatctgat aatttctccc   1620
taaaaaaaca gaatgtgggc aatctttta agaataattg aatagaataa caacaaacag   1680
taattcaggt ataaccagct agaaattgtt ttatttttag tcacgagtat gataagcatg   1740
taaatcaaat agaatcatat taggtgaggt tactctgaag aacacaggtt atcgctcgga   1800
aatgtcgaga gacagtaacg agtaaagcag ggattgtcga attaaggctt cctaagata     1860 actagaattt ttttcttacg tctcagaaag ccaaagctca attattgtga ttaccctata   1920
atcttcttct tttattcggc gacctcttta atatgattaa ttggaggttt ttaaattgaa   1980
agctgtcact gcatcatcta agaaaaatac cctacttgct aaaagtatcg ggaatcttac    2040
cttgctcatc attttaggca tttttcatttt tatcatcgtc ttctcttggc taaaaatgaa    2100
tcgccctctc cacacccttc cctcagaaga attcctcgca acaccaagta aaacagatga   2160
tttcttatct ccatcaaatc tttttttactt tcaattcga accatgtttc gaatgattgt    2220
ggggatggct tggtccttcc tgttttcctt tgttttttggt attttagccg taaaatataa    2280
aacggcacga agagtcattt taccattagt taatttcctt gaatctgttc cattgctagg   2340
ttttttgacc tttacaactg cttggttact tggtttattt ccaggaaatg tgatgggcgc   2400
agaagcggtt gctatttttg ccatcttcac aggtcaagct t                        2441
```

<210> SEQ ID NO 10
<211> LENGTH: 3480
<212> TYPE: DNA
<213> ORGANISM: Enterococcus faecalis
<220> FEATURE:
<223> OTHER INFORMATION: Designated as EF-7

<400> SEQUENCE: 10

```
aagcttctag cgtttcggat tggcgcctat gatgcaccag gagagcgacg aatcaatacc       60
aaaaatatgc ctacagcagg aggacttgca atctacattg cttttgctag ttcatgttta     120 ttgattttc gttcgattat cccacaagat tatatttggc cgattatttt ggctggtgga      180
atggttgttt tgacaggcct cattgatgat attaaagaga ttactccaat gaaaaaaaca    240 atcggtatttt tgttagcagc attagttatt ttattttgtt gctggaattc ggatagattt    300
```

```
tgtgacgttg ccagttgttg gaatgattga tttgcgctgg tttagtttac cactaacttt    360
attgtggatt ttagcgatta cgaatgcagt aaatttaatt gatggtttgg atggtttagc    420
atcaggcgta tccattattg gattaaccac gattggtatt acagggtatt ttttcctaca    480
tgctaaaacg gtctatatcc caattgttat ttttatttta gttgcgagca ttgcgggatt    540
tttcccatac aattttatc cggctaaaat atttctagga gataccgggg cgttattcct     600
cgggtttatg attgcagtaa tgtcgttaca gggcttgaaa aatgctacgt ttattacggt    660
aattacgcca atggtgattt taggtgtgca attacggata cggtttatgc aattattcga    720
cggctattga acaagaagcc catttcctca gcagataaaa tgcatttaca tcaccgcttg    780
ttatctttag gttttaccca taaagggcg gtcatgacta tttatgcatt agcgttagtt     840
ttttcctttg tctctttatt gttcagctat tcaagtacag tagcatcaat tttattaatt    900 gtctttgtt taattggctt agaactattc attgaactaa tcggtctagt tggcgaaggg    960
catcaaccgt tgatgtattt gttacggatt ttagggaatc gtgaatatcg tcaggagcaa   1020
atgaaaaagc gacttggcaa gcattctaag agaaagtaaa gaaatcttta ggttgctttg   1080
cgagagctaa acctatgata taattccatt aaacttaaaa aagtatatgt gtgaaacata   1140
tgcttttttt ttaagacgat gtttcagtag taaggagaaa tgagcatgca agaaatggta   1200
acaatctcga ttgtcactta taatagtcgt tacatttta atgtactaga ccaattaaaa    1260
gccgaactag gtactgatag tatctatgat attcatatct atgacaatca ttctgaaaca   1320
gcgtatcttg aaaaattaac aacatatgaa ccatttatta ctatccatcg cgctgaagaa   1380
aatcaagggt ttggtcatgg tcataatcaa gtgttattca atgcttcgac aaagtatgca   1440 attatttta tcccgatgtg ttggttacta aagacgtgct tgatcgttat tagacgtatc    1500
aaatagataa gaacattgca gtcggtagcc ctaaagttgt taaatgaaga tggcacgacg   1560
caatatttag ttcgtcaaaa attagatgtc ttcgattata tgttacgttt tattcccttt   1620
caatttgtaa agaaaatttt tgataaacgt ttgagtattt atgaatgtcg cgatttgtcg   1680
gatacagaaa caacggatat taaaatgggc tcaggctgtt tatgttgat tgatcgtgaa     1740 aaattcgttg aaattggtgg gttcgatgaa cgtttcttca tgtactttga agacaacgat   1800
ttatgtttac gctttggcaa agcaggctat cggattctct atacgccttt tgaaacggtt   1860
gttcacatgt atgaaaaggg cgcccataaa agtcgaaaat tgtttaaaat ctttatgcaa   1920
tcaatgggga aattttttaa caaatggggc tggaggttct tttaatgagt caaagattag   1980
cggtagtcat cgtcttatat caaatgaaaa tggctgatac gccgaattat tgttattaa    2040 aagaagtggt agaccacccc caattgcact tatttattta tgacaacagt ccacttcctc   2100
aagaagatgc attattttta caaccaaatg ttacttatcg acataatcct gataatccag   2160
gactagcgac cgcttataat gaagcgattg cttttagtca agcgaatcaa tgtgaattat   2220
tgttgctcct tgaccaagac acagaagtgc cagcctctta ttttgatacg ttgatcatca   2280
tgccattaga tccgactgtg gcagtctatg ttccaattgt agaagcaaat ggacaacaaa   2340
tttcgccagt atatagtgat caatacgttg ggcttaaagg agcaaagcca acagcaggga   2400
tagccaacca accgttgatg gctatcaatt ctggtacagt tattacggca gaaacgctac   2460
gctggttgga aggattttcg gaagaatttc ctttggacta tttagaccat tggttctttt   2520
atcaattaaa tcaagccaat aaaaagatt aagtcttacc aatccaccta aaacaagaat    2580
tgtctgtttt agattatcgt acaatgagtc ctcaacgtta tcgctctatt attgaagcag   2640
```

```
aaacgttatt ttatcgtcga tatgatcaag aaaagttttc ccatcatcga cgccatttat    2700
ttttacgcag tagtaagcaa ttttttaactg tcaaaaatcg ccaaatttgg cggcaaacat   2760
tggcagaatt tctcaagtta atgaaaggat aatctatgat ctcagtttgt attgcgacat    2820
ataatggaga aaaatatctc gcggaacaat tagatagtat tcttttacaa gtcagtgaag    2880
aagatgaact aattatttca gatgatggtt ctactgatca tacgttggaa attttgagga    2940
cgtatgcagc gaattatccc caaattcaat tgttacaagg tcccagggca aggagtgatt    3000
gctaattttg cattttgcct tacgcatacg aaaggcgaag taatatttt agcagatcaa    3060 gatgatgttt ggttgccaaa taagtaacg acggtgacaa atatttga agcgcaccct      3120 gacatccaag tggttattag tgacttgaaa attgttgatg cggatttaca agttaccaat    3180
ccctcttatt aagtttcga aaagtcaaac cagggttttg cgaaatgcg ataaaaagtg    3240 gctatattgg ggcaggtatg gcctttcgtc aagaaatgaa aaacgtcatt ttacccattc   3300
cgccagaagt tcctatgcat gatatgtgga ttggcttatt agctgcacgg aagaagcaaa   3360
cgggtctcat taaagaacca ttagtgcttt accgaagaca tggagcgaat gtcagcccca   3420
ttattaccaa aacaagtttc caacaaaaat taaattggcg tgtgaattta ttaaaagctt   3480
```

<210> SEQ ID NO 11
<211> LENGTH: 3615
<212> TYPE: DNA
<213> ORGANISM: Escherichia coli
<220> FEATURE:
<223> OTHER INFORMATION: Designated as EC-24

<400> SEQUENCE: 11

```
aagcttttct tgcgtgttct tgtgaggctt ccttcgccat tatcatcacg atccacataa     60
ataaagccgt agcgcttaga catttgtgaa tgagatgcac tgactaaatc aattggcccc    120
caactggtgt accccataat atccacacca tcggcaatcg cttcatttac ctgtaccagg    180
tgatcgttta aataggcaat tcgataatcg tcctgtatcg aaccatccgc ttcaacgctg    240
tcttttgcgc ctaatccgtt ctcgacaata aataacggtt tttgataacg atcccaaagc    300
gtatttaaca gaacccgtaa tccaaccgga tcaatttgcc accccactc tgaactttc     360 agatgcggat tggggatcat attcagtatg ttgccctgcg cattttatt aatgctttcg     420 tcgtgggaac acaaccagtc atgtataact aaagagatga atcgacggta tgttttaaat    480
ctctgcgtca ctttcagtca tctcaatggt gatattgtgg tcgcggaaga aacgctgcat    540
atagccggga tactggccac gcgcctgaac atcaccaaag aacatccagc gccggttctc    600
ttccatggcc tgcaacatat cctgtggctg gcaggtgagg gggtaaacca gcccaccgag    660
aagcatattg ccgattttcg cttcggggag caggctatga caggctttaa ctgcccgcgc    720
actggcaacc agttgatggt ggatagcctg ataaacttcc gcctcgccac tctcttctgc    780
cagccccacg cccgtgaatg gcgcgtgtaa cgacatgttg atttcattaa acgtcagcca    840
taacgccact ttatgttggt agcgagtaaa gaccgtgcgg gcgtaatgtt cgaagtgatc    900
gatgaccgct cgattagcca accgccgtag ttttcacca gcccatatgg catttcgtaa   960
tgggataacg ttaccagcgg cttgatcccc gcctgcgcca tttcatcaaa cagccgatcg   1020
taaaacgcta accccgcttc attcggttcg acttcgtcgc cctgagggaa aattcgcgcc   1080
caggcaatgg aaatacgcag acaggtgaag cccatctcgg caaataacgc gatatcttcc   1140
gggtaacggt gataaaaatc gatggcgaca tctttgtatt tctctttccc caggatgcgc   1200
ggttccattt ttcccattac gcatgaggct gtaaatctga ggtcgagatc cctttgccat    1260
```

```
cttcctgcca ggcaccttcc acctgattgg cagctgttgc ggcaccccaa agaaatgttt    1320
ctggaaatgc tttcataatt aactcctttt atcgttagcg aatgatggat aacagcggtt    1380
cacctgcgct tatctgcgcc gtgccgtggg gtaatacgtc cgtaaaatca tcgctattac    1440
tgattaatac cggcgtcgtc agatcaaatc cggcctcgcg aatagcaggg atatcaaaag    1500
aaatcagccg atcgcctgta ttgaccttgt cacccacgtt gacgtgagcg gaaaagaatt    1560
tgccgtccag ttttacggtg tcgataccga catgaatcag gatctccaca ccatcatctg    1620
actcaatgcc aatggcgtgt aatgtggcga caacgaagc aattcgaccc gcaaccggag     1680
aacgcacttc accaaccgag ggcagaatgg caataccttt acccaacagg ccactggcaa    1740
acgtggtatc agcgacgtga atgagcgaca caatctctcc cgtcatcggt gaacagatac    1800
cgccctgctc aggtggtgta ataacctctg gtgttttctc ttcggggcac cctgcgctgg    1860
ctgacgttta gcggtgatga aatgaagcat caccgtaccg acaaatgcgc aaccgatggc    1920
aatgacaccg ccaataacgc tggcccagac ggtgaaatca attcccgttg acgggatggt    1980
ttgcatgaag gtgaaaatac ttggcaaacc aaaggagtag actttcgttt gcgcgtagcc    2040
aataatggtg gcccccaaag ccccactgat acaggcgata acaaagggt acttacgcgg     2100 caggttgacg ccatataccg ctggttcggt gataccaaac agactcgtca acgccgctga    2160
tcccgccacc actttttct gcgcatcgcg ttcgcagagg aagacgccga gcgccgcccc     2220
gacctgcgcc ataatggcgg gcattaacag cgggatcatg gtgtcgtagc ccagcacggt    2280
gaagttattg atacacaccg gcaccaggcc ccagtgcagt ccgaacatga cgaagatttg    2340
ccagaagccg cccattaccg cgcccgcaaa tgcaggaacc gcctgataaa gccagagata    2400
accggcggca atcagttcgc ttatccaggt tgatagcggc cccaccagca gaaaggtgac    2460
gggtgtgata accatcagac atagcaatgg tgtgaagaaa tttttgattg ccgacggtaa    2520
ccacgcatta agtcggcgtt ccagaatgct gcacaaccag gcagaaaaa taatgggaat     2580 aaccgatgac gagtaattca acaatgtgac cggaatacc aggaaatcca gccccagcgc     2640
atccgctttt gcgcgttctc gaaaagcagt acagaattaa tggatgcact aacgctccac    2700
caatcaccat ggcagtaaat ggattatcgc cgaagcgttt ccccgcggtg tatcccagga    2760
ttatcgggaa gaaccaaaac aaggcatcac tggcgctgaa taaaattaaa taagtaccac    2820
tttgttcggg cgtccactga aaagtgagcg ccagagccag catacctttc aagatccccg    2880
gttgcccgcc atcaaccga tacagaggcg taaaaatacc tgaaataaca taacaaagc      2940 ggtttagaca gattaccttt atcatacatt ttccggtgcc tgttgcgctt tttcgtcaag    3000
gcctgccaca ctgttaaccg ccaggaagac atcggccaca tggttaccta tgaccacctg    3060
aaactggcca ccgctttcca ccaccataat aataccgggg gtcttttca gtacctctgc     3120 ttgcgctttg ctttcatcct ttaatttaaa aacgtaaatc gcgttgcgca atgcatcaga    3180
ctcacaatgt tatctgcgcc cccgactcct gcgactattt ttctggctaa ctccgtcata    3240
acttgccctc tacgctttgc ggcaaaactc caaaaaaaaa cctgaaaaaa acggcctgac    3300
gtgaatcaag caattttttt caggttttgc ccgcttagtg cggtaacaat cctttactca    3360
gtaataatat ttcagtgttc tttgcgcacg cgctctatat ttatggctaa aaacataatc    3420
tctgcgggtg aaattttacg ttgatactgc aaaccaataa aaatggcgat ccgttccgca    3480
cattgccatg cttgcgggta attttgtttt actgcttgtt gtaatgattc atcactatcg    3540
ttaattgaag catgttcaag aatacgccag gataaaaact tcagatgtgt aaccagtcgc    3600
```

-continued tgataactca agctt 3615

<210> SEQ ID NO 12
<211> LENGTH: 4954
<212> TYPE: DNA
<213> ORGANISM: Escherichia coli
<220> FEATURE:
<223> OTHER INFORMATION: Designated as EC-34

<400> SEQUENCE: 12

```
aagcttaacc gctctcatct gttgaccgca cggcatagct atattctgcc ggtcctggga      60
cgtagcgaga ttgacatgca aaaaacggt gcgcaggcgg taaccgttga ggattcaatg     120
tcgatgattc atgcctcgcg tggcgtgtta aaacccgccg gtgtaatgct gaaatcagag    180
tgtgcagtgg tcgcgggaat cgcgcaggca gcactacccc agagcgtggt agcctgggag    240
tatctggtgg aagattatga tcgcattcgc aatgacattg aagctgtgct gccagagttc    300
gccgactata accagcgcat ccgtcatccc ggtggttttc acctgataaa tgcagctgct    360
gaaaggcgct ggatgacgcc gtcaggtaag gctaatttca ttaccagcaa agggctgtta    420
gaagatccct cttcagcgtt taacagtaag ctggtcatgg cgacagtacg cagccacgat    480
cagtacaaca cgacgattta tggtatggat gatcgctatc gaggggtatt cggtcaacga    540
gatgtggtct ttatgagtgc taaacaagct aaaatttgcc gtgtaaaaaa cggcgaaaga    600
gttaatctta ttgcgcttac gccagacggt aagcgcagtc acgccgcatg gatagattaa    660
aagtggtcat ttaccctatg gctgaccgct cactggtgac ctattttcca gaatcgaatc    720
acatgctaac acttgataac cacgatccat taagtggcat tcctggctat aaaagtattc    780
cgcttgaatt agaaccatca aattaatgtc tcttctcatt tcttctgctg tcatccgcac    840
agcagaagaa ttcctcattg actattattt cgcaatttgc tcacatggat taaattaaac    900
tacatactat aagatataaa cttctgccta cagctgtaag aaactccgct cagtactgaa    960
gcaccagtcc tatttcctct tttctccagc ctgttatatt aagcatactg attaacgatt   1020
tttaacgtta tccgctaaat aaacatattt gaaatgcatg cgaccacagt gaaaaacaaa   1080
atcacgcaaa gagacaacta taagaaatc atgtctgcaa ttgtgggtgt cttattactg   1140
acacttacgt gatagccatt ttttcggcaa ttgatcagct gagtatttca gaaatgggtc   1200
gcattgcaag agatcttaca catttcatta tcaatagttt gcaaggctgt aaacaaacag   1260
caaattataa atatgaaatg ttaaaaaagt atcgataaaa actttattgt tttaaggaga   1320
taaaatgtcg ctcgtttgtt ctgttatatt tattcatcat gccttcaacg ctaacatttt   1380
agataaagat tacgccttct ctgacggcga gatcctgatg gtagataacg ctgttcgtac   1440
gcattttgaa cctatgagc ggcattttaa agagatcgga tttactgaaa ataccattaa   1500
aaaatatcta caatgcacta acatccagac agtgacggtg cctgttcctg cgaagttttt   1560
acgtgcttca aatgtaccga ctggattgct taatgaaatg attgcttatc tcaactcgga   1620
agaacgcaat catcataatt tttcagaact tttgcttttt tcttgcctgt ctattttgc    1680
cgcatgcaaa ggtttcatta cactattaac taacggtgtg ctatccgttt ctgggaaagt   1740
gagaaatatt gtcaacatga gccggcgca cccatggaag ctgaaagata tttgtgactg   1800
cctgtacatc agtgaaagcc tgttgaagaa aaacttaagc aagagcaaac gacattctca   1860
cagattcttt tagatgcaag aatgcagcac gcaaaaaatt tgatacgcgt agaaggttca   1920
gtcaataaaa ttgccgaaca atgtggttat gccagtacat cttatttat ttatgcgttc    1980
cgcaaacatt tcggcaacag tccgaagaga gtttctaagg agtaccgttg tcaaagtcac   2040
```

```
acgggtatga atacgggcaa cacgatgaat gctttagcta tttgattatt tgctaacgag    2100
tagtcaacca cacacgctgc gtaagaatta aatggggcag ccattccctg ccccgcgttg    2160
tttttaggcg atatatttat tgaaataaat aagtgacatc catcacatat ttatgcactt    2220
gcataacctg ttgcatgatt atttatgatc tcaattctgc attttgtcag taaaatgcaa    2280
taatttatta aatatcaata aattagttgt ttatcggcga gaaattactt aatagaacag    2340
aaagtaatgt caacgcttta tggactgttt tttcccttt tttagctaaa tctgctatct    2400
ctttatgtga ctaacttcac ttacatccac ttatttctct tcgtaaaatt actttggaat    2460
taagtacaat aagaagagga acatttatga agtctgcatt aaagaaaagt gtcgtaagta    2520
cctcgatatc tttgatactg gcatctggta tggctgcatt tgctgctcat gcggcagatg    2580
atgtaaagct gaaagcaacc aaaacaaacg ttgctttctc agactttacg ccgacagaat    2640
acagtaccaa aggaaagcca aatattatcg tactgaccat ggatgatctt ggttatggac    2700
aacttccttt tgataaggga tcttttgacc caaaaacaat ggaaaatcgt gaagttgtcg    2760
atacctacaa aatagggata gataaagcca ttgaagctgc acaaaaatca acgccgacgc    2820
tcctttcatt aatggatgaa ggcgtacgtt ttactaacgg ctatgtggca cacggtgttt    2880
ccggcccctc ccgcgccgca ataatgaccg gtcgagctcc cgcccgcttt ggtgtctatt    2940
ccaataccga tgctcaggat ggtattccgc taacagaaac tttcttgcct gaattattcc    3000
agaatcatgg ttattacact gcagcagtag gtaaatggca cttgtcaaaa atcagtaatg    3060
tgccggtacc ggaagataaa caaacgcgtg actatcatga caccttcacc acattttctg    3120
cggaagaatg gcaaccctca aaccgtggct tgattactt tatgggattc cacgctgcag    3180
gaacggcata ttacaactcc ccttcactgt tcaaaaatcg tgaacgtgtc cccgcaaaag    3240
gttatatcag cgatcagtta accgatgagg caattggcgt tgttgatcgt gccaaaacac    3300
ttgaccagcc ttttatgctt tacctggctt ataatgctcc gcacctgcca aatgataatc    3360
ctgcaccgga tcaatatcag aagcaattta ataccggtag tcaaacagca gataactact    3420
acgcttccgt ttattctgtt gatcagggtg taaaacgcat tctcgaacaa ctgaagaaaa    3480
acggacagta tgacaataca attattctct ttacctccga taatggtgcg ttatcgatg    3540 gtcctctgcc gctgaacggg gcgcaaaaag gctataagag tcagacctat cctggcggta    3600
ctcacacccc aatgtttatg tggtggagaa ggaaaacttc aacccggtaa ttatgacaag    3660
ctgatttccg caatggattt ctacccgaca gctcttgatg cagccgatat cagcattcca    3720
aaagacctta agctggatgg cgtttccttg ctgccctggt tgcaagataa gaaacaaggc    3780
gagccacata aaaatctgac ctggataacc tcttattctc actggtttga cgaggaaaat    3840
attccattct gggataatta ccacaaattt gttcgccata cagtcagacg attacccgca    3900
taaccccaac actgaggact taagccaatt ctccttatacg gtgagaaata acgattattc    3960
gcttgtctat acagtagaaa acaatcagtt aggtctctac aaactgacgg atctacagca    4020
aaaagataac cttgccgccg ccaatccgca ggtcgttata gagatgcaag gcgtggtaag    4080
agagtttatc gacagcagcc agccaccgct tagcgaggta aatcaggaga gtttaacaa    4140 tatcaagaaa gcactaagcg aagcgaaata actaaacctt catgcggcgg atttttccgc    4200
cgccttattg agcgagatag cgatgcacgt tacagccaag ccctccagtt ttcaatgtaa    4260
tctcaaatgt gattactgtt tttaccttga aaaagagtcg cagtttactc atgaaaaatg    4320
gatggatgac agcactttga aagagttcat caaacaatat atcgcagcgt ctggcaatca    4380
```

```
ggtctatttt acctggcaag gcggtgaacc cactctggct ggcctggatt ttttccgtaa    4440
agttattcac tatcaacaac gctatgcagg ccaaaaacgt attttttaatg cattacaaac   4500 gaatggcatt ttattgaata atgaatggtg tgccttctca aagaacatga atttctggtg    4560
gtatctcgat cgatggcccc caggagttac atgaccgtta cagacgcagt aattcaggta    4620
acggtacttt tgcaaaagtg atagcagcca tcgagcgtct gaaatcatat caagtagagt    4680
ttaatacgtt aaccgtcatt aataacgtta atgtccatta ccctcttgag gtttatcatt    4740
ttttaaaatc tatcggcagt aaacatatgc aatttatcga attgctagaa accgggacgc    4800
cgaatattga tttcagtggt catagtgaga acacattccg tatcattgat tttctgtgc     4860 ctcccacggc ttatggcaag tttatgtcaa ccattttttat gcaatgggtt aaaaacgatg   4920
tgggtgaaat tttcatccgt cagtttgaaa gctt                                4954

<210> SEQ ID NO 13
<211> LENGTH: 3796
<212> TYPE: DNA
<213> ORGANISM: Escherichia coli
<220> FEATURE:
<223> OTHER INFORMATION: Designated as EC-39

<400> SEQUENCE: 13
aagcttaatc gcgtgaatca ggagtaaaaa aatgacaacc cagactgtct ctggtcgccg       60
ttatttcacg aaagcgtggc tgatggagca gaaatcgctt atcgctctgc tggtgctgat     120
cgcgattgtc tcgacgttaa gcccgaactt tttcaccatc aataacttat tcaatattct     180
ccagcaaacc tcagtgaacg ccattatggc ggtcgggatg acgctggtga tcctgacgtc     240
gggcatcgac ttatcggtag gttctctgtt ggcgctgacc ggcgcagttg ctgcatctat     300
cgtcggcatt gaagtcaatg cgctggtggc tgtcgctgct gctctcgcgt taggtgcgca     360
attggtgcgg taaccggggt gattgtagcg aaaggtcgcg tccaggcgtt tatcgctacg     420
ctggttatga tgctttttact gcgcggcgtg accatggttt ataccaacgg tagcccagtg     480
aataccggct ttactgagaa cgccgatctg tttggctggt ttggtattgg tcgtccgctg     540
ggcgtaccga cgccagtctg gatcatgggg attgtcttcc tcgcggcctg gtacatgctg     600
catcacacgc gtctgggggcg ttacatctac gcgctgggcg acaacgaagc gacaacgcgt     660
ctttctggta tcaacgtcaa taaaatcaaa atcatcgtct attctctttg tggtctgctg     720
gcatcgctgg cgggatcata gaagtggcgc gtctctcctc cgcacaacca cggcggggac     780
tggctatgag ctgatgctta ttgctgcggt ggttctgggc ggtacgagtc tggcgggcgg     840
aaaaggtcgc attgttggga cgttgatcgg cgcattaatt cttggcttcc ttaataatgg     900
attgaatttg ttaggtgttt cctcctatta ccagatgatc gtcaaagcgg tggtgatttt     960
gctggcggtg ctggtagaca acaaaaagca gtaataacga ctacaggcac atcttgaata    1020
tgaacatgaa aaaactggct accctggttt ccgctgttgc gctaagcgcc accgtcagtg    1080
cgaatgcgat ggcaaaagac accatcgcgc tggtggtctc cacgcttaac aacccgttct    1140
ttgtatcgct gaaagatggc gcgcagaaag aggcggataa acttggctat aacctggtgc    1200
tggactccca gaacaacccg gcgaaagagc tggcgaacgt gcaggactta accgttcgcg    1260
gcacaaaaat tctgctgatt aacccgaccg actccgacgc agtgggtaat gctgtgaaga    1320
tggctaacca ggcgaacatc ccggttatca ctcttgaccg ccaggcaacg aaaggtgaag    1380
tggtgagcca cattgcttct gataacgtac tgggcggcaa aatcgctggt gattacatcg    1440
cgaagaaagc gggtgaaggt gccaaagtta tcgagctgca aggcattgct ggtacatccg    1500
```

-continued

```
cagcccgtga acgtggcgaa ggcttccagc aggccgttgc tgctcacaag tttaatgttc    1560
ttgccagcca gccagcagat tttgatcgca ttaaaggttt gaacgtaatg cagaacctgt    1620
tgaccgctca tccggatgtt caggctgtat tcgcgcagaa tgatgaaatg gcgctgggcg    1680
cgctgcgcgc actgcaaact gccggtaaat cggatgtgat ggtcgtcgga tttgacggta    1740
caccggatgg cgaaaaagcg gtgaatgatg gcaaactagc agcgactatc gctcagctac    1800
ccgatcagat tggcgcgaaa ggcgtcgaaa ccgcagataa agtgctgaaa ggcgagaaag    1860
ttcaggctaa gtatccggtt gatctgaaac tggttgttaa gcagtagttt taatcaggtt    1920
gtatgacctg atggtgacat aaatacgtca tcgacagatg aacgtgtaat ataaagaaaa    1980
gcagggcacg cgccaccta acacggtggc gcattttatg gacatcccga atatgcaaaa    2040
cgcaggcagc ctcgttgttc ttggcagcat taatgctgac cacattctta atcttcaatc    2100
ttttcctact ccaggcgaaa cgtaaccggt aaccactatc aggttgcatt tggcggcaaa    2160
ggcgcgaatc aggctgtggc tgctgggcgt agcggtgcga atatcgcgtt tattgcctgt    2220
acgggtgatg acagcattgg tgagagcgtt cgccagcagc tcgccactga taacattgat    2280
attactccgg tcagcgtgat caaaggcgaa tcaacaggtg tggcgctgat ttttgttaat    2340
ggcgaaggtg agaatgtcat cggtattcat gccggcgcta atgctgccct ttccccggcg    2400
ctggtggaag cgcaacgtga gcgtattgcc aacgcgtcag cattattaat gcagctggaa    2460
tcaccactcg aaagtgtgat ggcagcggcg aaaatcgccc atcaaaataa aaactatcgt    2520
tcgcttaacc cgctccggct cgcgaacttc ctgacgaact ctgcgctgtg acattatta    2580 cgccaaacga aacggaagca gaaaagctca ccggtattcg tgttgaaaat gatgaagatg    2640
cagcgaaggc ggcgcaggta cttcatgaaa aaggtatccg tactgtactg attactttag    2700
gaagtcgtgg tgtatgggct agcgtgaatg gtgaaggtca gcgcgttcct ggattccggg    2760
tgcaggctgt cgataccatt gctgccggag ataccttta cggtgcgtta atcacggcat    2820
tgctggaaga aaaaccattg ccagaggcga ttcgttttgc ccatgctgcc gctgcgattg    2880
ccgtaacacg taaggcgca caaccttccg taccgtggcg tgaagagatc gacgcatttt    2940
tagacaggca gaggtgacgc ttggctacaa tgaaagatgt tgcccgcctg gcgggcgttt    3000
ctacctcaac agtttctcac gttatcaata aagatcgctt cgtcagtgaa gcgattaccg    3060
caaagtgagc gcgattaaag actcaattac gcgccatcag ctctggcgcg tagcctcaaa    3120
ctcaatcaaa cacataccat ggcatgttg atcactgcca gtaccaatcc tttctattca    3180
gaactggtgc gtgtcgttga acgcagctgc ttcgaacgcg ttatagtct cgtcctttgc    3240 aataccgaag gcgatgaaca gcggatgaat cgcaatctgg aaacgctgat gcaaaaacgc    3300
gttgatggct tgctgttact gtgcaccgaa acgcatcaac cttcgcgtga aatcatgcaa    3360
cgttatccga cagtgcctac tgtgatgatg actgggctc cgttcgatgg cgacagcgat    3420
cttattcagg ataactcgtt gctgggcgga gacttagcaa cgcaatatct gatcgataaa    3480 ggtcatacc gtatcgcctg tattaccggc ccgctggata aaactccggc gcgctgcggt    3540
tggaaggtta tcgggcggcg atgaaacgtg cgggtctcaa cattcctgat ggctatgaag    3600
tcactggtga ttttgaattt aacggcgggt tgacgctat cgccaactg ctatcacatc    3660 cgctgcgtcc tcaggccgtc tttaccggaa atgacgctat ggctgttggc gtttaccagg    3720
cgttatatca ggcagagtta caggttccgc aggatatcgc ggtgattggc tatgacgata    3780
tcgaactggc aagctt                                                    3796
```

<210> SEQ ID NO 14
<211> LENGTH: 6914
<212> TYPE: DNA
<213> ORGANISM: Enterobacter cloacae
<220> FEATURE:
<223> OTHER INFORMATION: Designated as ET-49

<400> SEQUENCE: 14

| | | | | | |
|---|---|---|---|---|---|
| aagcttttcg | agttcgccat | ccggcaacag | ctcactgagc | ttttacgcgc | ccagggtgcc | 60 |
| tttgaactca | attcccagct | cagtaaggcg | gtcctgaata | atctctttgc | gagattttc | 120 |
| actggtaccg | gcatcaggtg | ttgcaggttt | cagctcgcca | ccagcctcgc | ccttcatcag | 180 |
| ccggacgtta | gacttcagcg | ccgggtgaag | atctttcaac | tccaccacgt | cgccaacctt | 240 |
| tacgccgaac | catgggcgca | caacttcgta | tttagccatg | ctgtttcctt | acgccaggtt | 300 |
| agcgccgtag | acaacgccag | acaggcctga | tcgtctgcag | taatttgcag | gccttcagca | 360 |
| gacatgatct | ggaagttgta | gttaacgtta | ggcagtgggc | gcggcagtgg | cacaacgcca | 420 |
| acagccatac | ccaccagtgg | ggagatcacg | tcacgacgac | gaacgtacgc | gataaactcg | 480 |
| ttaccggtca | gcgcgaagtc | atgcggattt | ctttcaccgg | tgcgaatggc | agaacagcct | 540 |
| gcaggagagt | gccgctcacc | acaccattaa | ctacgtatgg | ctgagccata | tttgcccaga | 600 |
| tctcagggga | aacccacatc | acatcatact | gagctacttt | gttggtgcgt | gcggtggtac | 660 |
| cgaatgctcc | tttaccaaag | aactcaaaat | attgagtcgt | ggttgcgctg | gtcaggtcga | 720 |
| tgttcgcacc | accagcacca | gaaccgaggt | taatcttctt | ggtgttgcgg | tggttcttga | 780 |
| tgccctgcgc | cgggtaggac | tgaacctgaa | ttttgaatc | gccgttcagg | tagtagttga | 840 |
| cgcgcttctg | gttgaacttg | cgcatcttcg | ccatctgcga | atccagaacc | agatcaatgc | 900 |
| ctacagagtt | aaggccagca | gcatgacgcc | agttaacacc | gtagccagca | gtgaacaccg | 960 |
| gaatcgggtc | gccatcgctc | gcgtagtcag | tgtggtcgaa | ggagaatggc | gcctgaccat | 1020 |
| cgatgcttac | tgacacgtcg | tcagcgatgt | cgccgaccac | gttatacagc | ttggcggttt | 1080 |
| taccaaccgg | cagcacggtc | tgaacgccga | tcaggtcgtt | tacgattcc | atgccaactt | 1140 |
| cctgatcccg | cagctgcagc | acctggttgt | caatctcagc | ccagaagtca | cgggagaaac | 1200 |
| cgccaacagc | gttacaagcc | agcatgtcag | gcgtcatcat | tgcgcggtta | gctgcaatga | 1260 |
| tggaatcgtt | ctgtaggttc | cacatgttgc | ggtttgccca | cagctcactc | cagtgcccgc | 1320 |
| cgaggcggga | gttagtcgcc | agcgtctctt | tagagaagta | catatgtgtt | tgtccttttg | 1380 |
| ttacgcgcca | gctgcggcga | cagtgccaac | gcgcatacgc | acgcgaatga | agtcagtggt | 1440 |
| gctggccgcg | atggtgtatt | catcctggct | gtagccgatc | actgaatcag | tgtcggatgt | 1500 |
| ggcaagggta | aactgaccgg | cagttcccag | cttgatcggg | ctgtctttt | tatacgcacc | 1560 |
| aggcaggcag | cgcagcgcca | gctcacgacc | ttcttcgacg | tagttaccta | ctgccgaatc | 1620 |
| cccggcaggg | atttcttcgg | tgattgtcag | gccctggtga | taaccgacat | cgatgatgta | 1680 |
| caggcggccg | gttagcgcgg | tggcctgagc | gaatttatcg | gatgagttga | tggttgcggc | 1740 |
| ggtgccagga | agcaacccgg | cggccgttgt | gcgggtttcg | gtcttgtaca | gagactgacc | 1800 |
| gtcgatatta | acgcgacgat | aacgtggcat | tattccggct | ccttacttga | agtgttcgtc | 1860 |
| tgcggctggt | gcgccggttt | ctttgtgctg | ctgagcattg | ttggtgccca | gcgacttgaa | 1920 |
| catcgcgtcc | agagcttcgc | ctgacagagc | gttcgcgagc | gatatcgcca | tggaccttcg | 1980 |
| caaccgcttc | gcgcttttgct | ttctcttcgg | cacgggagtt | cgcggtaagg | gtttccgcga | 2040 |
| gttgcttctg | attggcctgc | agcgcatcaa | ccttttccgc | gagaggctta | atagccgctt | 2100 |

```
cagtattggt cgcaacagcc tggccgatca tgctgccgat ttgttccagt tcttctttgg   2160
ttaaaggcat gtcgcctccg ttttgtggtt tggtgcaggc tgttcctgcg gtgtgaatag   2220
agctttgaat tgttagcgac gactgccacc cacgactcct ggcgcgctac tgcggttccg   2280
gtatcgtcga ttgtgatctt cccgccatca gcgaataccg taaacctgag catcaccgcc   2340
atttcgcacg atgaccacct gcgagtcagt gagtcagcaa cccaggcata ttcatccgtg   2400
cccggcgcaa acttggcttt ggctgcccga tcgagacgct gctcgcgctc ccggtaggat   2460
tcacccacca gcgcgccgga gttcgcttta agcggctgcg ccagatcggc gtttaccatc   2520
aggccaacgc cctgctcagg ggtggcggct ccgacttcgt gcagtaggat cgcgtcgtgg   2580
tccatgctgt gaatcttcgc cacccactcg gcacccgtag ctctctgttg ttcgttaggc   2640
tcaagctggt cgaggaaagc ggcgacactg gtatgaatcg gcggaacgtc atcgccgcgc   2700
tcgatggctg cgacgcgctc aagtagttct cggccacctt cagactcacc ggcgcgggca   2760
acatcaaccc acttttcgag gtagatacga ttaccggact tcttaacgtt gcggttccac   2820
gcgccgatat ggcctgcgtt aatcccctcc ggggagaaag cagacacgaa ctgaccatta   2880
acctgagggt ggcccagcgg cgccagggta ccttccagcc ccttatagtg ggcgtcgatt   2940
tgctcttgcg tgtacaagcc gccattcatg acgacgttag ctggaagtgt gtagctcggc   3000
agcaccaggt gctcacgccc gttgtatgtt tcgcgccgga tagactggct gttcacctttt   3060 gtggtgatgt tgacctgaat atgctcacca tgtttcggtg cctggattgg acgtgtgct   3120 tcgtggttta cctggaattt catgagttat ttctccgccc aggcgtaacc gctcgcctgc   3180
atcgatttat attcctgttt gagtttcgtg atggtgtccg ggtattccgg cttgccgtcc   3240
gcatccacca gcaccgactg ctggctgcat ttgcagttga tggagttgcc atctttgctg   3300
taccagtcac gcacctcttc gttggtgtag aggtgggcat gggcgcactg cgtgggtatg   3360
tcgcgttgtc ggcgacagag ctgagatgtg aaccagcagc gttttaaggc cgaacaggtc   3420
attcgcctct tggtcttcat cccacttggc ccggcgcagc gcggtagtca cttcagtgcg   3480
tgctatccgg ttagcccggc gtttctcgat gccggtctgg tctgtcaggt tgcgggcaat   3540
gtccagagga ttgagcccgc gcccaacacc atcagtaaga cacgcgccat gtcgcgctta   3600
acgtcagccg tcagcccctt catttcctca aatacgcgcg catgcaccag cgccatgcgt   3660
ttctgatact ggtcgcttgc gaggatggag gccagcgact cacgcccggc tgcgtacacc   3720
ggggattgct gactgaggtt gtagaacgac tgcccggtcc ctttttccga agccagatcg   3780
atgtactcgt aaaaccacag gtcgtaatcg ccaccttcaa gcagtacctg atcaaccagg   3840
taactggcat cgttcaggat gatggagagt agcattgggt ttagctggta ttcgtatctg   3900
gcgtttactg cgagggagga aggtatttg ttgagtgctg atttgtacgc cttgccaatc   3960
ttattcatcc gcctggcgaa gtctttcatt gcccggcgtt ccagcgcatc ggctccggtc   4020
ggatcctgat agttacgcgg cagaatcggt ggcttcgtct tcttcgtcgc catcctcttc   4080
tcctaatgga aattcatcga cgttttcata accggcagca gtgcggaatt tcttcacgac   4140
taaaggctgg tttttctccg ctcccctgga acgtctggtt aatctctgcc atggttttgg   4200
catttgcgag tttctcagtt ccagtctgtt cgttgaggtc atcccagata accgtcttct   4260
cgctgactgc atcaataatt ttcaggtcga tgagcttgtc actgaagtct tcaatttcga   4320
atgacaggtc accgcgccgt gactggcagc gcgcgttgaa atatttctga tcctcggtgc   4380
ttgccctttc acccgtctgc atcccaacca gaaccttcac agggatatca acagatgcag   4440
```

```
cgaaggtttg caggttgacg ttataggtcg ctgacggatc cgctacagct gtgaccagtg   4500
gtgtgactgt agcccettgg gttgtcatca gaacatcgtt accacggttc atttccccgg   4560
caacttcgtt aaacttatcc tgcaactcgt ccatgtcacg ccataaagtg acgcgagatt   4620
gttgaaatcg atttccttct caaagttgac attaagctgc cgcgcggcgt tctttaggaa   4680
tgactcacca gaaccaccct cgaccttctc aaggctgacg caggcgttat agccaggctc   4740
aaggaagcca atagcatcat tagaatagtc accaaggata aagacgcgat cgggatgtac   4800
gaagcgctga ttagttccac cgcttggaag gctctcaaca tatttccact gctttggctg   4860
cccgtagcct gccgatttct ggtcagttac ccactcgctg actgttaatg acccagccca   4920
tgcgatcgta accttttta gtgacttgcc acgaacaaca ggctgatccc atgttctgga   4980
atcattgata tgcagcagga tacccgcata acgtccgacc tgtcggcggc ggtctgcttc   5040
agcaaaagcc cgccaaaggc gctttgtgaa aaccttttg tgttcttct cccaggcagt     5100 ttcatcctta ctctcgtcgg catcatcacc ctcgatgatt tccgggttgg tctgccagca   5160
cttgcccacc agcttctcta ctgcgccgtg ggctattcca ccgcgacgat acagtgcgta   5220
gaggttttcg taagtgacct gctcagggaa tccatactcg caccatgcgg aatggcgctt   5280
attgtccagc cccattgtag gcgccaacag ccccatacgg gcacgggcca tccgcgcatc   5340
gttcaacgca tggttgacgg cgagagttaa tttgtcagtc atggtttgtc cgttggtgga   5400
tttaaggcat aaaaaaggc cgctttggcg accttgtggc tatttaaaaa gctaaactct    5460
gttgaacgaa ataaacataa tctgctcagg cttaacgcca taatcacttg ccaacttctg   5520
agtgcactca attaagacag ttgatgcaga tttcgaagag cttgcaccat aaatttcgaa   5580
gttttcaaat actccgccgt tggtgtggta aatcttatat gacataaacc aatcattcat   5640
aatatctact cccttacaga attgagtaga tattatcggc aagtgcatat gtttctttaa   5700
attatctcaa ccttttcggg atcatcatcc cggccatctg gcccttacgt ttaatgtgtc   5760
cgtcgaggct gtagcgaata ccgtcccagc agtgttcgta accgtctgcc agtttaggca   5820
atacctcgcc ggtgatgcgg tccgttttgt aggaccacat gcgggcctct ctcgccacat   5880
tcttgcagcg aggatggata atgatttcgt caaagccgcg aagatgcgcg ataccgtcct   5940
caacactccc ctgccatttc tcggcagccg agatgttgaa gccctggcgc ttgagatagc   6000
tgatagtctc gggtcgggcg gagtcggcct tgatgggcca gtcacgcgat ccggggattg   6060
tgtcgtatag ctctggcata tggtcgagct ctgtctgctg accgtatgcc tcgtattcga   6120
tgtacagccg gttgtgcagg atgaacgagc gcaccagcgt gttagggtct ttggcgaaac   6180
cgaagtcagc accgaagaaa aggcgatcgg cctctttcca tagctggtcc gagaactcag   6240
cgatccggta tttaccggcc agcacctgct tatcagagtt ttcgaggtaa gcaccttccc   6300
aaacccacgc gtatgttgcc gggtcaaggc ggcgctgatc gttctgtcgc tcaccttcca   6360
gcacgtcggg gaaccatgga ttatccgtgt agttcatctc aacgtgatac agtcgtcgcc   6420
agcctcttta cggaaacgct tatccgtgcg ctgccgtcgc gctccgggtt ccatgtcacc   6480
caaatctctg aaccttcctc acgaacggtc gggctcagct tctgccaggc tatttcgctg   6540
actgattcag cctcatcaac ccaacagagc aagatgcgcg ctttcgactt gatgctgtcg   6600
aggttatgcc gcagaccgca gaacacgtag ttaacgctct tgtcgatggt gcggatgtac   6660
ttctcgccga tatcaaagtt ggaagccagc cagggaacag acaggatagc ctgtttcacc   6720
tcctgcatac tcgactcttc cagtgagttc atgaattcac gcgcacagag caccacgccg   6780 cttcaccgt tcatcatcga ctgatacgcc tttacggctg tcatcagcgc aaaagtgcgc    6840
```

<210> SEQ ID NO 15
<211> LENGTH: 5975
<212> TYPE: DNA
<213> ORGANISM: Klebsiella pneumoniae
<220> FEATURE:
<223> OTHER INFORMATION: Designated as KI-50
<220> FEATURE:
<221> NAME/KEY: misc_feature
<222> LOCATION: (456)..(456)
<223> OTHER INFORMATION: n = a or t or c or g
<220> FEATURE:
<221> NAME/KEY: misc_feature
<222> LOCATION: (3074)..(3074)
<223> OTHER INFORMATION: n = a or t or c or g
<220> FEATURE:
<221> NAME/KEY: misc_feature
<222> LOCATION: (4180)..(4180)
<223> OTHER INFORMATION: n = a or t or c or g
<220> FEATURE:
<221> NAME/KEY: misc_feature
<222> LOCATION: (4288)..(4288)
<223> OTHER INFORMATION: n = a or t or c or g
<220> FEATURE:
<221> NAME/KEY: misc_feature
<222> LOCATION: (4290)..(4290)
<223> OTHER INFORMATION: n = a or t or c or g

<400> SEQUENCE: 15

```
gtcttggcac taccacgccc accatgcgag caccggtaac gcttattctc ggcgatgaac   6900
agtggcgcaa gctt                                                     6914 aagcttattc cacgctggag gcgtccggga ttatcggcgt caacgctatc gccggcatcg     60
ccgggaccat catcgccggc atgctctccg accgttttt caaacgcaac cgcagcgtga    120
tggccggatt catcagcctg ctgaacaccg ccggcttcgc cctgatgctc tggtcgccgc    180
acaattacta cactgatatt ctggcgatga ttatcttcgg ggccaccatt ggcgctctga    240
cctgcttcct tggcgggctg atcgccgtcg atatctcttc gcgcaaggcc gccggggccg    300
cgctcggcac catcggcatc gcagctacgc cggcgccggc ctgggcgagt ttctcaccgg    360
gttcattatt gataaaacgg ctatccttga aacggcaaa acgctgtatg atttcagcac    420
gttggcgctg ttctgggtgg gtacggtctg ggttcngcgc tactctgttt taccactgcc    480
gccatcgtcg cccggcgcca tgccgtcgaa cggcagacct cgttctcctc ataaccgatt    540
aacgaataag gaagaagata tgatgcctgc aagacatcag gggctgttac gcctgtttat    600
cgcctgcgcg ctgccgctgc tggcgctgca atctgccgcc gccgcggact ggcagctgga    660
gaaagtggtc gagctcagcc gccacggtat tcgtccgccg acggccggca accgggaagc    720
catcgaggcc gccaccggcc gaccgtggac cgagtggacc acccatgacg gggagctcac    780
cggccatggc tatgccgccg tggtcaacaa agggcgtgcg gaaggccagc attaccgcca    840
gctcggcctg ctgcaggccg gatgcccgac ggcggagtcg atatacgtgc gcgccagccc    900
gctgcagcgg acgcgagcga ccgcccaggc gctggtggat ggcgccttcc ccggctgcgg    960
cgtcgctatc cattatgtca gcggggatgc cgatcccctg tttcagaccg acaagttcgc   1020
cgccacgcaa accgaccccg cccgccagct ggcgcggtga agagaaggc cggggatctg   1080
gcgcaggtcg gcaggcgctg gcgccgacca tccagctatt gaaacaggcg gtttgtcagg   1140
ccgataagcc ctgcccgatc ttcgataccc cgtggcaggt cgagcagagc aaaagtggga   1200
agaccaccat tagcggactg agcgtgatgg ccaatatggt ggagacgctg cgtctcggct   1260
ggagtgaaaa cctgcctctc agccagctgg cgtggggcaa gatcacccag gccaggcaga   1320
```

-continued

```
tcaccgccct gctgccgctg ttaacggaaa actacgatct gagtaacgat gtgttgtata    1380
ccgcgcaaaa acgcgggtcg gtgctgctca acgctatgct cgacggcgtc aaaccggagc    1440
gaatcgaacg tacgctggct gctgctggtg gccatgacac caatatcgcc atggtgcgca    1500
cgctgatgaa ctttagctgg cagctgccgg gctacagccg gggaaatatc ccgccgggca    1560
gcagcctggt gctggagcgc tggcgcaacg cgaagagcgg agaacgctat ctgcgggtct    1620
atttccaggc ccagggcctc gacgacctgc gtcgtctgca cgccggac gcgcagaccc      1680 cgatgctgcg tcaggagtgg catcagccgg gctgccgtca gaccgatgtc ggtacgctgt    1740
gtcccttcca ggcggctatt accgccctcg gtcagcgtat cgaccgatca tccgccccgg    1800
cggtagcatg gtcctgccgt agcggcgcgg tgtttgtccg ggcccgggaa aacctttttt    1860
tccaggccgg cacgacgtcc gttatccgtt gtccggcgca aacgccccgg cggcgacctg    1920
cgccggggtg acaccgctg tccagcaccc agccgcttat cagcccagca ggcgtgacgt     1980
cgaacgccgg attgtaaacg gtggccccg tcggcgccca ctgtaccgcg ccgaagctgc     2040
ccgccactcc ggtcacttcc gccgccgcgc gctgctcaat ggggatcgcc gccccgttcg    2100
ggcaatggcg gtcgagggtg gtctgcgggg cagcgacgta aaacgggatc tggtgataat    2160
gggccaaaac cgccagagaa taggtgccga ttttattcgc cacgtcgccg ttggcggcga    2220
tacggtcggc gccgacccac accgcatcca cctgccctg cgccatcagg ctggcggcca     2280
ttgaatcggc gatcagctga tagggcacgc ccagctcgcc cagctcccag gcggttaaac    2340
gaccgccctg cagcagcggc cgggtttcat caacccatac gttggtcact tttccctgcc    2400
ggtgcgccag cgcgataacg ccgagggcgg tccctacccc ggcggtcgcc aggccaccgg    2460
tgttgcagtg ggtcagcagt cgactgccgg gcttcaccag cgcactgccc gcctcagcga    2520
tgcggtcgca cagctgttta tcttcttcga ccagacgcaa ggcttccgct tccagcgcct    2580
gcgggtaatc tccgggccag cgctgcttca tgcgatcaga ttattcatca ggttgaccgc    2640
cgtcggccgc gccgcgcgca gtctccagcg cctgctggag tgcatcccgg ttcaggccgc    2700
gctgggccag cagggccagc agcaggctgg cggacaggcc aatcagcggc gcgccgcgca    2760
ccccgcaggt atgaatatgg tccaccagca gcgcaacgtt atccgccgcc agccagcgtt    2820
tttcctgcgg caaggcctgc tggtcgagaa taaaaagctg attttcactc acccgcaggc    2880
tggtggtctg taatgtctgc atgtcgttaa atccctgttg cgttgttgta tcacattgtg    2940
tcaggatgga atccagaagt atagacgtct gaacggctta atcagaattc gaggatcgag    3000
gcaatgtcgc aataccatac cttcaccgcc cacgatgccg tggcttacgc gcagagtttc    3060
gccggcatcg acanccatct gagctggtca gcgcgcagga agtgggcgat ggcaactcaa    3120
tctggtgttt aaagtgttcg atcgccaggg cgtcacgggc gatcgtcaaa caggctctgc    3180
cctacgtgcg ctgcgtcggc gaatcctggc cgctgaccct cgaccgcgcc cgtctcgaag    3240
cgcagaccct ggtcgcccac tatcagcaca gcccgcagca cacggtaaaa atccatcact    3300
ttgatcccga gctggcggtg atggtgatgg aagatctttc cgaccaccgc atcttgcgcg    3360
gagagcttat cgctaacgtc tactatcccc aggcggcccg ccagcttggc gactatctgg    3420
cgcaggtgct gtttcacacc agcgatttct acctccatcc ccacgagaaa aaggcgcagg    3480
tggcgcagtt tattaaccg gcgatgtgcg agatcaccga ggatctgttc tttaacgacc     3540
cgtatcagat ccacgagcgc aataactacc cggcggagct gggaggccga tgtcgccgcc    3600
ctgcgcgacg acgctcagct taagctggcg gtggcggcgc tgaagcaccg tttctttgcc    3660
catgcggaag cgctgctgca cggcgatatc cacagcgggt cgatcttcgt tgccgaaggc    3720
```

```
agcctgaagg ccatcgacgc cgagttcggc tacttcggcc ccattggctt cgatatcggc    3780
accgccatcg gcaacctgct gcttaactac tgcggcctgc cgggccagct cggcattcgc    3840
gatgccgccg ccgcgcgcga gcagcggctg aacgacatcc accagctgtg gaccaccttt    3900
gccgagcgct tccaggcgct ggcggcggag aaaacccgcg acgcggcgct ggcttacccc    3960
ggctatgcct ccgcctttct gaaaaaggtg tgggcggacg cggtcggctt ctgcggcagc    4020
gaactgatcc gccgcagcgt cggactgtcg cacgtcgcgg atatcgacac tatccaggac    4080
gacgccatgc gtcatgagtg cctgcgccac gccattaccc tgggcagagc gctgatcgtg    4140
ctggccgagc gtatcgacag cgtcgacgag ctgctggcgc gggtacgcca gtacagctga    4200
gtgcgcctgt ttccctcacc ccaaccctct cccacaggga gagggagcac cccctaaaaa    4260
agtgccattt tctgggattg cccggcgngn tgcgcttgcc gggcctacag atagccgcat    4320
aacggtttga tcttgcactc tttcgtaggc cgggtaaggc gaaagccgcc acccggcaga    4380
catgcgagta caattttgca tttaccttac cctcacccca gatactcaat caccgatagc    4440
ccgccgttgt aatcggtgct gtagataatg ccttgcgcat cgacaaacac gtcacaggac    4500
tggatcaccc gcgggcggcc gggacgggta tccatcattc tctcagcgca gccggcacca    4560 gcgcccggg ctccagcggg cgatacgggt tggaaatgtc gtaagcccgc acgcggcat    4620 tctgatacgt ggcaaaaatc agcgttgagc tgacaaagct ccccggccgg ttctcatgca    4680
ggttgtgcgg accgaaatgc gccccttcg ccacgtaatc cgcttcatcc ggcggcggga    4740
aggtggcgat gctcaccggg ttggttggct cgcggatatc aaacagccag atcagcttct    4800
cgccgtcctc ctggttatcg agcaccgctt catccagcac caccagcaga tcgcgatccg    4860
gcagcggcag cgcggtatgc gttccgccgc cgaacggcgg gctccagttg cgatggctaa    4920
tcagcctcgg ctgggtacgg tctttgacat ccagcagcgt caggccgccg tcgcgccagc    4980
tgcgtaggcg tatccccggc aataatggcg tgatgcagcg catagcgttt gccctgcggc    5040
cagtccggtg tttcaccgcc cgcctggtgc atccccggca gccaccagcg cccggctact    5100
tcgggcttac gcggatcggc cagatcgatg gtcaggaaga tgtagtcggt aaaaccgtcg    5160
atcagcgcag acacatacgc ccagcgcccg ccgacgtacc agatgcggtg aataccgatg    5220
ccgttaagcg acaggaaact gatttcccgc gctgcgcggg agtggaaata tcaaagatgc    5280
gcagcccggc gctccagccc ctgtcctgca catcgctgac cgtgtcaccc accgagcggg    5340
tgtagtacac cttctcatca gcaaaacggg cgtcagcaaa cagatcccgg gcgttgatca    5400
ccagcagcag atcgtcatgc gcctggagtg cacgttccag gtgcccggcg gcgcggcaat    5460
atagttgacg gtggtgggcc gggtcggatc gcgaacatcg accacggaaa aaccctgcga    5520
caccatatgg ccgatatagg cgaatccgcg gtgcaccatc agctgcacgc cgtccggacg    5580
accgccctga tcgctatggc caatcagccg catattgcgg ctgtattcgg gggaaggtaa    5640
tgctgacata ggggatccct ctcgcccggt ggcatggttt tccccctct cctgcggaga    5700 gggccggggc gagggcacca ggccgccgcc caccgccacc cggcttgatt ttatttgttc    5760
ttcgcttcca gcgtcgcgaa ccacggcgcg ataaagtctt cggtctggcc ccagccaggg    5820
ataattttcc ccagcgacgc cacgtttacc gctcccggct gggccgccag cagcgcctgg    5880
ggaatcgctg ccgccttgaa gtcgtaggtg gctggcgtcg gctcgccggc gatcttgttg    5940
gcgatcagcc gcacgttggt cgcgccgata agctt                              5975

<210> SEQ ID NO 16
```

<211> LENGTH: 899
<212> TYPE: DNA
<213> ORGANISM: Candida albicans
<220> FEATURE:
<223> OTHER INFORMATION: Designated as CA-26

<400> SEQUENCE: 16

| | | | | | |
|---|---|---|---|---|---|
| gaattcctag | taagcgcaag | tcatcagctt | gcgttgatta | cgtccctgcc | ctttgtacac | 60 |
| accgcccgtc | gctactaccg | attgaatggc | ttagtgaggc | ctccggattg | gtttaggaaa | 120 |
| gggggcaacc | tcattctgga | accgagaagc | tggtcaaact | tggtcattta | gaggaagtaa | 180 |
| aagtcgtaac | aaggtttccg | tagtgaacct | gcggaaggat | cattactgat | ttgcttaatt | 240 |
| gcaccacatg | tgttttcctt | tgaacaaact | tgctttgcgg | tgggcccagc | ctgccgccag | 300 |
| aggtctaaac | ttacaaccaa | tttttatca | acttgtcaca | ccagattatt | acttaatagt | 360 |
| caaacttcaa | caaacggatc | tcttggttct | cgcagcgaaa | tgcgatacgt | aatatgaatt | 420 |
| gcagatattc | gtgaatcatc | gaatctttga | acgcacattg | cgccctctgg | tattccggag | 480 |
| ggcatgcctg | tttgagcgtc | gtttctccct | caaaccgctg | gtttggtgt | tgagcaatac | 540 |
| gacttgggtt | tgcttgaaag | acggtagtgg | taaggcggga | tcgttgaca | atggcttagg | 600 |
| tctaaccaaa | aacattgctt | gcggcggtaa | cgtccaccac | gtatatcttc | aaactttgac | 660 |
| ctcaaatcag | gtaggactac | ccgctgaact | taagcatatc | aataagcgga | ggaaaagaaa | 720 |
| ccaacaggga | ttgcctcagt | agcggcgagt | gaagcggcaa | agctcaaat | ttgaaatctg | 780 |
| gcgtctttgg | cgtccgagtt | gtaatttgaa | gaaggtatct | ttgggcccgg | ctcttgtcta | 840 |
| tgttccttgg | aacaggacgt | cacagagggt | gagaatcccg | tgcgatgaga | tgacccggg | 899 |

<210> SEQ ID NO 17
<211> LENGTH: 189
<212> TYPE: DNA
<213> ORGANISM: Candida albicans
<220> FEATURE:
<223> OTHER INFORMATION: Designated as CA-26-1

<400> SEQUENCE: 17

| | | | | | |
|---|---|---|---|---|---|
| gcgcaagtca | tcagcttgcg | ttgattacgt | ccctgcccct | tgtacacacc | gcccgtcgct | 60 |
| actaccgatt | gaatggctta | gtgaggcctc | cggattggtt | taggaaaggg | ggcaacctca | 120 |
| ttctggaacc | gagaagctgg | tcaaacttgg | tcatttagag | gaagtaaaag | tcgtaacaag | 180 |
| gtttccgta | | | | | | 189 |

<210> SEQ ID NO 18
<211> LENGTH: 224
<212> TYPE: DNA
<213> ORGANISM: Candida albicans
<220> FEATURE:
<223> OTHER INFORMATION: Designated as CA-26-2

<400> SEQUENCE: 18

| | | | | | |
|---|---|---|---|---|---|
| gctgggtttg | gtgttgagca | atacgacttg | ggtttgcttg | aaagacggta | gtggtaaggc | 60 |
| gggatcgttt | gacaatggct | taggtctaac | caaaaacatt | gcttgcggcg | gtaacgtcca | 120 |
| ccacgtatat | cttcaaactt | tgacctcaaa | tcaggtagga | ctacccgctg | aacttaagca | 180 |
| tatcaataag | cggaggaaaa | gaaaccaaca | gggattgcct | cagt | | 224 |

<210> SEQ ID NO 19
<211> LENGTH: 369
<212> TYPE: DNA
<213> ORGANISM: Candida albicans

```
<220> FEATURE:
<223> OTHER INFORMATION: Designated as CA-26-3

<400> SEQUENCE: 19
aaacggatct cttggttctc gcagcgaaat gcgatacgta atatgaattg cagatattcg        60
tgaatcatcg aatctttgaa cgcacattgc gccctctggt attccggagg gcatgcctgt       120
ttgagcgtcg tttctccctc aaaccgctgg gtttggtgtt gagcaatacg acttgggttt       180
gcttgaaaga cggtagtggt aaggcgggat cgtttgacaa tggcttaggt ctaaccaaaa       240
acattgcttg cggcggtaac gtccaccacg tatatcttca aactttgacc tcaaatcagg       300
taggactacc cgctgaactt aagcatatca ataagcggag gaaaagaaac caacagggat       360
tgcctcagt                                                               369
```